US009872483B2

(12) United States Patent
Cogne et al.

(10) Patent No.: US 9,872,483 B2
(45) Date of Patent: Jan. 23, 2018

(54) TRANSGENIC NON-HUMAN MAMMAL FOR PRODUCING CHIMERIC HUMAN IMMUNOGLOBULIN E ANTIBODIES

(71) Applicants: B CELL DESIGN, Limoges (FR); UNIVERSITE DE LIMOGES, Limoges (FR)

(72) Inventors: Michel Cogne, Isles (FR); Brice Laffleur, Limoges (FR); Armelle Cuvillier, Saint-Jouvent (FR); Marie Bosselut, Condar-sur-Vienne (FR)

(73) Assignees: B CELL DESIGN, Limoges (FR); UNIVERSITE DE LIMOGES, Limoges (FR)

( * ) Notice: Subject to any disclaimer, the term of this patent is extended or adjusted under 35 U.S.C. 154(b) by 0 days.

(21) Appl. No.: 14/900,586

(22) PCT Filed: Jul. 3, 2014

(86) PCT No.: PCT/IB2014/062826
§ 371 (c)(1),
(2) Date: Dec. 21, 2015

(87) PCT Pub. No.: WO2015/001510
PCT Pub. Date: Jan. 8, 2015

(65) Prior Publication Data
US 2016/0157468 A1 Jun. 9, 2016

(30) Foreign Application Priority Data
Jul. 5, 2013 (EP) .................................... 13305964

(51) Int. Cl.
*A01K 67/00* (2006.01)
*C12P 21/00* (2006.01)
*A01K 67/027* (2006.01)
*C07K 16/00* (2006.01)

(52) U.S. Cl.
CPC .......... *A01K 67/0278* (2013.01); *C07K 16/00* (2013.01); *A01K 2217/072* (2013.01); *A01K 2217/15* (2013.01); *A01K 2217/206* (2013.01); *A01K 2227/105* (2013.01); *A01K 2267/01* (2013.01); *C07K 2317/24* (2013.01); *C12N 2800/30* (2013.01); *C12N 2800/80* (2013.01)

(58) Field of Classification Search
None
See application file for complete search history.

(56) References Cited

U.S. PATENT DOCUMENTS 6,458,592 B1 * 10/2002 Jakobovits ............. C07K 16/00 435/320.1
2007/0248601 A1 10/2007 Cogne
2008/0196112 A1 * 8/2008 Romagne ........... A01K 67/0278 800/4

FOREIGN PATENT DOCUMENTS

WO 2008092993 A1 8/2008
WO 2009106773 A2 9/2009

OTHER PUBLICATIONS

Mullins et al. Journal of Clinical Investigation, 1996;97:1557-60.*
Moreadith et al., J. Mol. Med., 1997;75:208-16.*
Kuroiwa et al. Nature Genetics 2004;36:775-80.*
Tong et al. (Nature. Sep. 9, 2010; 467: 211-213.*
Daniels-Wells, T.R., et al., "A Novel IgE Antibody Targeting the Prostate-Specific Antigen as a Potential Prostate Cancer Therapy," BMC Cancer 13:195, Apr. 2013, 13 pages.
Gould, J.H., et al., "Comparison of IgE and IgG Antibody-Dependent Cytotoxicity In Vitro and In a SCID Mouse Xenograft Model of Ovarian Carcinoma," European Journal of Immunology 29(11):3527-3537, Nov. 1999.
Neuberger, M.S., et al., "A Hapten-Specific Chimaeric IgE Antibody With Human Physiological Effector Function," Nature 314(6008):268-270, Mar. 1985.
Teo, PZ., et al., "Using the Allergic Immune System to Target Cancer: Activity of IgE Antibodies Specific for Human CD20 and MUC1," Cancer Immunology, Immunotherapy 61(12):2295-2309, Dec. 2012.
International Search Report dated Nov. 12, 2014, issued in corresponding International Application No. PCT/IB2014/062826, filed Jul. 3, 2014, 5 pages.
Written Opinion dated Nov. 12, 2014, issued in corresponding International Application No. PCT/IB2014/062826, filed Jul. 3, 2014, 6 pages.
International Preliminary Report on Patentability dated Jan. 5, 2016, issued in corresponding International Application No. PCT/IB2014/062826, filed Jul. 3, 2014, 7 pages.

* cited by examiner

*Primary Examiner* — Janice Li
(74) *Attorney, Agent, or Firm* — Christensen O'Connor Johnson Kindness PLLC

(57) ABSTRACT

The invention relates to a transgenic non-human mammal comprising human immunoglobulin mu and epsilon heavy-chain constant transgenes Cμ and Cϵ inserted in place of endogenous mu heavy-chain switch sequence Sμ, and its use for producing chimeric human immunoglobulin E antibodies specific for an antigen of interest.

13 Claims, 13 Drawing Sheets

SEQ ID NO: 10

Figure 1:
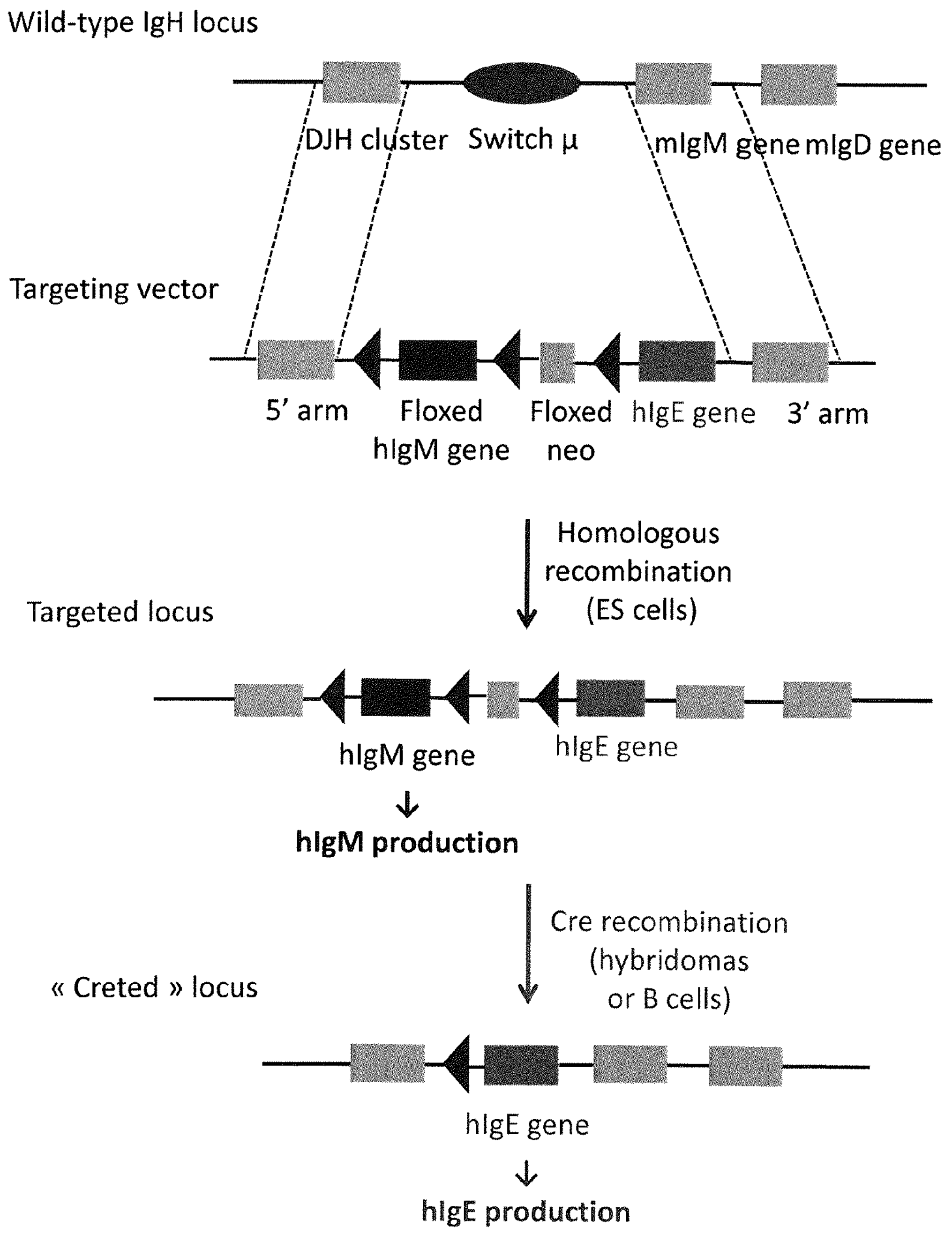

AGCGCGCGTAATACGACTCACTATAGGGCGAATTGGAGCTCCACCGCGGTGGCGGCCGCTCCTGAGAGAACAGACTCTGGAAA
TAGATGGGACTTAAGGAGCTAAGATCTAGAGCTCATCTACAGAGCAGAATCCCAGCCAAGAGAACAAAGAATACTGGCTCTCT
CTCCTGTTCCCTACTCCTAGAGTTCTAAAACACACTATAGGGAAGGGAGCCTCTAGACCTCCGTCCATTCCCCATCTTGCTCA
TTCCATCTTCCCATGTCCCCAGGTCTCCAAGCCACAGACACTACCTTTCCTATTCACCCACCTTTCTGTGTCCCTAGGTCCCC
AGGCCATAGTCACCTCCCCCCACACACACCCCACTCACCCTGCCCCATCTATGCCCCTAGATGCTTACTTACCAGAGTCTTTT
GTCTGACGTGGGGCTACAAGCATCTATGCTCCCTAAGCACCTACTGCTGACCTGTAGGACCCAGCTCTGAACCAACTCATATA
AGTAAATACAGACTCTCCCCTGTCTTAGGATGGCCTCCTGGATCAGGAGGAGACCACTGCCAAAGAACCTTCTCTCAGAGCAC
TGAACTCCTCCCCTGTACCACTTAGGACAGACCTGAGACCTATTATTACTGATTACCAGAGCTCTGGCAGTGACCACGGAGGA
GATAGGTCCACCCTGGACACAGGAAACACAGCAGCAGAGATACTGCTCCATCACAACAGTAGAGTGACACTTTAGACTTTAAT
TTGGGTCACTTTCCTGCTGCAGAGGTGGGATCAGAAAGCAAAGAGCAGTATGAGTGCCTGATAGGCACCCAAGTACACTATAG
AGTACTCATGGTGAATAAGGTACCTCCATGGCTTCCCAGGGAGGGGCAGCCCCACCCCCACCATCACAGACCTTTCTCCATAG
TTGATAACTCAGACACAAGTGAATGACAGATGGACCTCCATCTACTCTTATTTTAAAAAGAAGACAAACCCCACAGGCTCGAG
AACTTTAGCGACTGTTTTGAGAGAAATCATTGGTCCCTGACTCAAGAGATGACTGGCAGATTGGGGATCAGAATACCCATACT
CTGTGGCTAGTGT

DQ52

GAGGTTTAAGCCTCAGAGTCCCTGTGGTCTCTGACTGGTGCAAGGTTTTGACTAAGCGGAGCACCACAGTGCTAACTGGGACC
ACGGTGACACGTGGCTCAACAAAAACCTTCTGTTTGGAGCTCTCCAGGGGCAGCCTGAGCTATGAGGAAGTAGAGAGGCTTGA
GAAATCTGAGGAAGAAAAGAGTAGATCTGAGAGGAAAGGTAGCTTTCTGGAGGTCAGGAGACAGTGCAGAGAAGAACGAGTTA
CTGTGGACAGGTCTTAGATGGGGAAAGAATGAGCAAATGCAAGCATCAGAAGGGTGGATGCAATGTCCTGCCAAGGACTTACC
AAGAGGATCCCCGGACAGAGCAGGCAGGTGGAGTTGACTGAGAGGACAGGGTAGGTGCAGGTCCCTCTCTCGTTTCCTTTCTC
CTTCTCCTGTTTCCTTCCTCTCTTGTCACAGGTCTCACTATGCTAGCCAAGGCTAGCCTGAAAGATTACCATCCTACAGATGG
GCCCATCCAGTTGAGTTAAGGTGGAGATCTCTCCAAACATCTGAGTTTCTGAGGCTTGGATGCCACTGGGGACGCCAAGGGAC
TTTGGGCTGGGTTTGGTTGGCCCCAGATGAAGGGCTACTTCACTGGGTCTATAATTACTCTGATGTCTAGGACCAGGGGGCTC
AGGTCACTCAGGTCAGGTGAGTCCTGCATCTGGGGACT

JH1

GTGGGGTTCAGGTGTCCTAAGGCAGGATGTGGAGAGAGTTTTAGTATAGGAACAGAGGCAGAACAGAGACTGTG**CTACTGGTA
CTTCGATGTCTGGGGCGCAGGGACCACGGTCACCGTCTCCTCAG**GTAAGCTGGCTTTTTTCTTTCTGCACATTCCATTCTGAA
ATGGGAAAAGATATTCTCAGATCTCCCCATGTCAGGCCATCTGCCACACTCTGCATGCTGCAGAAGCTTTTCTGTAAGGATAG
GGTCTTCACTCCCAGGAAAAGAGGCAGTCAGAGGCTAGCTGCCTGTGGAACAGTGACAATCATGGAAAATAGGCATTTACATT
GTTAGGCTACATGGGTAGATGGGTTTTTGTACACCCACTAAAGGGGTCTATGATAGTG

JH2

TGACTACTTTGACTACTGGGGCCAAGGCACCACTCTCACAGTCTCCTCAGGTGAGTCCTTACAACCTCTCTCTTCTATTCAGC
TTAAATAGATTTTACTGCATTTGTTGGGGGGGAAATGTGTGTATCTGAATTTCAGGTCATGAAGGACTAGGGACACCTTGGGA
GTCAGAAAGGGTCATTGGGAGCCCTGGCTGACGCAGACAGACATCCTCAGCTCCCATACTTCATGGCCAGAGATTTATAGGGA
TCCTGGCCAGCATTGCCGCTAGGTCCCTCTCTTCTATGCTTTCTTTGTCCCTCACTGGCCTCC

JH3

ATCTGAGATAATCCTGGAGCCCTAGCCAAGGATCATTTATTGTCAGGGGTCTAATCATTGTTGTCACAATGTG**CCTGGTTTGC
TTACTGGGGCCAAGGGACTCTGGTCACTGTCTCTGCAG**GTGAGTCCTAACTTCTCCCATTCTAAATGCATGTTGGGGGGATTC
TGAGCCTTCAGGACCAAGATTCTCTGCAAACGGGAATCAAGATTCAACCCCTTTGTCCCAAAGTTGAGACATGGGTCTGGGTC
AGGGACTCTCTGCCTGCTGGTCTGTGGTGACATTAGAACTGAAGTATGATGAAGGATCTGCCAGAACTGAAGCTTGAAGTCTG
AGGCAGAATCTTGTCCAGGGTCTATCGGACTCTTGTGAGAATTAGGGGCTGACAGTTGATGGTGACAATTTCAGGGTCAGTGA
CTGTCTGGTTTCTCTGAGGTGAGGCTGGAATATAGGTCACCTTGAAGACTTAAGAGGGGTCCAGGGGGCTTCTGCACAGGCAG
GGAACAGAATGTGGAACAATGACTTGAATGGTTGATTCTTGTGTGACACCAGGAATTGGCATAATGTCTGAGTTGCCCAGGGG
TGATTCTAGTCAGACTCTGGGGTTTTTGTCGGGTATAGAGGAA

JH4

AAATCCACTATTGTGATTACTATGCTATGGACTACTGGGGTCAAGGAACCTCAGTCACCGTCTCCTCAGGTAAGAATGGCCTC
TCCAGGTCTTTATTTTTAACCTTTGTTATGGAGTTTTCTGAGCATTGCAGACTAATCTTGGATATTTGTCCCTGAGGGAGCCG
GCTGAGAGAAGTTGGGAAATAAACTGTCTAGGGATCTCAGAGCCTTTAGGACAGATTATCTCCACATCTTTGAAAAACTAAGA
ATCTGTGTGATGGTGTTGGTGGAGTCCCTGGATGATGGGATAGGGACTTTGGAGGCTCATTTGAGGGAGATGCTAAAACAATC
CTATGGCTGGAGGGATAGTTGGGGCTGTAGTTGGAGATTTTCAGTTTTTAGAATAAAAGTATTAGCTGCGGAATATACTTCAG
GACCACCTCTGTGACAGCATTTATACAGTATCCGATGCATAGGGACAAAGAGTGGAGTGGGGCACTTTCTTTAGATTTGTGAG
GAATGTTCCACACTAGATTGTTTAAAACTTCATTTGTTGGAAGGAGAGCTGTCTTAGTGATTGAGTCAAGGGAGAAAGGCATC
TAGCCTCGGTCTCAAAAGGGTAGTTGCTGTCTAGAGAGGTCTGGTGGAGCCTGCAAAAGTCCAGCTTTCAAAGGAACACAGAA
GTATGTGTATGGAATATTAGAAGATGTTGCTTTTACTCTTAAGTTGGTTCCTAGGAAAAATAGTTAAATACTGTGACTTTAAA
ATGTGAGAGGGTTTTCAAGTACTCATTTTTTTAAATGTCCAAAATTTTTGTCAATCAATTTGAGGTCTTGTTTGTGTAGAACT
GACATTACTTAAAGTTTAACCGAGGAATGGGAGTGAGGCTCTCTCATAACCTATTCAGAACTGACTTTTAACAATAATAAATT
AAGTTTCAAATATTTTTAAATGA

FIGURE 2

Core Eμ
ATTGAGCAATGTTGAGTTGGAGTCAAGATGGCCGATCAGAACCAGAACACCTGCAGCAGCTGGCAGGAAGCAGGTCATGTGGC
AAGGCTATTTGGGGAAGGGAAAATAAAACCACTAGGTAAACTTGTAGCTGTGGTTTGAAGAAGTGGTTTTGAAACACTCTGTC
CAGCCCCACCAAACCGAAAGTCCAGGCTGAGCAAAACACCACCTGGGTAATTTGCATTTCTAAAATAAGTTGAGGATTCAGCC
GAAACTGGAGAGGTCCTCTTTTAACTTATTGAGTTCAACCTTTTAATTTTAGCTTGAGTAGTTCTAGTTTCCCCAAACTTAAG
TTTATCGACTTCTAAAATGTATTTAGAATTCATTTTCAAAATTAGGTTATGTAAGAAAMouse I mu exon
TTGAAGGACTTTAGTGTCTTTAATTTCTAATATATTTAGAAAACTTCTTAAAATTACTCTATTATTCTTCCCTCTGATTATTG
GTCTCCATTCAATTCTTTTCCAATACCCGAAGCATTTACAGTGACTTTGTTCATGATCTTTTTTAGTTGTTTGTTTTGCCTTA
CTATTAAGACTTTGACATTCTGGTCAAAACGGCTTCACAAATCTTTTTCAAGACCACTTTCTGAGTATTCATTTTAGGAGAAA
GACTTTTTTTTTAAATGAATGCAATTATCTAGACTTATTTCAGTTGAACATGCTGGTTGGTGGTTGAGAGGACACTCAGTCAG
TCAGTGGCGTGAAGGGCTTCTAAGCCAGTCCACATGCTCTGTGTGAACTCCCTCTGGCCCTGCTTATTGTTGAATGGGCCAAA
GGTCTGAGACCAGGCTGCTGCTGGGTAGGCCTGGACTTTGGGTCTCCCACCCAGACCTGGGAATGTATGGTTGTGGCTTCTGC
CACCCATCCACCTGGCTGCTCATGGACCAGCCAGCCTCGGTGGCTTTGAAGGAACAATTCCACACAAAGACTCTGGACCTCTC
CGAAACCAGGCACCGCAAATGGTAAGCCAGAGGCAGCCACAGCTGTGGCTGCTGCTCTTAAAGCTTGTAAACTGTTTCTGCTT
AAGAGGGACTGAGTCTTCAGTCATTGCTTTAGGGGGAGAAAGAGACATTTGTGTGTCTTTTGAGTACCGTTGTCTGGGTCACT
CACATTTAACTTTCCTTGAAAAACTAGACTCGACATCGATTGTCGAGGAATTCCGATCATATTCAATAACCCTTAATATAACT
TCGTATAATGTATGCTATACGAAGTTATTAGGTCT
loxP

Human C mu exon CH1
GAAGAGGAGTTTACGTCCAGCCTTCGAAGGGTCCTCAGGGAGTGCATCCGCCCCAACCCTTTTCCCCCTCGTCTCCTGTGAGA
ATTCCCCGTCGGATACGAGCAGCGTGGCCGTTGGCTGCCTCGCACAGGACTTCCTTCCCGACTCCATCACTTTCTCCTGGAAA
TACAAGAACAACTCTGACATCAGCAGCACCCGGGGCTTCCCATCAGTCCTGAGAGGGGGCAAGTACGCAGCCACCTCACAGGT
GCTGCTGCCTTCCAAGGACGTCATGCAGGGCACAGACGAACACGTGGTGTGCAAAGTCCAGCACCCCAACGGCAACAAAGAAA
AGAACGTGCCTCTTCCAGGTGAGGGCCGGGCCCAGCCACCGGGACAGAGAGGGAGCCGAAGGGGGGCGGGAGTGGCGGGCACC
GGGCTGACACGTGTCCCTCACTG

Human C mu exon CH2
CAGTGATTGCTGAGCTGCCTCCCAAAGTGAGCGTCTTCGTCCCACCCCGCGACGGCTTCTTCGGCAACCCCCGCAAGTCCAAG
CTCATCTGCCAGGCCACGGGTTTCAGTCCCCGGCAGATTCAGGTGTCCTGGCTGCGCGAGGGGAAGCAGGTGGGGTCTGGCGT
CACCACGGACCAGGTGCAGGCTGAGGCCAAAGAGTCTGGGCCCACGACCTACAAGGTGACCAGCACACTGACCATCAAAGAGA
GCGACTGGCTCAGCCAGAGCATGTTCACCTGCCGCGTGGATCACAGGGGCCTGACCTTCCAGCAGAATGCGTCCTCCATGTGT
GTCCCCGGTGAGTGACCTGTCCCCAGGGGCAGCACCCACCGACACACAGGGGTCCACTCGGGTCTGGCATTCGCCACCCCGGA
T

Human C mu exon CH3
GCAGCCATCTACTCCCTGAGCCTTGGCTTCCCAGAGCGGCCAAGGGCAGGGGCTCGGGCGGCAGGACCCCTGGGCTCGGCAGA
GGCAGTTGCTACTCTTTGGGTGGGAACCATGCCTCCGCCCACATCCACACCTGCCCCACCTCTGACTCCCTTCTCTTGACTCC
AGATCAAGACACAGCCATCCGGGTCTTCGCCATCCCCCCATCCTTTGCCAGCATCTTCCTCACCAAGTCCACCAAGTTGACCT
GCCTGGTCACAGACCTGACCACCTATGACAGCGTGACCATCTCCTGGACCCGCCAGAATGGCGAAGCTGTGAAAACCCACACC
AACATCTCCGAGAGCCACCCCAATGCCACTTTCAGCGCCGTGGGTGAGGCCAGCATCTGCGAGGATGACTGGAATTCCGGGGA
GAGGTTCACGTGCACCGTGACCCACACAGACCTGCCCTCGCCACTGAAGCAGACCATCTCCCGGCCCAAGGGTAGGCCCCACT
CTTGCCCCTCTTCTGCACTCCTGCAACTCCTTGCCTCTGGGGGCATGGTGGAAAGCACCCCTCACTCCCCCGTTGTCTGGGCA
ACTGGGGAAAAGGGGACTCAACCCCAGCCCACAGGCTGGTCCCCCCACTGCCCCGCCCTCACCACCATCTCTGTTCA

Human C mu exon CH4
CAGGGGTGGCCCTGCACAGGCCCGATGTCTACTTGCTGCCACCAGCCCGGGAGCAGCTGAACCTGCGGGAGTCGGCCACCATC
ACGTGCCTGGTGACGGGCTTCTCTCCCGCGGACGTCTTCGTGCAGTGGATGCAGAGGGGGCAGCCCTTGTCCCCGGAGAAGTA
TGTGACCAGCGCCCCAATGCCTGAGCCCCAGGCCCCAGGCCGGTACTTCGCCCACAGCATCCTGACCGTGTCCGAAGAGGAAT
GGAACACGGGGGAGACCTACACCTGCGTGGTGGCCCATGAGGCCCTGCCCAACAGGGTCACCGAGAGGACCGTGGACAAGTCC
ACCGGTAAACCCACCCTGTACAACGTGTCCCTGGTCATGTCCGACACAGCTGGCACCTGCTACTGACCCTGCTGGCCTGCCCA
CAGGCTCGGGGCGGCTGGCCGCTCTGTGTGTGCATGCAAACTAACCGTGTCAACGGGGTGAGATGTTGCATCTTATAAAATTA
GAAATAAAAAGATCCATTCAAAAGATACTGGTCCTGAGTGCACGATGCTCTGGCCTACTGGGGCGGCGGCTGTGCTGCACCC
ACCCTGCGCCTCCCCTGCAGAACACCTTCCTCCACAGCCCCCACCCCTGCCTCACCCACCTGCGTGCCTCAGTGGCTTCTAGA
AACCCCTGAATTCCCTGCAGCTGCTCACAGCAGGCTGACCTCAGACTTGCCATTCCTCCTACTGCTTCCAGAAAGAAAGCTGA
AAGCAAGGCCACACGTATACAGGCAGCACACAGGCATGTGTGGATACACATGGACAGACACGGACACACACAAACACATGGAC
ACACAGAGACGTGCTAACCCATGGGCACACACATACACAGACATGGACCCACACACAAACATATGTGGACACACATGTACAAA
CATGCACAGGCACACAAAGAGAACACTGACTACAGGCACACACACACACGGGCACACACATGGATATGTGCACACATGGACAC
ATACATGTGCAGGACATGCACACACACAGACACACTAGCACAGAGGCATACACACACAGACACACACATTCACAAACACACAT FIGURE 2 (Continued)

GTGCATGCAAACACACACACATGTACAGACACGAGTACATGGACACATGCACACCCAGAGACACACTGACACAGACACACAGG
AGCATGTGATACACTAACACGTGGACACACACGTCTACCCACAGGCACACAACAGATGGACACGCGTACACAGACATGCACAC
ACCCACAGGCACAACACGTGCGCATGCCGGCCGGCCCCCGCCCACATTCTCCCAGGGCCCTGCCGGATACTCTGTCCCTGCAG
CAGTTTGCTCCCTGCGCTGTGCTGGCCCCGGGGCTTTGGGCCCAGGCTCTGCTTGTCCTTCTGTCTCTGCTTGGAGGTGCTGC
CATGGCACCCAGCTTGGGCTCTGCCTGGGGAGCGGAGGCCCCAGGGATAGCATGTGACCCCTGCTGAGGCCAGGCTCCTGATG
AAGGCAGCAGATAGCCCCCACACCCACCGGTGAGCAGAACCAGAGCCTGTGCCATGTGCTGAGAGCAGGCAGTGACTAAGCAT
ATGGGCCCAGAGGGCAGAGTGGCTGCCCTGGGCAGCTGCTCCTCTTAGCGGGAGGCCTCAGGAGATGAGCTAGAGCAAGTCTG
CCCCTGCAAATACCACCTGCTCCCCAACCCACAGCAGGGAGCAGGCGAGGTCAGACAGCAGCAGCCCGGGAAGGACCGAGCCC
CAGCAGGGAAGGCAGGGCCCGAGTGAGGTCTCCACACCCAACGCACAGTGCTGTCTCTAACTGGGGCCACCTCCGAGTCCCCG
CCACACTCTTGGCCCTTTGGAGTCCTGGGCTCCAGGTGTCTCCCAAGGGCCCATCTGTGCAGGGGATGCAACCCCCCGAATGT
CCTCATCCCACTGTGGAGCTCAGGTCTCTGTCTGCTCCCTGGGTCCTGGCAGGGTAGGACAAGTCCGCCAGGATGTCCCCATG
CAGACTCTGCTCCAAGAGGGAGCTGGAGAGTCAGGGCCTTGGTGAGGGAGTCAGGATCGGGTTCCCCCCAGCTCAGTCCTCCC
ACCTGCCAGCCCCCACAGCACAGGGCAGGGCCACACCCCCTGCTTCCCCCTCCAGGAGAGTCAGGACATGCTGGCCGCTGCTC
CGCTGGGGCCCCGCCCTCCAGCCCCCACCTTGGTCTGTGTGCTGCATCCCCCACGCTCTCTCTGCCACCCCAGGACTCTGAGG
AAAAGACCTCAGAGTCCCAGCCCTGCCCAGTCTCGGCCTGTGCCCCCGCTGCATCAGGCTTTCAGGGGCCCAGCCCATGCCCT
GGGCAGTGCCCGAGCCCCCCTGCACTTGCTCTCCCCACCCCTGGGTGCAGCACAGCCTAGGGGCCAAGGGTGGGCCTAGAGGA
TGGGCCCCGGGGGGGCTTTGCTGGGTGCCACCCCAGCCTGACCCTATTCCCCCGTGCTGTGTCTCCTG

Human C mu exon M1

CAGAGGGGGAGGTGAGCGCCGACGAGGAGGGCTTTGAGAACCTGTGGGCCACCGCCTCCACCTTCATCGTCCTCTTCCTCCTG
AGCCTCTTCTACAGTACCACCGTCACCTTGTTCAAGGTAGCACGGCTGTGGCACAGGGAGGAGGGTGCAGGGCGAGTGTGGGG
CCCAGGGAGCAGCCTGGGCTGGACGTCTAGCCCGGAGGCCCCCACACCACCCCACTGGGTCATCTCTGCCCCGGCTCCCTTCC
CGACCACGGGGAAAGCATTTCACACTGTCTCTGTTGCCTGTAG

Human C mu exon M2

GTGAAATGATCCCAACAGAAGAACATCGGAGACCAGAGAGAGGAACTCAAAGGGGCGCTGCCTCCGGGTCTGGGGTCCTGGCC
TGCGTGGCCTGTTGGCACGTGTTTCTCTTCCCCGCCCGGCCTCCAGTTGTGTGCTCTCACACAGGCTTCTTTCTCGACCGGCA
GGGGCTGGCTGGCTTGCAGGCCACGAGGTGGGGCTCTACCCCACACTGCTTTGCTGTGTATACGCTTGTTGCCTGAAATAAA
TATGCACATTTTATCCATGAAACTGCTTTCTGGTGAGGGTTTGTTTCTTTTTCAAAACTTTCCTGCTACAGGGCATTCAAGCC
ATCGAT loxP
GTCGAGGAATTCCGATCATATTCAATAACCCTTAATATAACTTCGTATAATGTATGCTATACGAAGTTATTAGGTCTGAAGAG
GAGTTTACGTCCAGCCAAGCTAGCTTGGCTGCAGGTCGAGCAGTGTGGTTTTCAAGAGGAAGCAAAAAGCCTCTCCACCCAGG
CCTGGAATGTTTCCACCCAATGTCGAGCAGTGTGGTTTTGCAAGAGGAAGCAAAAAGCCTCTCCACCCAGGCCTGGAATGTTT
CCACCCAATGTCGAGCAGTGTGGTTTTGCAAGAGGAAGCAAAAAGCCTCTCCACCCAGGCCTGGAATGTTTCCACCCAATGTC
GAGCAAACCCCGCCCAGCGTCTTGTCATTGGCGAATTCGAACACGCAGATGCAGTCGGGGCGGCGCGGTCCCCAGGTCCACTT
CGCATATTAAGGTGACGCGTGTGGCCTCGAACACCGAGCGACCCTGCAGCCAATATGGGATCGGCCATTGAACAAGATGGATT
GCACGCAGGTTCTCCGGCCGCTTGGGTGGAGAGGCTATTCGGCTATGACTGGGCACAACAGACAATCGGCTGCTCTGATGCCG
CCGTGTTCCGGCTGTCAGCGCAGGGGCGCCCGGTTCTTTTTGTCAAGACCGACCTGTCCGGTGCCCTGAATGAACTGCAGGAC
GAGGCAGCGCGGCTATCGTGGCTGGCCACGACGGGCGTTCCTTGCGCAGCTGTGCTCGACGTTGTCACTGAAGCGGGAAGGGA
CTGGCTGCTATTGGGCGAAGTGCCGGGGCAGGATCTCCTGTCATCTCACCTTGCTCCTGCCGAGAAAGTATCCATCATGGCTG
ATGCAATGCGGCGGCTGCATACGCTTGATCCGGCTACCTGCCCATTCGACCACCAAGCGAAACATCGCATCGAGCGAGCACGT
ACTCGGATGGAAGCCGGTCTTGTCGATCAGGATGATCTGGACGAAGAGCATCAGGGGCTCGCGCCAGCCGAACTGTTCGCCAG
GCTCAAGGCGCGCATGCCCGACGGCGAGGATCTCGTCGTGACCCATGGCGATGCCTGCTTGCCGAATATCATGGTGGAAAATG
GCCGCTTTTCTGGATTCATCGACTGTGGCCGGCTGGGTGTGGCGGACCGCTATCAGGACATAGCGTTGGCTACCCGTGATATT
GCTGAAGAGCTTGGCGGCGAATGGGCTGACCGCTTCCTCGTGCTTTACGGTATCGCCGCTCCCGATTCGCAGCGCATCGCCTT
CTATCGCCTTCTTGACGAGTTCTTCTGAGGGGATCGGCAATAAAAAGACAGAATAAAACGCACGGGTGTTGGGTC loxP
GTTTGTTCGGATCAGCTTCCGATCATATTCAATAACCCTTAATATAACTTCGTATAATGTATGCTATACGAAGTTATT
AGGTCTGAAGAGGAGTTTACGTCCAGCCAAGCTAACTTGGCGCCCCCACTAGGGTCGA

Human C epsilon exon CH1

GGAGCTTGGTACCGAGCTCGGATCCACTAGTAACGGCCGCCAGTGTGCTGGAATTCGCCCTTGATGAATGAGCCTGGCATCTG
GCTCCCTGCCACGGGGTCCCCAGCTCCCCCATCCAGGCCCCCCAGGCCTGATGGGCGCTGGCCTGAGGCTGGCACTGACTAGG
TTCTGTCCTCACAGCCTCCACACAgAGCCCATCCGTCTTCCCCTTGACCCGCTGCTGCAAAAACATTCCCTCCAATGCCACCT
CCGTGACTCTGGGCTGCCTGGCCACGGGCTACTTCCCGGAGCCGGTGATGGTGACCTGGGACACAGGCTCCCTCAACGGGACA
ACTATGACCTTACCAGCCACCAcCCTCACGCTCTCTGGTCACTATGCCACCATCAGCTTGCTGACCGTCTCGGGTGCGTGGGC
CAAGCAGATGTTCACCTGCCGTGTGGCACACACTCCATCGTCCACAGACTGGGTCGACAACAAAACCTTGAGCGGTAAGAGAG
GGCCAAGCTCAGAGACCACAGTTCCCAGGAGTGCCAGGCTGAGGGCTGGCAGAGTGGGCAGGGGTTGAGGGGGTGGGTGGGCT
CAAACGTGGGAACACCCAGCATGCCTGGGGACCCGGGCCAGGACGTGGGGGCAAGAGGAGGGCACACAGAGCTCAGAGAGCCC
AACAACCCTCATGACCACCAGCTCTCCC

FIGURE 2 (Continued)

Human C epsilon exon CH2
CCAGTCTGCTCCAGGGACTTCACCCCGCCCACCGTGAAGATCTTACAGTCGTCCTGCGACGGCGGCGGGCACTTCCCCCCGAC
CATCCAGCTCCTGTGCCTCGTCTCTGGGTACACCCCAGGGACTATCAACATCACCTGGCTGGAGGACGGGCAGGTCATGGACG
TGGACTTGTCCACCGCCTCTACCACGCAGGAGGGTGAGCTGGCCTCCACACAAAGCGAGCTCACCCTCAGCCAGAAGCACTGG
CTGTCAGACCGCACCTACACCTGCCAGGTCACCTATCAAGGTCACACCTTTGAGGACAGCACCAAGAAGTGTGCAGGTACGTT
CCCACCTGCCCTGGTGGCCGCCACGGAGGCCAGAGAAGAGGGGCGGGTGGGCCTCACACAGCCCTCCGGTGTACCAC
Human C epsilon exon CH3
AGATTCCAACCCGAGAGGGGTGAGCGCCTACCTAAGCCGGCCCAGCCCGTTCGACCTGTTCATCCGCAAGTCGCCCACGATCA
CCTGTCTGGTGGTGGACCTGGCACCCAGCAAGGGGACCGTGAACCTGACCTGGTCCCGGGCCAGTGGGAAGCCTGTGAACCAC
TCCACCAGAAAGGAGGAGAAGCAGCGCAATGGCACGTTAACCGTCACGTCCACCCTGCCGGTGGGCACCCGAGACTGGATCGA
GGGGGAGACCTACCAATGCAGGGTGACCCACCCCCACCTGCCCAGGGCCCTCATGCGGTCCACGACCAAGACCAGCGGTGAGC
CATGGGCAGGCCGGGGTCGTGGGGAAGGGAGGGAGCGAGTGAGCGGGGCCCGGGCTGACCCCACGTCTGGCCAC
Human C epsilon exon CH4
AGGCCCGCGTGCTGCCCCGGAAGTCTATGCGTTTGCGACGCCGGAGTGGCCGGGGAGCCGGGACAAGCGCACCCTCGCCTGCC
TGATCCAGAACTTCATGCCTGAGGACATCTCGGTGCAGTGGCTGCACAACGAGGTGCAGCTCCCGGACGCCCGGCACAGCACG
ACGCAGCCCCGCAAGACCAAGGGCTCCGGCTTCTTCGTCTTCAGCCGCCTGGAGGTGACCAGGGCCGAATGGGAGCAGAAAGA
TGAGTTCATCTGCCGTGCAGTCCATGAGGCAGCGAGCCCCTCACAGACCGTCCAGCGAGCGGTGTCTGTAAATCCCGGTAAAT
GACGTACTCCTGCCTCCCTCCCTCCCAGGGCTCCATCCAGCTGTGCAGTGGGGAGGACTGGCCAGACCTTCTGTCCACTGTTG
CAATGACCCCAGGAAGCTACCCCCAATAAACTGTGCCTGCTCAGAGCCCCAGGTACACCCATTCTTGGGAGCGGGCAGGGCT
GTGGGCAGGTGCATCTTGGCACAGAGGAATGGGCCCCCCAGGAGGGGCAGTGGGAGGAGGTGGGCAGGGCTGAGTCCCCCCAG
GAGAGGTGGTGGGAGGAGGTGGGCAGGGGTGAGGTGCCACTCATCCATCTGCCTTCGTGTCAGGGTTATTTGTCAAACAGCAT
ATCTGCAGGGACTCATCACAGCTACCCCGGGCCTCTCTGCCCCCACTCTGGGTCTACCCCCTCCAAGGAGTCCAAAGACCCAG
GGGAGGTCCTCAGGGAAGGGGCAAGGGAGCCCCCACAGCCCTCCCTCTTGGGGGCTTGGCTTCTACCCCCCTGGACAGGAGCC
CCTGCACCCCCAGGTATAGATGGGCACACAGGCCCCTCCAGGTGGAAAAACAGCCCTAAGTGAAACCCCCACACAGACACACA
CAACCCGACAGCCCTCGCCCAAGTCTGTGCCACTGGCGTTCGCCTCTCTGCCCTGTCCCGCCTTGCCGAGTCCTGGCCCCAGC
ACCGGGGCCGGTGGAGCCGAGCCCACTCACACCCCGCAGCCTCCGCCACCCTGCCCTGTGGGCACACCAGGCCCAGGTCAGAG
CCAGGCCCCCTCTCCTACTGCCCCCCACCGCCCCTTGGTCCATCCTGAATCGGCCTCCAGGGGATCGCCAGCCTCACACACCC
GGTCTCGCCCACTCACGCCTCACTCAAGGCACAGCTGTGCACACACTAGGCCCCATAGCAACTCCACAGCACCCTGTACCACC
ACCAGGGCGCCATAGACACCCCACACGTGGTCACACGTGGCCCACACTCCGCCTCTCACGCTGCCTCCAGCCAGGCTACTGCC
AAGCCCTTCCTCTGAGCCATACCTGGGCCGCTGGATCCCAGAGAGAAATGGAGAGGCCCTCACGTGGTGTCCTCCAGTCCAAC
CCTCCCTGTCACCCTGTCAGCAGCACCCCACAGCCAAACACAGGATGGATGCGTGGGCTCCATCCCCCACTCACCCACACCTG
AACCCCAGAGCAGGCTACGTGCCCCTCACAGACCTCAAACCCACATGTGCATCTGACACCCCAGATCCAAACGCTCCCCCCGG
TCATGCACACCAAGGGCACAGCACCCACCAAATCCACACGGAAACACGGGCACCGGGCACCCCATGAGCACAAAGCCCCTCCA
TGTCTGAAGACAGTCCCTGCACACCGTCACAGCCATACATTCAGCTTCACTCTCACGTCCCAGCCCACCTGCACCCAGCTCTG
GGCCTGGAGCAGCAGAAAGAGGTGTGAGGGCCCGAGGCCGGACCTGCACCTGCTGATGACCCGGGACCAGCAGGCAGCTCACG
GTGTTGGGGAAGGGAGTGGAGGGCACCCAGGGCAGGAGCCAGAGGGACCAGGCTGGTGGGCGGGGCCGGGCCGGGGTAGGGCC
AGGAGGCAGCTCTGGACACCCACAGGCCTGGGCTCATAGTCCACACCAGGACAGCCCCTCAGAGCACCCATGCAGTGAGTCCC
AGGTCTTGGGAGCCAGGCCGCAGAGCTCACGCATCCTTCCGAGGGCCCTGAGTGAGGCGGCCACTGCTGCGCCGAGGGGTTGG
GTCCTTCTCTGGGGAGGGCGTGGGGTCTAGAGAGGCGGAGTGGAGGTAACCAGAGGTCAGGAGAGAAGCCGTAAGGAACAGAG
GGAAAATGGGGCCAGAGTCGGGGCGCAGGGACGAGAGGTCAGGAGTGGTCGGCCTGGCCCTGGGCCGTTGACTGACTCGGGAC
CTGGGTGCCCACCCTC
Human C epsilon exon M1
AGGGCTGGCTGGCGGCTCCGCGCAGTCCCAGAGGGCcCCGGAtAGGGTGCTCTGCCACTCCGGACAGCAGCAGGGACTGCCGA
GAGCGGCAGGAGGCTCTGTCCCCCACCCCCGCTGCCACTGTGGAGCCGGGAGGGCTGACTGGCCAGGTCCCCCAGAGCTGGAC
GTGTGCGTGGAGGAGGCCGAGGGCGAGGCGCCGTGGACGTGGACCGGCCTCTGCATCTTCGCCGCACTCTTCCTGCTCAGCGT
GAGCTACAGCGCCGCCCTCACGCTCCTCATGGTGGGCACCCACCTCCAGGGGCCCAGCCAGGGCAGGGGGTTGGGCAGAGCCA
GCAGAGCGCCCTGACCCACGCCCTCCCCTC
Human C epsilon exon M2
AGGTGCAGCGGTTCCTCTCAGCCACGCGGCAGGGGAGGCCCCAGACCTCCCTCGACTACACCAACGTCCTCCAGCCCCACGCC
TAGGCCGCGGGCCACTCACGCTCCACCAGGCCCAGCTTTTTCTCTGCCAGCGCCTGAGCCTCCCTCGGGCTGCACCCTGCCCT
GGGTGGGAAAAGGGAAGCAGACAAGAAAAGGGGGCACAAGGTCACTACTGTGGGCTGATGGCCAGTGAACCTGAGCCCAGAG
GGGCCGGCTCAGCCGCAAGGTTACAGGCGCCGAGAGAACCACCAGTCGCAGCCCCCACCCGAAAACCGTGTCTGTCCCTTCAA
CAGAGTCATCGAGGAGGGGTGGCTGCTAGCCGTTCTGAGCTCATCGAAGGGCGAATTCTGCAGATATCCATCACACTGGCGGC
CGCTCGACCTAGGATCTCCTGTCTG
Mouse C mu exon CH1
ACAGGAGGCAAGAAGACAGATTCTTACCCCTCCATTTCTCTTTTATCCCTCTCTGGTCCTCAGAGAGTCAGTCCTTCCCAAAT
GTCTTCCCCCTCGTCTCCTGCGAGAGCCCCCTGTCTGATAAGAATCTGGTGGCCATGGGCTGCCTGGCCCGGGACTTCCTGCC FIGURE 2 (Continued)

CAGCACCATTTCCTTCACCTGGAACTACCAGAACAACACTGAAGTCATCCAGGGTATCAGAACCTTCCCAACACTGAGGACAG
GGGGCAAGTACCTAGCCACCTCGCAGGTGTTGCTGTCTCCCAAGAGCATCCTTGAAGGTTCAGATGAATACCTGGTATGCAAA
ATCCACTACGGAGGCAAAAACAGAGATCTGCATGTGCCCATTCCAGGTAAGAACCAAACCCTCCCAGCAGGGGTGCCCAGGCC
CAGGCATGGCCCAGAGGGAGCAGCGGGTGGGGCTTAGGCCAAGCTGAGCTCAC

Mouse C mu exon CH2

ACCTTGACCTTTCATTCCAGCTGTCGCAGAGATGAACCCCAATGTGTTCGTCCCACCACGGGATGGCTTCTCTGGCCCTGCAC
CACGCAAGTCTAAACTCATCTGCGAGGCCACGAACTTCACTCCAAAACCGATCACAGTATCCTGGCTAAAGGATGGGAAGCTC
GTGGAATCTGGCTTCACCACAGATCCGGTGACCATCGAGAACAAAGGATCCACACCCCAAACCTACAAGGTCATAAGCACACT
TACCATCTCTGAAATCGACTGGCTGAACCTGAATGTGTACACCTGCCGTGTGGATCACAGGGGTCTCACCTTCTTGAAGAACG
TGTCCTCCACATGTGCTGCCAGTGAGTGGCCTGGGATAAGCCCAATGCCTAGCCCTCCCAGATTAGGGAAGTCCTCCTACAAT
TATGGCCAATGCCACCCAGACATGGTCATTTGCTCCTTGAACTTTGGCTCCCCAGAGTGGCCAAGGACAAGAATGAGCAATAG
GCAGTAGAGGGGTGAGAATCAGCTGGAAGGACCAGCATCTTCCCTTAAGTAGGTTTGGGGGATGGAGACTAAGCTTTTTTCCA
ACTTCACAACTAGATATGTCATAACCTGACACAGTGTTCTCTT

Mouse C mu exon CH3

GACTGCAGGTCCCTCCACAGACATCCTAACCTTCACCATCCCCCCTCCTTTGCCGACATCTTCCTCAGCAAGTCCGCTAACC
TGACCTGTCTGGTCTCAAACCTGGCAACCTATGAAACCCTGAATATCTCCTGGGCTTCTCAAAGTGGTGAACCACTGGAAACC
AAAATTAAAATCATGGAAAGCCATCCCAATGGCACCTTCAGTGCTAAGGGTGTGGCTAGTGTTTGTGTGGAAGACTGGAATAA
CAGGAAGGAATTTGTGTGTACTGTGACTCACAGGGATCTGCCTTCACCACAGAAGAAATTCATCTCAAAACCCAATGGTAGGT
ATCCCCCCTTCCCTTCCCCTCCAATTGCAGGACCCTTCCTGTACCTCATAGGGAGGGC

Mouse C mu exon CH4

AGGTCCTCTTCCACCCTATCCTCACTACTGTCTTCATTTACAGAGGTGCACAAACATCCACCTGCTGTGTACCTGCTGCCACC
AGCTCGTGAGCAACTGAACCTGAGGGAGTCAGCCACAGTCACCTGCCTGGTGAAGGGCTTCTCTCCTGCAGACATCAGTGTGC
AGTGGCTTCAGAGAGGGCAACTCTTGCCCCAAGAGAAGTATGTGACCAGTGCCCCGATGCCAGAGCCTGGGGCCCCAGGCTTC
TACTTTACCCACAGCATCCTGACTGTGACAGAGGAGGAATGGAACTCCGGAGAGACCTATACCTGTGTTGTAGGCCACGAGGC
CCTGCCACACCTGGTGACCGAGAGGACCGTGGACAAGTCCACTGGTAAACCCACACTGTACAATGTCTCCCTGATCATGTCTG
ACACAGGCGGCACCTGCTATTGACCATGCTAGCGCTCAACCAGGCAGGCCCTGGGTGTCCAGTTGCTCTGTGTATGCAAACTA
ACCATGTCAGAGTGAGATGTTGCATTTTATAAAAATTAGAAATAAAAAAAATCCATTCAAACGTCACTGGTTTTGATTATAC
AATGCTCATGCCTGCTGAGACAGTTGTGTTTTGCTTGCTCTGCACACACCCTGCATACTTGCCTCCACCCTGGCCCTTCCTCT
ACCTTGCCAGTTTCCTCCTTGTGTGTGAACTCAGTCAGGCTTACAACAGACAGAGTATGAACATGCGATTCCTCCAGCTACTT
CTTGATATATGGCTGAAAGCTTGCCTAACCTGGTGCAGGCAGCATTCAGGCACATATATAGACACACATGCATTTATACATAG
ATATATAGGTACACATGTGTAGACACATACATGAATGTGTATTCATGGACACACAGACAAAGGTACACATATATACACATGAG
TTCATGCGCACACACATGCATGGACACTTACAAACGCCTTCAGAGACAAATAGGCATAGACACACAACCACTCACAGAAACAG
ATACCAATATGCATGGTCCTGTGTACACAGAAACAGACTATAGGCAAATATACACAAATAAACTATATAGATACAAAGATATG
CATATACACACATGTACAGAAACATCTTCACATGTGTACACTAACATGTGGACAGGTATAGCACACAGATACACCTGGACTCT
GACCAGGGCTGTAATCTCCAAGGCTCACGGCTCAGAGAGCCTACACTAGGCTGGGTCACTGATACTCCTCAGGAGCCCACTCT
ATGATTGGGAGAGATAACCCCAGGTACAAAGTATGCCTATCTGTCTCAACACCATGGGGCAGAAGATACTCCACTAACCACCC
ATGACAGAAAGTTAGCCTTGGCTGTGTCTCCATTAATAGAACACCTCAGAAGACCAATGTGAAATTGCCTAACCCACTCACAC
CCACCCTGATCTCCAGTTCAAAATGCAGAAAACATAATGCAGTTGTCCAAAAGATGCCCCAACCACACACACACACACACACA
CACACACACACACACACACACACACACACACACACACACACCATCAAGGAGCCTCTGTAAGGAGTCACCACCCAATAACACTG
CCTCTTTGGGCTCATATCCTGGACATTCTTCATATTCATATCCATTTGGGGCCTAGGCTTTAGATATCCCCAAGGGCTCATCT
TTACAGGGATCAGAGATCCCAATAAATGCCCTGGTCCCACAGCCTCCCTCAGGTATCTGTCTGTTTATCTCTTGGTACCAAGA
CCCAACATTGCTGGCAGGGGTAGGACAAGCAACGCACGGGAACTCTGATCAAAGAAAGTCATGAGATGCCTGAGTCCTTCAGG
AAGTAAGGAGGGACAACCTCTGGTATCCCTGTTCTTATTGCTAAAGCCCAAGAGACAGGGAGACCTGCTCTAAATTCTCAGTC
TAAACAGCACCGATGGCACCACCTGCTCAGGGAAAGTCCAGAGCACACCAATATCATTTTGCCACAGTTCCTGAGTCTGCCTT
TACCCAGGTCCATACATTGCATCTGTCTTGCTTGCTCTGCTGCCCCAGGGCTCCTGGAACAAAGGCTCCAAATTAGTGTGTCC
TACAGCTTGGCCTGTTCTGTGCCTCCGTCTAGCTTGAGCTATTAGGGGACCAGTCAATACTCGCTAAGATTCTCCAGAACCAT
CAGGGCACCCCAACCCTTATGCAAATG

Mouse C mu exon M1 et M2

CTCAGTCACCCCAAGACTTGGCTTGACCCTCCCTCTCTGTGTCCCTTCATAGAGGGGGAGGTGAATGCTGAGGAGGAAGGCTT
TGAGAACCTGTGGACCACTGCCTCCACCTTCATCGTCCTCTTCCTCCTGAGCCTCTTCTACAGCACCACCGTCACCCTGTTCA
AGGTAGTATGGTTGTGGGGCTGAGGACACAGGGCTGGGACAGGGAGTCACCAGTCCTCACTGCCTCTACCTCTACTCCCTACA
AGTGGACAGCAATTCACACTGTCTCTGTCACCTGCAGGTGAAATGACTCTCAGCATGGAAGGACAGCAGAGACCAAGAGATCC
TCCCACAGGGACACTACCTCTGGGCCTGGGATACCTGACTGTATGACTAGTAAACTTATTCTTACGTCTTTCCTGTGTTGCCC
TCCAGCTTTTATCTCTGAGATGGTCTTCTTTCTAGACTGACCAAAGACTTTTTGTCAACTTGTACAATCTGAAGCAATGTCTG
GCCCACAGACAGCTGAGCTGTAAACAAATGTCACATGGAAATAAATACTTTATCTTGTGAACTCACTTTATTGTGAAGGAAT
TTGTTTTGTTTTTCAAACCTTTCCTGCGGTGTTGACAGCCCAAGGATTATCTGAATAGAGCTTAGGAACTGGAAATGGAACAG
TGCAGTCTGATGGTACTTAAGGGAGAAAGAGGGAAAGGAGGTGTGGAAGAAGAAAAAAGAGAAGCAGAGGGGGAGGGGAGAAG
GGAGAGGGAGAGGGAGAGGGAGAGGGAGAGGGAGAGGGAGAGGGAGAGAGAGAGAGAGAGAGAGAGAGAGAGAGAGAGAGCATGC

FIGURE 2 (Continued)

ACTCTAACAGCAAAGTACAACACAGGCAGCCAATGGATAACACTCTGGTTATCTACCCTGATGGAAGAAGGGAAGTAGGGCAG
AGAAAATTCCAGGCCTAATCTCCCAAAAGCAACAGAACCTGGAAACTAGCCTCTAGCCTTAGGTCTCTGCTCTGTCCCCAGCC
CACCATCTTGGGCTGGTGTTGCTTCAAGCTAGTAATTTAGGTCTTATCCCAAAGCTTTGTGGTATGTGGGTGTGCCTTTGGGG
AGTTGGCTGAGATTTTGAAGATGTTTGTACCTCTCCCACAACATGACAAGCCCTAGGGGTTAGTCAATAACTCAAATTCTCTG
TCTATGACA
ACTGCTGTATGACTATATGAAGAAATGGGATAAAGATGCTATAGTCACTCGAG*GGGGGCCCGGTACCCAGCTTTTGT*

*Cloning vector*

*TCCCTTTAGTGAGGGTTAATTGCGCGCTTGGCGTAATCATGGTCATAGCTGTTTCCTGTGTGAAATTGTTATCCGCTCACAAT*
*TCCACACAACATACGAGCCGGAAGCATAAAGTGTAAAGCCTGGGGTGCCTAATGAGTGAGCTAACTCACATTAATTGCGTTGC*
*GCTCACTGCCCGCTTTCCAGTCGGGAAACCTGTCGTGCCAGCTGCATTAATGAATCGGCCAACGCGCGGGGAGAGGCGGTTTG*
*CGTATTGGGCGCTCTTCCGCTTCCTCGCTCACTGACTCGCTGCGCTCGGTCGTTCGGCTGCGGCGAGCGGTATCAGCTCACTC*
*AAAGGCGGTAATACGGTTATCCACAGAATCAGGGGATAACGCAGGAAAGAACATGTGAGCAAAAGGCCAGCAAAAGGCCAGGA*
*ACCGTAAAAAGGCCGCGTTGCTGGCGTTTTTCCATAGGCTCCGCCCCCCTGACGAGCATCACAAAAATCGACGCTCAAGTCAG*
*AGGTGGCGAAACCCGACAGGACTATAAAGATACCAGGCGTTTCCCCCTGGAAGCTCCCTCGTGCGCTCTCCTGTTCCGACCCT*
*GCCGCTTACCGGATACCTGTCCGCCTTTCTCCCTTCGGGAAGCGTGGCGCTTTCTCATAGCTCACGCTGTAGGTATCTCAGTT*
*CGGTGTAGGTCGTTCGCTCCAAGCTGGGCTGTGTGCACGAACCCCCCGTTCAGCCCGACCGCTGCGCCTTATCCGGTAACTAT*
*CGTCTTGAGTCCAACCCGGTAAGACACGACTTATCGCCACTGGCAGCAGCCACTGGTAACAGGATTAGCAGAGCGAGGTATGT*
*AGGCGGTGCTACAGAGTTCTTGAAGTGGTGGCCTAACTACGGCTACACTAGAAGGACAGTATTTGGTATCTGCGCTCTGCTGA*
*AGCCAGTTACCTTCGGAAAAAGAGTTGGTAGCTCTTGATCCGGCAAACAAACCACCGCTGGTAGCGGTGGTTTTTTTGTTTGC*
*AAGCAGCAGATTACGCGCAGAAAAAAAGGATCTCAAGAAGATCCTTTGATCTTTTCTACGGGGTCTGACGCTCAGTGGAACGA*
*AAACTCACGTTAAGGGATTTTGGTCATGAGATTATCAAAAAGGATCTTCACCTAGATCCTTTTAAATTAAAAATGAAGTTTTA*
*AATCAATCTAAAGTATATATGAGTAAACTTGGTCTGACAGTTACCAATGCTTAATCAGTGAGGCACCTATCTCAGCGATCTGT*
*CTATTTCGTTCATCCATAGTTGCCTGACTCCCCGTCGTGTAGATAACTACGATACGGGAGGGCTTACCATCTGGCCCCAGTGC*
*TGCAATGATACCGCGAGACCCACGCTCACCGGCTCCAGATTTATCAGCAATAAACCAGCCAGCCGGAAGGGCCGAGCGCAGAA*
*GTGGTCCTGCAACTTTATCCGCCTCCATCCAGTCTATTAATTGTTGCCGGGAAGCTAGAGTAAGTAGTTCGCCAGTTAATAGT*
*TTGCGCAACGTTGTTGCCATTGCTACAGGCATCGTGGTGTCACGCTCGTCGTTTGGTATGGCTTCATTCAGCTCCGGTTCCCA*
*ACGATCAAGGCGAGTTACATGATCCCCCATGTTGTGCAAAAAAGCGGTTAGCTCCTTCGGTCCTCCGATCGTTGTCAGAAGTA*
*AGTTGGCCGCAGTGTTATCACTCATGGTTATGGCAGCACTGCATAATTCTCTTACTGTCATGCCATCCGTAAGATGCTTTTCT*
*GTGACTGGTGAGTACTCAACCAAGTCATTCTGAGAATAGTGTATGCGGCGACCGAGTTGCTCTTGCCCGGCGTCAATACGGGA*
*TAATACCGCGCCACATAGCAGAACTTTAAAAGTGCTCATCATTGGAAAACGTTCTTCGGGGCGAAAACTCTCAAGGATCTTAC*
*CGCTGTTGAGATCCAGTTCGATGTAACCCACTCGTGCACCCAACTGATCTTCAGCATCTTTTACTTTCACCAGCGTTTCTGGG*
*TGAGCAAAAACAGGAAGGCAAAATGCCGCAAAAAAGGGAATAAGGGCGACACGGAAATGTTGAATACTCATACTCTTCCTTTT*
*TCAATATTATTGAAGCATTTATCAGGGTTATTGTCTCATGAGCGGATACATATTTGAATGTATTTAGAAAAATAAACAAATAG*
*GGGTTCCGCGCACATTTCCCCGAAAAGTGCCACCTGACGCGCCCTGTAGCGGCGCATTAAGCGCGGCGGGTGTGGTGGTTACG*
*CGCAGCGTGACCGCTACACTTGCCAGCGCCCTAGCGCCCGCTCCTTTCGCTTTCTTCCCTTCCTTTCTCGCCACGTTCGCCGG*
*CTTTCCCCGTCAAGCTCTAAATCGGGGGCTCCCTTTAGGGTTCCGATTTAGTGCTTTACGGCACCTCGACCCCAAAAAACTTG*
*ATTAGGGTGATGGTTCACGTAGTGGGCCATCGCCCTGATAGACGGTTTTTCGCCCTTTGACGTTGGAGTCCACGTTCTTTAAT*
*AGTGGACTCTTGTTCCAAACTGGAACAACACTCAACCCTATCTCGGTCTATTCTTTTGATTTATAAGGGATTTTGCCGATTTC*
*GGCCTATTGGTTAAAAAATGAGCTGATTTAACAAAAATTTAACGCGAATTTTAACAAAATATTAACGCTTACAATTTCCATTC*
*GCCATTCAGGCTGCGCAACTGTTGGGAAGGGCGATCGGTGCGGGCCTCTTCGCTATTACGCCAGCTGGCGAAAGGGGGATGTG*
*CTGCAAGGCGATTAAGTTGGGTAACGCCAGGGTTTTCCCAGTCACGACGTTGTAAAACGACGGCCAGTG*

FIGURE 2 (Continued)

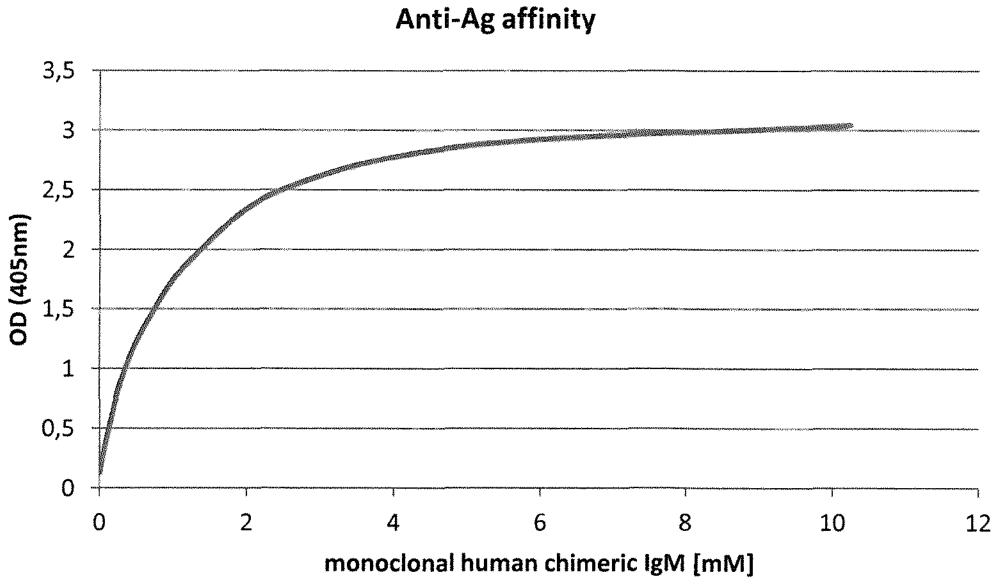
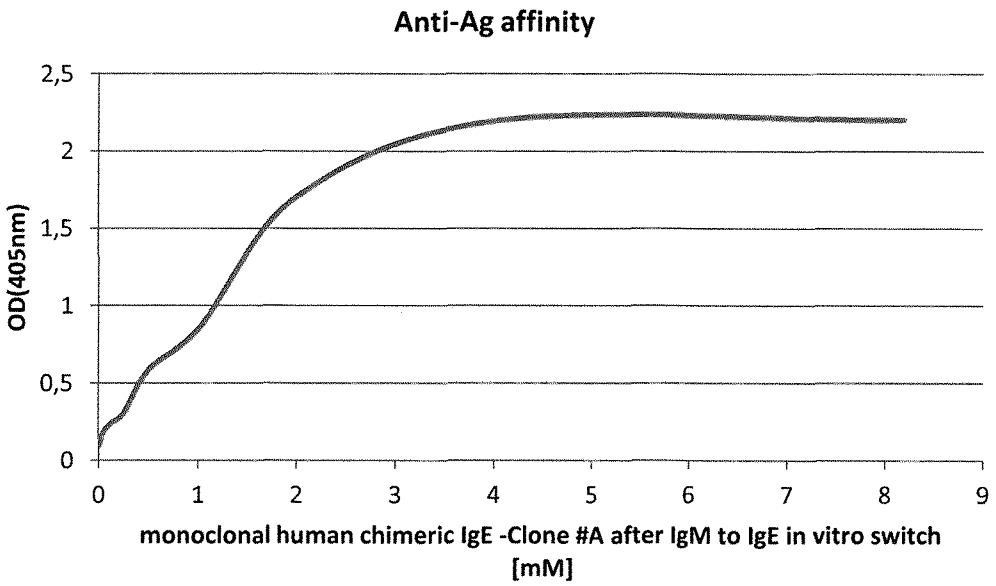
FIGURE 7

SEQUENCE LISTING

```
<160> NUMBER OF SEQ ID NOS: 10

<210> SEQ ID NO 1
<211> LENGTH: 3665
<212> TYPE: DNA
<213> ORGANISM: artificial sequence
<220> FEATURE:
<223> OTHER INFORMATION: synthetic polynucleotide (mouse Smu deletion)

<400> SEQUENCE: 1

taaaagaaaa atgttgcctg ttaaccaata atcatagagc tcatggtact ttgaggaaat      60

cttagaaagc gtgtatacaa ttgtctggaa ttatttcagt taagtgtatt agttgaggta     120

ctgatgctgt ctctacttca gttatacatg tgggtttgaa ttttgaatct attctggctc     180

ttcttaagca gaaaatttag ataaaatgga tacctcagtg gtttttaatg gtgggtttaa     240

tatagaagga atttaaattg gaagctaatt tagaatcagt aaggagggac ccaggctaag     300

aaggcaatcc tgggattctg gaagaaaaga tgtttttagt ttttatagaa aacactacta     360

cattcttgat ctacaactca atgtggttta atgaatttga agttgccagt aaatgtactt     420

cctggttgtt aaagaatggt atcaaaggac agtgcttaga tccgaggtga gtgtgagagg     480

acaggggctg gggtatggat acgcagaagg aaggccacag ctgtacagaa ttgagaaaga     540

atagagacct gcagttgagg ccagcaggtc ggctggacta actctccagc cacagtaatg     600

acccagacag agaaagccag actcataaag cttgctgagc aaaattaagg gaacaaggtt     660

gagagcccta gtaagcgagg ctctaaaaag cacagctgag ctgagatggg tgggcttctc     720
```

-continued tgagtgcttc taaaatgcgc taaactgagg tgattactct gaggtaagca aagctgggct 780
tgagccaaaa tgaagtagac tgtaatgaac tggaatgagc tgggccgcta agctaaacta 840
ggctggctta accgagatga gccaaactgg aatgaacttc attaatctag gttgaataga 900
gctaaactct actgcctaca ctggactgtt ctgagctgag atgagctggg gtgagctcag 960
ctatgctacg ctgtgttggg gtgagctgat ctgaaatgag atactctgga gtagctgaga 1020
tggggtgaga tggggtgagc tgagctgggc tgagctagac tgagctgagc tagggtgagc 1080
tgagctgggt gagctgagct aagctggggt gagctgagct gagcttggct gagctagggt 1140
gagctgggct gagctggggt gagctgagct gagctggggt aagctgggat gagctggggt 1200
gagctgagct gagctggagt gagctgagct gggctgagct ggggtgagct gggctgagct 1260
gggctgagct gggctgagct ggggtgagct gagctggggt gagctgagct gagctggggt 1320
gagctgagct gagctggggt gagctggggt gagctgagct ggggtgagct gagctgagct 1380
ggggtgagct gagctggggt gagctgagct gagctggggt gagctgagct gagctgagct 1440
gagctgagct ggggtgagct gagctgagct gagctggggt gagctggggt gagctgagct 1500
gagctggagt gagctgagct gggctgagct ggggtgagct gggctgagct ggggtgagct 1560
gagctgagct gagctgagct ggggtgagct gagctgagct ggggtgagct gagctggggt 1620
gagctgggct gagctgagct gagctgagct gagctgagct gagctgagct gagctgagct 1680
gagctgagct gagctgagct gagctgagct gagctggggt gagctgagct gagctgggct 1740
crgagctggg gtgagctggg ctgagctggg ctgagctggg ctgagctggg gtgagctgag 1800
ctsmggggtg agctgagctg agctgggctg agctgagctg agctggggtg agctgagctg 1860
agctggggtg agctgagctg agctgagctg gggtgagctg agctgggctg agcagggctg 1920
agctggggtg agctgagctg agctggggtg agctgggctg agctgggctg agctgagctg 1980
agctgggctg agctgggctg agctgggctg agctgggctg agctgggctg agctggggtg 2040
agctgagctg agctggggtg agctggggtg agctgagctg gggtgagctg agctggggtg 2100
agctgagctg agctggggtg agctgagctg gggtgagctg agctgagctg gggtgagctg 2160
agctgagctg gggtgagctg agctagggtg aactgggctg ggtgagctgg agtgagctga 2220
gctgaggtga actggggtga gccgggatgt tttgagttga gctggggtaa gatgagctga 2280
actggggtaa actgggatga gctgtggtga gcggagctgg attgaactga gctgtgtgag 2340
ctgagctggg gtcagctgag caagagtgag tagagctggc tggccagaac cagaatcaat 2400
taggctaagt gagccagatt gtgctgggat cagctgtact cagatgagct gggatgaggt 2460
aggctgggat gagctgggct agctgacatg gattatgtga ggctgagcta gcatgggctg 2520
gcctagctga tgagctaagc ttgaatgagc ggggctgagc tggactcaga tgtgctagac 2580
tgagctgtac tggatgatct ggtgtagggt gatctggact caactgggct ggctgatggg 2640
atgcgccagg ttgaactagg ctcagataag ttaggctgag tagggcctgg ttgagatggt 2700
tcgggatgag ctgggaaaag atggactcgg accatgaact gggctgagct gggttgggag 2760
accatgaatt gagctgaact gagtgcagct gggataaact gggttgagct aagaatagac 2820
tacctgaatt gtgccaaact cggctgggat caattggaaa ttatcaggat ttagatgagc 2880
cggactaaac tatgctgagc tggactggtt ggatgtgttg aactggcctg ctgctgggct 2940
ggcatagctg agttgaactt aaatgaggaa ggctgagcaa ggctagcctg cttgcataga 3000
gctgaacttt agcctagcct gagctggacc agcctgagct gagtaggtct aaactgagtt 3060
aaaaatcaac agggataatt taacagctaa tttaacaagc ctgaggtctg agattgaatg 3120
agcagagctg ggatgaactg aatgagtttc accaggcctg gaccagttag gctaggacct 3180
cgttctatag aggcagactg tgtgctacag tggagtttca agatgattcc atgagtcctc 3240 cccgcccccca acataaccca ccttcctcct accctacacg cctgtctggt gtgtaaatcc 3300
cagctttgtg tgctgataca gaagcctgag cccctccccc acctccacct acctattact 3360
ttgggatgag aatagttctc ccagccagtg tctcagaggg aagccaagca ggacaggccc 3420
aaggctactt gagaagccag gatctaggcc tctccctgag aacgggtgtt catgccccta 3480
gagttggctg aagggccaga tccacctact ctagaggcat ctctccctgt ctgtgaaggc 3540
ttccaaagtc acgttcctgt ggctagaagg cagctccata gccctgctgc agtttcgtcc 3600
tgtataccag gttcacctac taccatatct agccctgcct gccttaagag tagcaacaag 3660
gaaat 3665

<210> SEQ ID NO 2
<211> LENGTH: 4492
<212> TYPE: DNA
<213> ORGANISM: artificial sequence
<220> FEATURE:
<223> OTHER INFORMATION: synthetic polynucleotide (human Cmu gene)

<400> SEQUENCE: 2
tcagggagtg catccgcccc aacccttttc cccctcgtct cctgtgagaa ttccccgtcg 60
gatacgagca gcgtggccgt tggctgcctc gcacaggact tccttcccga ctccatcact 120
ttctcctgga aatacaagaa caactctgac atcagcagca cccggggctt cccatcagtc 180
ctgagagggg gcaagtacgc agccacctca caggtgctgc tgccttccaa ggacgtcatg 240
cagggcacag acgaacacgt ggtgtgcaaa gtccagcacc ccaacggcaa caaagaaaag 300
aacgtgcctc ttccaggtga gggccgggcc cagccaccgg gacagagagg gagccgaagg 360
ggggcgggag tggcgggcac cgggctgaca cgtgtccctc actgcagtga ttgctgagct 420
gcctcccaaa gtgagcgtct tcgtcccacc ccgcgacggc ttcttcggca acccccgcaa 480
gtccaagctc atctgccagg ccacgggttt cagtccccgg cagattcagg tgtcctggct 540
gcgcgagggg aagcaggtgg ggtctggcgt caccacggac caggtgcagg ctgaggccaa 600
agagtctggg cccacgacct acaaggtgac cagcacactg accatcaaag agagcgactg 660
gctcagccag agcatgttca cctgccgcgt ggatcacagg ggcctgacct tccagcagaa 720
tgcgtcctcc atgtgtgtcc ccggtgagtg acctgtcccc aggggcagca cccaccgaca 780
cacaggggtc cactcgggtc tggcattcgc caccccggat gcagccatct actccctgag 840
ccttggcttc ccagagcggc caagggcagg ggctcgggcg gcaggacccc tgggctcggc 900
agaggcagtt gctactcttt gggtgggaac catgcctccg cccacatcca cacctgcccc 960
acctctgact cccttctctt gactccagat caagacacag ccatccgggt cttcgccatc 1020
cccccatcct ttgccagcat cttcctcacc aagtccacca agttgacctg cctggtcaca 1080
gacctgacca cctatgacag cgtgaccatc tcctggaccc gccagaatgg cgaagctgtg 1140
aaaacccaca ccaacatctc cgagagccac cccaatgcca ctttcagcgc cgtgggtgag 1200
gccagcatct gcgaggatga ctggaattcc ggggagaggt tcacgtgcac cgtgacccac 1260
acagacctgc cctcgccact gaagcagacc atctcccggc ccaagggtag gccccactct 1320
tgcccctctt ctgcactcct gcaactcctt gcctctgggg gcatggtgga aagcacccct 1380
cactcccccg ttgtctgggc aactggggaa aaggggactc aaccccagcc cacaggctgg 1440

-continued tccccccact gccccgccct caccaccatc tctgttcaca ggggtggccc tgcacaggcc 1500
cgatgtctac ttgctgccac cagcccggga gcagctgaac ctgcgggagt cggccaccat 1560
cacgtgcctg gtgacgggct tctctcccgc ggacgtcttc gtgcagtgga tgcagagggg 1620
gcagcccttg tccccggaga agtatgtgac cagcgcccca atgcctgagc cccaggcccc 1680
aggccggtac ttcgcccaca gcatcctgac cgtgtccgaa gaggaatgga acacggggga 1740
gacctacacc tgcgtggtgg cccatgaggc cctgcccaac agggtcaccg agaggaccgt 1800
ggacaagtcc accggtaaac ccaccctgta caacgtgtcc ctggtcatgt ccgacacagc 1860
tggcacctgc tactgaccct gctggcctgc ccacaggctc ggggcggctg gccgctctgt 1920
gtgtgcatgc aaactaaccg tgtcaacggg gtgagatgtt gcatcttata aaattagaaa 1980
taaaaagatc cattcaaaag atactggtcc tgagtgcacg atgctctggc ctactggggc 2040
ggcggctgtg ctgcacccac cctgcgcctc ccctgcagaa caccttcctc cacagccccc 2100
acccctgcct cacccacctg cgtgcctcag tggcttctag aaacccctga attccctgca 2160
gctgctcaca gcaggctgac ctcagacttg ccattcctcc tactgcttcc agaaagaaag 2220
ctgaaagcaa ggccacacgt atacaggcag cacacaggca tgtgtggata cacatggaca 2280
gacacggaca cacacaaaca catggacaca cagagacgtg ctaacccatg ggcacacaca 2340
tacacagaca tggacccaca cacaaacata tgtggacaca catgtacaaa catgcacagg 2400
cacacaaaga gaacactgac tacaggcaca cacacacacg ggcacacaca tggatatgtg 2460
cacacatgga cacatacatg tgcaggacat gcacacacac agacacacta gcacagaggc 2520
atacacacac agacacacac attcacaaac acacatgtgc atgcaaacac acacacatgt 2580
acagacacga gtacatggac acatgcacac ccagagacac actgacacag acacacagga 2640
gcatgtgata cactaacacg tggacacaca cgtctaccca caggcacaca acagatggac 2700
acgcgtacac agacatgcac acacccacag gcacaacacg tgcgcatgcc ggccggcccc 2760
cgcccacatt ctcccagggc cctgccggat actctgtccc tgcagcagtt tgctccctgc 2820
gctgtgctgg ccccggggct ttgggcccag gctctgcttg tccttctgtc tctgcttgga 2880
ggtgctgcca tggcacccag cttgggctct gcctggggag cggaggcccc agggatagca 2940
tgtgacccct gctgaggcca ggctcctgat gaaggcagca gatagccccc acacccaccg 3000
gtgagcagaa ccagagcctg tgccatgtgc tgagagcagg cagtgactaa gcatatgggc 3060
ccagagggca gagtggctgc cctgggcagc tgctcctctt agcgggaggc ctcaggagat 3120
gagctagagc aagtctgccc ctgcaaatac cacctgctcc ccaacccaca gcagggagca 3180
ggcgaggtca gacagcagca gcccgggaag gaccgagccc cagcagggaa ggcagggccc 3240
gagtgaggtc tccacaccca acgcacagtg ctgtctctaa ctggggccac ctccgagtcc 3300
ccgccacact cttggccctt tggagtcctg ggctccaggt gtctcccaag ggcccatctg 3360
tgcaggggat gcaacccccc gaatgtcctc atcccactgt ggagctcagg tctctgtctg 3420
ctccctgggt cctggcaggg taggacaagt ccgccaggat gtccccatgc agactctgct 3480
ccaagaggga gctggagagt cagggccttg gtgagggagt caggatcggg ttccccccag 3540
ctcagtcctc ccacctgcca gcccccacag cacagggcag ggccacaccc cctgcttccc 3600
cctccaggag agtcaggaca tgctggccgc tgctccgctg gggccccgcc ctccagcccc 3660
caccttggtc tgtgtgctgc atcccccacg ctctctctgc caccccagga ctctgaggaa 3720
aagacctcag agtcccagcc ctgcccagtc tcggcctgtg cccccgctgc atcaggcttt 3780

-continued

```
caggggccca gcccatgccc tgggcagtgc ccgagccccc ctgcacttgc tctccccacc   3840

cctgggtgca gcacagccta ggggccaagg gtgggcctag aggatgggcc ccggggggc   3900

tttgctgggt gccaccccag cctgacccta ttcccccgtg ctgtgtctcc tgcagagggg   3960

gaggtgagcg ccgacgagga gggctttgag aacctgtggg ccaccgcctc caccttcatc   4020

gtcctcttcc tcctgagcct cttctacagt accaccgtca ccttgttcaa ggtagcacgg   4080

ctgtggcaca gggaggaggg tgcagggcga gtgtggggcc cagggagcag cctgggctgg   4140

acgtctagcc cggaggcccc cacaccaccc cactgggtca tctctgcccc ggctcccttc   4200

ccgaccacgg ggaaagcatt tcacactgtc tctgttgcct gtaggtgaaa tgatcccaac   4260

agaagaacat cggagaccag agagaggaac tcaaaggggc gctgcctccg ggtctggggt   4320

cctggcctgc gtggcctgtt ggcacgtgtt tctcttcccc gcccggcctc cagttgtgtg   4380

ctctcacaca ggcttctttc tcgaccggca ggggctggct ggcttgcagg ccacgaggtg   4440

gggctctacc ccacactgct ttgctgtgta tacgcttgtt gcctgaaata aa           4492
```

<210> SEQ ID NO 3
<211> LENGTH: 4492
<212> TYPE: DNA
<213> ORGANISM: artificial sequence
<220> FEATURE:
<223> OTHER INFORMATION: syntheric polynucleotide (human Cepsilon gene)

<400> SEQUENCE: 3

```
tcagggagtg catccgcccc aacccttttc cccctcgtct cctgtgagaa ttccccgtcg     60

gatacgagca gcgtggccgt tggctgcctc gcacaggact tccttcccga ctccatcact    120

ttctcctgga aatacaagaa caactctgac atcagcagca cccggggctt cccatcagtc    180

ctgagagggg gcaagtacgc agccacctca caggtgctgc tgccttccaa ggacgtcatg    240

cagggcacag acgaacacgt ggtgtgcaaa gtccagcacc ccaacggcaa caaagaaaag    300

aacgtgcctc ttccaggtga gggccgggcc cagccaccgg gacagagagg gagccgaagg    360

ggggcgggag tggcgggcac cggctgaca cgtgtccctc actgcagtga ttgctgagct    420

gcctcccaaa gtgagcgtct tcgtcccacc ccgcgacggc ttcttcggca acccccgcaa    480

gtccaagctc atctgccagg ccacgggttt cagtccccgg cagattcagg tgtcctggct    540

gcgcgagggg aagcaggtgg ggtctggcgt caccacggac caggtgcagg ctgaggccaa    600

agagtctggg cccacgacct acaaggtgac cagcacactg accatcaaag agagcgactg    660

gctcagccag agcatgttca cctgccgcgt ggatcacagg ggcctgacct tccagcagaa    720

tgcgtcctcc atgtgtgtcc ccggtgagtg acctgtcccc aggggcagca cccaccgaca    780

cacaggggtc cactcgggtc tggcattcgc caccccggat gcagccatct actccctgag    840

ccttggcttc ccagagcggc caagggcagg ggctcgggcg gcaggacccc tgggctcggc    900

agaggcagtt gctactcttt gggtgggaac catgcctccg cccacatcca cacctgcccc    960

acctctgact cccttctctt gactccagat caagacacag ccatccgggt cttcgccatc   1020

cccccatcct ttgccagcat cttcctcacc aagtccacca agttgacctg cctggtcaca   1080

gacctgacca cctatgacag cgtgaccatc tcctggaccc gccagaatgg cgaagctgtg   1140

aaaacccaca ccaacatctc cgagagccac cccaatgcca ctttcagcgc cgtgggtgag   1200

gccagcatct gcgaggatga ctggaattcc ggggagaggt tcacgtgcac cgtgacccac   1260

acagacctgc cctcgccact gaagcagacc atctcccggc ccaagggtag gccccactct   1320

tgcccctctt ctgcactcct gcaactcctt gcctctgggg gcatggtgga aagcacccct   1380
```

-continued

```
cactcccccg ttgtctgggc aactggggaa aaggggactc aaccccagcc cacaggctgg   1440
tccccccact gccccgccct caccaccatc tctgttcaca ggggtggccc tgcacaggcc   1500
cgatgtctac ttgctgccac cagcccggga gcagctgaac ctgcgggagt cggccaccat   1560
cacgtgcctg gtgacgggct tctctcccgc ggacgtcttc gtgcagtgga tgcagagggg   1620
gcagccccttg tccccggaga agtatgtgac cagcgcccca atgcctgagc cccaggcccc   1680
aggccggtac ttcgcccaca gcatcctgac cgtgtccgaa gaggaatgga acacggggga   1740
gacctacacc tgcgtggtgg cccatgaggc cctgcccaac agggtcaccg agaggaccgt   1800
ggacaagtcc accggtaaac ccaccctgta caacgtgtcc ctggtcatgt ccgacacagc   1860
tggcacctgc tactgaccct gctggcctgc ccacaggctc ggggcggctg gccgctctgt   1920
gtgtgcatgc aaactaaccg tgtcaacggg gtgagatgtt gcatcttata aaattagaaa   1980
taaaaagatc cattcaaaag atactggtcc tgagtgcacg atgctctggc ctactggggc   2040
ggcggctgtg ctgcacccac cctgcgcctc ccctgcagaa caccttcctc cacagccccc   2100
acccctgcct cacccacctg cgtgcctcag tggcttctag aaacccctga attccctgca   2160
gctgctcaca gcaggctgac ctcagacttg ccattcctcc tactgcttcc agaaagaaag   2220
ctgaaagcaa ggccacacgt atacaggcag cacacaggca tgtgtggata cacatggaca   2280
gacacggaca cacacaaaca catggacaca cagagacgtg ctaacccatg ggcacacaca   2340
tacacagaca tggacccaca cacaaacata tgtggacaca catgtacaaa catgcacagg   2400
cacacaaaga gaacactgac tacaggcaca cacacacacg ggcacacaca tggatatgtg   2460
cacacatgga cacatacatg tgcaggacat gcacacacac agacacacta gcacagaggc   2520
atacacacac agacacacac attcacaaac acacatgtgc atgcaaacac acacacatgt   2580
acagacacga gtacatggac acatgcacac ccagagacac actgacacag acacacagga   2640
gcatgtgata cactaacacg tggacacaca cgtctaccca caggcacaca acagatggac   2700
acgcgtacac agacatgcac acacccacag gcacaacacg tgcgcatgcc ggccggcccc   2760
cgcccacatt ctcccagggc cctgccggat actctgtccc tgcagcagtt tgctccctgc   2820
gctgtgctgg ccccggggct ttgggcccag gctctgcttg tccttctgtc tctgcttgga   2880
ggtgctgcca tggcacccag cttgggctct gcctggggag cggaggcccc agggatagca   2940
tgtgacccct gctgaggcca ggctcctgat gaaggcagca gatagccccc acacccaccg   3000
gtgagcagaa ccagagcctg tgccatgtgc tgagagcagg cagtgactaa gcatatgggc   3060
ccagagggca gagtggctgc cctgggcagc tgctcctctt agcgggaggc ctcaggagat   3120
gagctagagc aagtctgccc ctgcaaatac cacctgctcc ccaacccaca gcagggagca   3180
ggcgaggtca gacagcagca gcccgggaag gaccgagccc cagcagggaa ggcagggccc   3240
gagtgaggtc tccacaccca acgcacagtg ctgtctctaa ctggggccac ctccgagtcc   3300
ccgccacact cttggccctt tggagtcctg ggctccaggt gtctcccaag ggcccatctg   3360
tgcaggggat gcaacccccc gaatgtcctc atcccactgt ggagctcagg tctctgtctg   3420
ctccctgggt cctggcaggg taggacaagt ccgccaggat gtccccatgc agactctgct   3480
ccaagaggga gctggagagt cagggccttg gtgagggagt caggatcggg ttccccccag   3540
ctcagtcctc ccacctgcca gcccccacag cacagggcag ggccacaccc cctgcttccc   3600
cctccaggag agtcaggaca tgctggccgc tgctccgctg gggccccgcc ctccagcccc   3660
caccttggtc tgtgtgctgc atcccccacg ctctctctgc caccccagga ctctgaggaa   3720
```

-continued

```
aagacctcag agtcccagcc ctgcccagtc tcggcctgtg cccccgctgc atcaggcttt   3780

caggggccca gcccatgccc tgggcagtgc ccgagccccc ctgcacttgc tctccccacc   3840

cctgggtgca gcacagccta ggggccaagg gtgggcctag aggatgggcc ccggggggc   3900

tttgctgggt gccaccccag cctgacccta ttccccgtg ctgtgtctcc tgcagagggg   3960

gaggtgagcg ccgacgagga gggctttgag aacctgtggg ccaccgcctc caccttcatc   4020

gtcctcttcc tcctgagcct cttctacagt accaccgtca ccttgttcaa ggtagcacgg   4080

ctgtggcaca gggaggaggg tgcagggcga gtgtggggcc cagggagcag cctgggctgg   4140

acgtctagcc cggaggcccc cacaccaccc cactgggtca tctctgcccc ggctcccttc   4200

ccgaccacgg ggaaagcatt tcacactgtc tctgttgcct gtaggtgaaa tgatcccaac   4260

agaagaacat cggagaccag agagaggaac tcaaaggggc gctgcctccg ggtctggggt   4320

cctggcctgc gtggcctgtt ggcacgtgtt tctcttcccc gcccggcctc cagttgtgtg   4380

ctctcacaca ggcttctttc tcgaccggca ggggctggct ggcttgcagg ccacgaggtg   4440

gggctctacc ccacactgct ttgctgtgta tacgcttgtt gcctgaaata aa           4492
```

<210> SEQ ID NO 4
<211> LENGTH: 894
<212> TYPE: DNA
<213> ORGANISM: artificial sequence
<220> FEATURE:
<223> OTHER INFORMATION: synthetic polynucleotide (neomycin resistance gene)

<400> SEQUENCE: 4

```
atgggatcgg ccattgaaca agatggattg cacgcaggtt ctccggccgc ttgggtggag     60

aggctattcg gctatgactg ggcacaacag acaatcggct gctctgatgc cgccgtgttc    120

cggctgtcag cgcaggggcg cccggttctt tttgtcaaga ccgacctgtc cggtgccctg    180

aatgaactgc aggacgaggc agcgcggcta tcgtggctgg ccacgacggg cgttccttgc    240

gcagctgtgc tcgacgttgt cactgaagcg ggaagggact ggctgctatt gggcgaagtg    300

ccggggcagg atctcctgtc atctcacctt gctcctgccg agaaagtatc catcatggct    360

gatgcaatgc ggcggctgca tacgcttgat ccggctacct gcccattcga ccaccaagcg    420

aaacatcgca tcgagcgagc acgtactcgg atggaagccg gtcttgtcga tcaggatgat    480

ctggacgaag agcatcaggg gctcgcgcca gccgaactgt tcgccaggct caaggcgcgc    540

atgcccgacg gcgaggatct cgtcgtgacc catggcgatg cctgcttgcc gaatatcatg    600

gtggaaaatg gccgcttttc tggattcatc gactgtggcc ggctgggtgt ggcggaccgc    660

tatcaggaca tagcgttggc tacccgtgat attgctgaag agcttggcgg cgaatgggct    720

gaccgcttcc tcgtgcttta cggtatcgcc gctcccgatt cgcagcgcat cgccttctat    780

cgccttcttg acgagttctt ctgaggggat cggcaataaa aagacagaat aaaacgcacg    840

ggtgttgggt cgtttgttcg gatcagcttc cgatcatatt caataaccct taat          894
```

<210> SEQ ID NO 5
<211> LENGTH: 34
<212> TYPE: DNA
<213> ORGANISM: artificial sequence
<220> FEATURE:
<223> OTHER INFORMATION: synthetic oligonucleotide (loxP)

<400> SEQUENCE: 5

```
ataacttcgt ataatgtatg ctatacgaag ttat                                 34
```

<210> SEQ ID NO 6
<211> LENGTH: 15525
<212> TYPE: DNA
<213> ORGANISM: artificial sequence
<220> FEATURE:
<223> OTHER INFORMATION: synthetic polynucleotide (transgenic DNA construct)

<400> SEQUENCE: 6
gaagaggagt ttacgtccag ccttcgaagg gtcctcaggg agtgcatccg ccccaaccct 60
tttccccctc gtctcctgtg agaattcccc gtcggatacg agcagcgtgg ccgttggctg 120
cctcgcacag gacttccttc ccgactccat cactttctcc tggaaataca agaacaactc 180
tgacatcagc agcacccggg gcttcccatc agtcctgaga gggggcaagt acgcagccac 240
ctcacaggtg ctgctgcctt ccaaggacgt catgcagggc acagacgaac acgtggtgtg 300
caaagtccag caccccaacg gcaacaaaga aaagaacgtg cctcttccag gtgagggccg 360
ggcccagcca ccgggacaga gagggagccg aagggggggcg ggagtggcgg gcaccgggct 420
gacacgtgtc cctcactgca gtgattgctg agctgcctcc caaagtgagc gtcttcgtcc 480
caccccgcga cggcttcttc ggcaaccccc gcaagtccaa gctcatctgc caggccacgg 540
gtttcagtcc ccggcagatt caggtgtcct ggctgcgcga ggggaagcag gtggggtctg 600
gcgtcaccac ggaccaggtg caggctgagg ccaaagagtc tgggcccacg acctacaagg 660
tgaccagcac actgaccatc aaagagagcg actggctcag ccagagcatg ttcacctgcc 720
gcgtggatca caggggcctg accttccagc agaatgcgtc ctccatgtgt gtccccggtg 780
agtgacctgt ccccaggggc agcacccacc gacacacagg ggtccactcg ggtctggcat 840
tcgccacccc ggatgcagcc atctactccc tgagccttgg cttcccagag cggccaaggg 900
caggggctcg ggcggcagga cccctgggct cggcagaggc agttgctact ctttgggtgg 960
gaaccatgcc tccgcccaca tccacacctg ccccacctct gactcccttc tcttgactcc 1020
agatcaagac acagccatcc gggtcttcgc catcccccca tcctttgcca gcatcttcct 1080
caccaagtcc accaagttga cctgcctggt cacagacctg accacctatg acagcgtgac 1140
catctcctgg acccgccaga atggcgaagc tgtgaaaacc cacaccaaca tctccgagag 1200
ccaccccaat gccactttca gcgccgtggg tgaggccagc atctgcgagg atgactggaa 1260
ttccggggag aggttcacgt gcaccgtgac ccacacagac ctgccctcgc cactgaagca 1320
gaccatctcc cggcccaagg gtaggcccca ctcttgcccc tcttctgcac tcctgcaact 1380
ccttgcctct gggggcatgg tggaaagcac ccctcactcc cccgttgtct gggcaactgg 1440
ggaaaagggg actcaacccc agcccacagg ctggtccccc cactgccccg ccctcaccac 1500
catctctgtt cacaggggtg gccctgcaca ggcccgatgt ctacttgctg ccaccagccc 1560
gggagcagct gaacctgcgg gagtcggcca ccatcacgtg cctggtgacg ggcttctctc 1620
ccgcggacgt cttcgtgcag tggatgcaga gggggcagcc cttgtccccg gagaagtatg 1680
tgaccagcgc cccaatgcct gagccccagg ccccaggccg gtacttcgcc cacagcatcc 1740
tgaccgtgtc cgaagaggaa tggaacacgg gggagaccta cacctgcgtg gtggcccatg 1800
aggccctgcc caacagggtc accgagagga ccgtggacaa gtccaccggt aaacccaccc 1860
tgtacaacgt gtccctggtc atgtccgaca cagctggcac ctgctactga ccctgctggc 1920
ctgcccacag gctcggggcg gctggccgct ctgtgtgtgc atgcaaacta accgtgtcaa 1980
cggggtgaga tgttgcatct tataaaatta gaaataaaaa gatccattca aaagatactg 2040

-continued

```
gtcctgagtg cacgatgctc tggcctactg gggcggcggc tgtgctgcac ccaccctgcg   2100
cctcccctgc agaacacctt cctccacagc cccccacccct gcctcaccca cctgcgtgcc   2160
tcagtggctt ctagaaaccc ctgaattccc tgcagctgct cacagcaggc tgacctcaga   2220
cttgccattc ctcctactgc ttccagaaag aaagctgaaa gcaaggccac acgtatacag   2280
gcagcacaca ggcatgtgtg gatacacatg gacagacacg gacacacaca aacacatgga   2340
cacacagaga cgtgctaacc catgggcaca cacatacaca gacatggacc cacacacaaa   2400
catatgtgga cacacatgta caaacatgca caggcacaca aagagaacac tgactacagg   2460
cacacacaca cacgggcaca cacatggata tgtgcacaca tggacacata catgtgcagg   2520
acatgcacac acacagacac actagcacag aggcatacac acacagacac acacattcac   2580
aaacacacat gtgcatgcaa acacacacac atgtacagac acgagtacat ggacacatgc   2640
acacccagag acacactgac acagacacac aggagcatgt gatacactaa cacgtggaca   2700
cacacgtcta cccacaggca cacaacagat ggacacgcgt acacagacat gcacacaccc   2760
acaggcacaa cacgtgcgca tgccggccgg cccccgccca cattctccca gggccctgcc   2820
ggatactctg tccctgcagc agtttgctcc ctgcgctgtg ctggccccgg ggctttgggc   2880
ccaggctctg cttgtccttc tgtctctgct tggaggtgct gccatggcac ccagcttggg   2940
ctctgcctgg ggagcggagg ccccagggat agcatgtgac ccctgctgag gccaggctcc   3000
tgatgaaggc agcagatagc cccacaccc accggtgagc agaaccagag cctgtgccat   3060
gtgctgagag caggcagtga ctaagcatat gggcccagag ggcagagtgg ctgccctggg   3120
cagctgctcc tcttagcggg aggcctcagg agatgagcta gagcaagtct gcccctgcaa   3180
ataccacctg ctccccaacc cacagcaggg agcaggcgag gtcagacagc agcagcccgg   3240
gaaggaccga gccccagcag ggaaggcagg gcccgagtga ggtctccaca cccaacgcac   3300
agtgctgtct ctaactgggg ccacctccga gtccccgcca cactcttggc cctttggagt   3360
cctgggctcc aggtgtctcc caagggccca tctgtgcagg ggatgcaacc ccccgaatgt   3420
cctcatccca ctgtggagct caggtctctg tctgctccct gggtcctggc agggtaggac   3480
aagtccgcca ggatgtcccc atgcagactc tgctccaaga gggagctgga gagtcagggc   3540
cttggtgagg gagtcaggat cgggttcccc ccagctcagt cctcccacct gccagccccc   3600
acagcacagg gcagggccac accccctgct tcccctcca ggagagtcag gacatgctgg   3660
ccgctgctcc gctggggccc cgccctccag cccccacctt ggtctgtgtg ctgcatcccc   3720
cacgctctct ctgccaccc aggactctga ggaaaagacc tcagagtccc agccctgccc   3780
agtctcggcc tgtgcccccg ctgcatcagg ctttcagggg cccagcccat gccctgggca   3840
gtgcccgagc cccctgcac ttgctctccc cacccctggg tgcagcacag cctaggggcc   3900
aagggtgggc ctagaggatg ggccccgggg gggctttgct gggtgccacc ccagcctgac   3960
cctattcccc cgtgctgtgt ctcctgcaga gggggaggtg agcgccgacg aggagggctt   4020
tgagaacctg tgggccaccg cctccacctt catcgtcctc ttcctcctga gcctcttcta   4080
cagtaccacc gtcaccttgt tcaaggtagc acggctgtgg cacagggagg agggtgcagg   4140
gcgagtgtgg ggcccaggga gcagcctggg ctggacgtct agcccggagg cccccacacc   4200
accccactgg gtcatctctg ccccggctcc cttcccgacc acggggaaag catttcacac   4260
tgtctctgtt gcctgtaggt gaaatgatcc caacagaaga acatcggaga ccagagagag   4320
gaactcaaag gggcgctgcc tccgggtctg gggtcctggc ctgcgtggcc tgttggcacg   4380
tgtttctctt ccccgcccgg cctccagttg tgtgctctca cacaggcttc tttctcgacc   4440
```

-continued

```
ggcaggggct ggctggcttg caggccacga ggtggggctc taccccacac tgctttgctg   4500
tgtatacgct tgttgcctga aataaatatg cacattttat ccatgaaact gctttctggt   4560
gagggtttgt ttctttttca aaactttcct gctacagggc attcaagcca tcgatgtcga   4620
ggaattccga tcatattcaa taacccttaa tataacttcg tataatgtat gctatacgaa   4680
gttattaggt ctgaagagga gtttacgtcc agccaagcta gcttggctgc aggtcgagca   4740
gtgtggtttt caagaggaag caaaaagcct ctccacccag gcctggaatg tttccaccca   4800
atgtcgagca gtgtggtttt gcaagaggaa gcaaaaagcc tctccaccca ggcctggaat   4860
gtttccaccc aatgtcgagc agtgtggttt tgcaagagga agcaaaaagc ctctccaccc   4920
aggcctggaa tgtttccacc caatgtcgag caaaccccgc ccagcgtctt gtcattggcg   4980
aattcgaaca cgcagatgca gtcggggcgg cgcggtcccc aggtccactt cgcatattaa   5040
ggtgacgcgt gtggcctcga acaccgagcg accctgcagc caatatggga tcggccattg   5100
aacaagatgg attgcacgca ggttctccgg ccgcttgggt ggagaggcta ttcggctatg   5160
actgggcaca acagacaatc ggctgctctg atgccgccgt gttccggctg tcagcgcagg   5220
ggcgcccggt tctttttgtc aagaccgacc tgtccggtgc cctgaatgaa ctgcaggacg   5280
aggcagcgcg gctatcgtgg ctggccacga cgggcgttcc ttgcgcagct gtgctcgacg   5340
ttgtcactga agcgggaagg gactggctgc tattgggcga agtgccgggg caggatctcc   5400
tgtcatctca ccttgctcct gccgagaaag tatccatcat ggctgatgca atgcggcggc   5460
tgcatacgct tgatccggct acctgcccat tcgaccacca agcgaaacat cgcatcgagc   5520
gagcacgtac tcggatggaa gccggtcttg tcgatcagga tgatctggac gaagagcatc   5580
aggggctcgc gccagccgaa ctgttcgcca ggctcaaggc gcgcatgccc gacggcgagg   5640
atctcgtcgt gacccatggc gatgcctgct tgccgaatat catggtggaa aatggccgct   5700
tttctggatt catcgactgt ggccggctgg gtgtggcgga ccgctatcag gacatagcgt   5760
tggctacccg tgatattgct gaagagcttg gcggcgaatg ggctgaccgc ttcctcgtgc   5820
tttacggtat cgccgctccc gattcgcagc gcatcgcctt ctatcgcctt cttgacgagt   5880
tcttctgagg ggatcggcaa taaaaagaca gaataaaacg cacgggtgtt gggtcgtttg   5940
ttcggatcag cttccgatca tattcaataa cccttaatat aacttcgtat aatgtatgct   6000
atacgaagtt attaggtctg aagaggagtt tacgtccagc caagctaact tggcgccccc   6060
actagggtcg aggagcttgg taccgagctc ggatccacta gtaacggccg ccagtgtgct   6120
ggaattcgcc cttgatgaat gagcctggca tctggctccc tgccacgggg tccccagctc   6180
ccccatccag gccccccagg cctgatgggc gctggcctga ggctggcact gactaggttc   6240
tgtcctcaca gcctccacac agagcccatc cgtcttcccc ttgacccgct gctgcaaaaa   6300
cattccctcc aatgccacct ccgtgactct gggctgcctg gccacgggct acttcccgga   6360
gccggtgatg gtgacctggg acacaggctc cctcaacggg acaactatga ccttaccagc   6420
caccaccctc acgctctctg gtcactatgc caccatcagc ttgctgaccg tctcgggtgc   6480
gtgggccaag cagatgttca cctgccgtgt ggcacacact ccatcgtcca cagactgggt   6540
cgacaacaaa accttcagcg gtaagagagg gccaagctca gagaccacag ttcccaggag   6600
tgccaggctg agggctggca gagtgggcag ggttgaggg ggtgggtggg ctcaaacgtg   6660
ggaacaccca gcatgcctgg ggacccgggc caggacgtgg gggcaagagg agggcacaca   6720
gagctcagag agcccaacaa ccctcatgac caccagctct cccccagtct gctccaggga   6780
```

-continued

```
cttcaccccg cccaccgtga agatcttaca gtcgtcctgc gacggcggcg ggcacttccc   6840
cccgaccatc cagctcctgt gcctcgtctc tgggtacacc ccagggacta tcaacatcac   6900
ctggctggag gacgggcagg tcatggacgt ggacttgtcc accgcctcta ccacgcagga   6960
gggtgagctg gcctccacac aaagcgagct caccctcagc cagaagcact ggctgtcaga   7020
ccgcacctac acctgccagg tcacctatca aggtcacacc tttgaggaca gcaccaagaa   7080
gtgtgcaggt acgttcccac ctgccctggt ggccgccacg gaggccagag aagaggggcg   7140
ggtgggcctc acacagccct ccggtgtacc acagattcca acccgagagg ggtgagcgcc   7200
tacctaagcc ggcccagccc gttcgacctg ttcatccgca agtcgcccac gatcacctgt   7260
ctggtggtgg acctggcacc cagcaagggg accgtgaacc tgacctggtc ccgggccagt   7320
gggaagcctg tgaaccactc caccagaaag gaggagaagc agcgcaatgg cacgttaacc   7380
gtcacgtcca ccctgccggt gggcacccga gactggatcg agggggagac ctaccaatgc   7440
agggtgaccc acccccacct gcccagggcc ctcatgcggt ccacgaccaa gaccagcggt   7500
gagccatggg caggccgggg tcgtggggga agggagggag cgagtgagcg gggcccgggc   7560
tgaccccacg tctggccaca ggcccgcgtg ctgccccgga agtctatgcg tttgcgacgc   7620
cggagtggcc ggggagccgg gacaagcgca ccctcgcctg cctgatccag aacttcatgc   7680
ctgaggacat ctcggtgcag tggctgcaca acgaggtgca gctcccggac gcccggcaca   7740
gcacgacgca gccccgcaag accaagggct ccggcttctt cgtcttcagc cgcctggagg   7800
tgaccagggc cgaatgggag cagaaagatg agttcatctg ccgtgcagtc catgaggcag   7860
cgagcccctc acagaccgtc cagcgagcgg tgtctgtaaa tcccggtaaa tgacgtactc   7920
ctgcctccct ccctcccagg gctccatcca gctgtgcagt ggggaggact ggccagacct   7980
tctgtccact gttgcaatga ccccaggaag ctacccccaa taaactgtgc ctgctcagag   8040
ccccaggtac acccattctt gggagcgggc agggctgtgg gcaggtgcat cttggcacag   8100
aggaatgggc cccccaggag gggcagtggg aggaggtggg cagggctgag tccccccagg   8160
agaggtggtg ggaggaggtg ggcaggggtg aggtgccact catccatctg ccttcgtgtc   8220
agggttattt gtcaaacagc atatctgcag ggactcatca cagctacccc gggcctctct   8280
gcccccactc tgggtctacc ccctccaagg agtccaaaga cccaggggag gtcctcaggg   8340
aaggggcaag ggagccccca cagccctccc tcttgggggc ttggcttcta ccccccctgga   8400
caggagcccc tgcaccccca ggtatagatg ggcacacagg cccctccagg tggaaaaaca   8460
gccctaagtg aaaccccccac acagacacac acaacccgac agccctcgcc caagtctgtg   8520
ccactggcgt tcgcctctct gccctgtccc gccttgccga gtcctggccc cagcaccggg   8580
gccggtggag ccgagcccac tcacaccccg cagcctccgc caccctgccc tgtgggcaca   8640
ccaggcccag gtcagagcca ggccccctct cctactgccc cccaccgccc cttggtccat   8700
cctgaatcgg cctccagggg atcgccagcc tcacacaccc ggtctcgccc actcacgcct   8760
cactcaaggc acagctgtgc acacactagg ccccatagca actccacagc accctgtacc   8820
accaccaggg cgccatagac accccacacg tggtcacacg tggcccacac tccgcctctc   8880
acgctgcctc cagccaggct actgccaagc ccttcctctg agccatacct gggccgctgg   8940
atcccagaga gaaatggaga ggccctcacg tggtgtcctc cagtccaacc ctccctgtca   9000
ccctgtcagc agcaccccac agccaaacac aggatggatg cgtgggctcc atccccccact   9060
cacccacacc tgaaccccag agcaggctac gtgcccctca cagacctcaa acccacatgt   9120
gcatctgaca ccccagatcc aaacgctccc cccggtcatg cacaccaagg gcacagcacc   9180
```

```
caccaaatcc acacggaaac acgggcaccg ggcaccccat gagcacaaag cccctccatg   9240
tctgaagaca gtccctgcac accgtcacag ccatacattc agcttcactc tcacgtccca   9300
gcccacctgc acccagctct gggcctggag cagcagaaag aggtgtgagg gcccgaggcc   9360
ggacctgcac ctgctgatga cccgggacca gcaggcagct cacggtgttg gggaagggag   9420
tggagggcac ccagggcagg agccagaggg accaggctgg tgggcggggc cgggccgggg   9480
tagggccagg aggcagctct ggacacccac aggcctgggc tcatagtcca caccaggaca   9540
gcccctcaga gcacccatgc agtgagtccc aggtcttggg agccaggccg cagagctcac   9600
gcatccttcc gagggccctg agtgaggcgg ccactgctgc gccgaggggt tgggtccttc   9660
tctggggagg gcgtggggtc tagagaggcg gagtggaggt aaccagaggt caggagagaa   9720
gccgtaagga acagagggaa aatggggcca gagtcggggc gcagggacga gaggtcagga   9780
gtggtcggcc tggccctggg ccgttgactg actcgggacc tgggtgccca ccctcagggc   9840
tggctggcgg ctccgcgcag tcccagaggg ccccggatag ggtgctctgc cactccggac   9900
agcagcaggg actgccgaga gcggcaggag gctctgtccc ccacccccgc tgccactgtg   9960
gagccgggag ggctgactgg ccaggtcccc cagagctgga cgtgtgcgtg gaggaggccg  10020
agggcgaggc gccgtggacg tggaccggcc tctgcatctt cgccgcactc ttcctgctca  10080
gcgtgagcta cagcgccgcc ctcacgctcc tcatggtggg cacccacctc caggggccca  10140
gccagggcag ggggttgggc agagccagca gagcgccctg acccacgccc tcccctcagg  10200
tgcagcggtt cctctcagcc acgcggcagg ggaggcccca gacctccctc gactacacca  10260
acgtcctcca gccccacgcc taggccgcgg gccactcacg ctccaccagg cccagctttt  10320
tctctgccag cgcctgagcc tccctcgggc tgcaccctgc cctgggtggg aaaagggaag  10380
cagacaagaa aagggggcac aaggtcacta ctgtgggctg atggccagtg aacctgagcc  10440
cagaggggcc ggctcagccg caaggttaca ggcgccgaga gaaccaccag tcgcagcccc  10500
cacccgaaaa ccgtgtctgt cccttcaaca gagtcatcga ggaggggtgg ctgctagccg  10560
ttctgagctc atcgaagggc gaattctgca gatatccatc acactggcgg ccgctcgacc  10620
taggatctcc tgtctgacag gaggcaagaa gacagattct taccccctcca tttctctttt  10680
atccctctct ggtcctcaga gagtcagtcc ttcccaaatg tcttccccct cgtctcctgc  10740
gagagccccc tgtctgataa gaatctggtg gccatgggct gcctggcccg ggacttcctg  10800
cccagcacca tttccttcac ctggaactac cagaacaaca ctgaagtcat ccagggtatc  10860
agaaccttcc caacactgag gacagggggc aagtacctag ccacctcgca ggtgttgctg  10920
tctcccaaga gcatccttga aggttcagat gaatacctgg tatgcaaaat ccactacgga  10980
ggcaaaaaca gagatctgca tgtgcccatt ccaggtaaga accaaaccct cccagcaggg  11040
gtgcccaggc ccaggcatgg cccagaggga gcagcgggtg gggcttaggc caagctgagc  11100
tcacaccttg acctttcatt ccagctgtcg cagagatgaa ccccaatgtg ttcgtcccac  11160
cacgggatgg cttctctggc cctgcaccac gcaagtctaa actcatctgc gaggccacga  11220
acttcactcc aaaaccgatc acagtatcct ggctaaagga tgggaagctc gtggaatctg  11280
gcttcaccac agatccggtg accatcgaga acaaaggatc cacaccccaa acctacaagg  11340
tcataagcac acttaccatc tctgaaatcg actggctgaa cctgaatgtg tacacctgcc  11400
gtgtggatca caggggtctc accttcttga agaacgtgtc ctccacatgt gctgccagtg  11460
agtggcctgg gataagccca atgcctagcc ctcccagatt agggaagtcc tcctacaatt  11520
```

atggccaatg ccacccagac atggtcattt gctccttgaa ctttggctcc ccagagtggc 11580
caaggacaag aatgagcaat aggcagtaga ggggtgagaa tcagctggaa ggaccagcat 11640
cttcccttaa gtaggtttgg gggatggaga ctaagctttt ttccaacttc acaactagat 11700
atgtcataac ctgacacagt gttctcttga ctgcaggtcc ctccacagac atcctaacct 11760
tcaccatccc cccctccttt gccgacatct tcctcagcaa gtccgctaac ctgacctgtc 11820
tggtctcaaa cctggcaacc tatgaaaccc tgaatatctc ctgggcttct caaagtggtg 11880
aaccactgga aaccaaaatt aaaatcatgg aaagccatcc caatggcacc ttcagtgcta 11940
agggtgtggc tagtgtttgt gtggaagact ggaataacag gaaggaattt gtgtgtactg 12000
tgactcacag ggatctgcct tcaccacaga agaaattcat ctcaaaaccc aatggtaggt 12060
atcccccctt cccttcccct ccaattgcag gacccttcct gtacctcata gggagggcag 12120
gtcctcttcc accctatcct cactactgtc ttcatttaca gaggtgcaca aacatccacc 12180
tgctgtgtac ctgctgccac cagctcgtga gcaactgaac ctgagggagt cagccacagt 12240
cacctgcctg gtgaagggct tctctcctgc agacatcagt gtgcagtggc ttcagagagg 12300
gcaactcttg ccccaagaga agtatgtgac cagtgccccg atgccagagc ctggggcccc 12360
aggcttctac tttacccaca gcatcctgac tgtgacagag gaggaatgga actccggaga 12420
gacctatacc tgtgttgtag gccacgaggc cctgccacac ctggtgaccg agaggaccgt 12480
ggacaagtcc actggtaaac ccacactgta caatgtctcc ctgatcatgt ctgacacagg 12540
cggcacctgc tattgaccat gctagcgctc aaccaggcag gccctgggtg tccagttgct 12600
ctgtgtatgc aaactaacca tgtcagagtg agatgttgca ttttataaaa attagaaata 12660
aaaaaaatcc attcaaacgt cactggtttt gattatacaa tgctcatgcc tgctgagaca 12720
gttgtgtttt gcttgctctg cacacaccct gcatacttgc ctccaccctg gcccttcctc 12780
taccttgcca gtttcctcct tgtgtgtgaa ctcagtcagg cttacaacag acagagtatg 12840
aacatgcgat tcctccagct acttcttgat atatggctga aagcttgcct aacctggtgc 12900
aggcagcatt caggcacata tatagacaca catgcattta tacatagata tataggtaca 12960
catgtgtaga cacatacatg aatgtgtatt catggacaca cagacaaagg tacacatata 13020
tacacatgag ttcatgcgca cacacatgca tggacactta caaacgcctt cagagacaaa 13080
taggcataga cacacaacca ctcacagaaa cagataccaa tatgcatggt cctgtgtaca 13140
cagaaacaga ctataggcaa atatacacaa ataaactata tagatacaaa gatatgcata 13200
tacacacatg tacagaaaca tcttcacatg tgtacactaa catgtggaca ggtatagcac 13260
acagatacac ctggactctg accagggctg taatctccaa ggctcacggc tcagagagcc 13320
tacactaggc tgggtcactg atactcctca ggagcccact ctatgattgg gagagataac 13380
cccaggtaca aagtatgcct atctgtctca acaccatggg gcagaagata ctccactaac 13440
cacccatgac agaaagttag ccttggctgt gtctccatta atagaacacc tcagaagacc 13500
aatgtgaaat tgcctaaccc actcacaccc accctgatct ccagttcaaa atgcagaaaa 13560
cataatgcag ttgtccaaaa gatgccccaa ccacacacac acacacacac acacacacac 13620
acacacacac acacacacac acacacacac accatcaagg agcctctgta aggagtcacc 13680
acccaataac actgcctctt tgggctcata tcctggacat tcttcatatt catatccatt 13740
tggggcctag gctttagata tccccaaggg ctcatcttta cagggatcag agatcccaat 13800
aaatgccctg gtcccacagc ctccctcagg tatctgtctg tttatctctt ggtaccaaga 13860
cccaacattg ctggcagggg taggacaagc aacgcacggg aactctgatc aaagaaagtc 13920

-continued

```
atgagatgcc tgagtccttc aggaagtaag gagggacaac ctctggtatc cctgttctta  13980
ttgctaaagc ccaagagaca gggagacctg ctctaaattc tcagtctaaa cagcaccgat  14040
ggcaccacct gctcagggaa agtccagagc acaccaatat cattttgcca cagttcctga  14100
gtctgccttt acccaggtcc atacattgca tctgtcttgc ttgctctgct gccccagggc  14160
tcctggaaca aaggctccaa attagtgtgt cctacagctt ggcctgttct gtgcctccgt  14220
ctagcttgag ctattagggg accagtcaat actcgctaag attctccaga accatcaggg  14280
caccccaacc cttatgcaaa tgctcagtca ccccaagact tggcttgacc ctccctctct  14340
gtgtcccttc atagaggggg aggtgaatgc tgaggaggaa ggctttgaga acctgtggac  14400
cactgcctcc accttcatcg tcctcttcct cctgagcctc ttctacagca ccaccgtcac  14460
cctgttcaag gtagtatggt tgtggggctg aggacacagg gctgggacag ggagtcacca  14520
gtcctcactg cctctacctc tactccctac aagtggacag caattcacac tgtctctgtc  14580
acctgcaggt gaaatgactc tcagcatgga aggacagcag agaccaagag atcctcccac  14640
agggacacta cctctgggcc tgggatacct gactgtatga ctagtaaact tattcttacg  14700
tctttcctgt gttgccctcc agcttttatc tctgagatgg tcttctttct agactgacca  14760
aagacttttt gtcaacttgt acaatctgaa gcaatgtctg gcccacagac agctgagctg  14820
taaacaaatg tcacatggaa ataaatactt tatcttgtga actcacttta ttgtgaagga  14880
atttgttttg tttttcaaac ctttcctgcg gtgttgacag cccaaggatt atctgaatag  14940
agcttaggaa ctggaaatgg aacagtgcag tctgatggta cttaagggag aaagagggaa  15000
aggaggtgtg gaagaagaaa aaagagaagc agaggggggag gggagaaggg agagggagag  15060
ggagagggag agggagaggg agagggagag ggagagagag agagagagag agagagagag  15120
agagagcatg cactctaaca gcaaagtaca acacaggcag ccaatggata acactctggt  15180
tatctaccct gatggaagaa gggaagtagg gcagagaaaa ttccaggcct aatctcccaa  15240
aagcaacaga acctggaaac tagcctctag ccttaggtct ctgctctgtc cccagcccac  15300
catcttgggc tggtgttgct tcaagctagt aatttaggtc ttatcccaaa gctttgtggt  15360
atgtgggtgt gcctttgggg agttggctga gattttgaag atgtttgtac ctctcccaca  15420
acatgacaag ccctaggggt tagtcaataa ctcaaattct ctgtctatga caactgctgt  15480
atgactatat gaagaaatgg gataaagatg ctatagtcac tcgag                  15525
```

<210> SEQ ID NO 7
<211> LENGTH: 5270
<212> TYPE: DNA
<213> ORGANISM: artificial sequence
<220> FEATURE:
<223> OTHER INFORMATION: synthetic polynucleotide (5' arm)

<400> SEQUENCE: 7

```
agcgcgcgta atacgactca ctatagggcg aattggagct ccaccgcggt ggcggccgct     60
cctgagagaa cagactctgg aaatagatgg gacttaagga gctaagatct agagctcatc    120
tacagagcag aatcccagcc aagagaacaa agaatactgg ctctctctcc tgttccctac    180
tcctagagtt ctaaaacaca ctatagggaa gggagcctct agacctccgt ccattcccca    240
tcttgctcat tccatcttcc catgtcccca ggtctccaag ccacagacac tacctttcct    300
attcacccac ctttctgtgt ccctaggtcc ccaggccata gtcacctccc cccacacaca    360
ccccactcac cctgccccat ctatgcccct agatgcttac ttaccagagt cttttgtctg    420
```

-continued

```
acgtggggct acaagcatct atgctcccta agcacctact gctgacctgt aggacccagc    480
tctgaaccaa ctcatataag taaatacaga ctctcccctg tcttaggatg gcctcctgga    540
tcaggaggag accactgcca aagaaccttc tctcagagca ctgaactcct cccctgtacc    600
acttaggaca gacctgagac ctattattac tgattaccag agctctggca gtgaccacgg    660
aggagatagg tccaccctgg acacaggaaa cacagcagca gagatactgc tccatcacaa    720
cagtagagtg acactttaga ctttaatttg ggtcactttc ctgctgcaga ggtgggatca    780
gaaagcaaag agcagtatga gtgcctgata ggcacccaag tacactatag agtactcatg    840
gtgaataagg tacctccatg gcttcccagg gaggggcagc cccaccccca ccatcacaga    900
cctttctcca tagttgataa ctcagacaca agtgaatgac agatggacct ccatctactc    960
ttattttaaa aagaagacaa accccacagg ctcgagaact ttagcgactg ttttgagaga   1020
aatcattggt ccctgactca agagatgact ggcagattgg ggatcagaat acccatactc   1080
tgtggctagt gtgaggttta agcctcagag tccctgtggt ctctgactgg tgcaaggttt   1140
tgactaagcg gagcaccaca gtgctaactg ggaccacggt gacacgtggc tcaacaaaaa   1200
ccttctgttt ggagctctcc aggggcagcc tgagctatga ggaagtagag aggcttgaga   1260
aatctgagga agaaaagagt agatctgaga ggaaaggtag ctttctggag gtcaggagac   1320
agtgcagaga agaacgagtt actgtggaca ggtcttagat ggggaaagaa tgagcaaatg   1380
caagcatcag aagggtggat gcaatgtcct gccaaggact taccaagagg atccccggac   1440
agagcaggca ggtggagttg actgagagga cagggtaggt gcaggtccct ctctcgtttc   1500
ctttctcctt ctcctgtttc cttcctctct tgtcacaggt ctcactatgc tagccaaggc   1560
tagcctgaaa gattaccatc ctacagatgg gcccatccag ttgagttaag gtggagatct   1620
ctccaaacat ctgagtttct gaggcttgga tgccactggg gacgccaagg gactttgggc   1680
tgggtttggt tggccccaga tgaagggcta cttcactggg tctataatta ctctgatgtc   1740
taggaccagg gggctcaggt cactcaggtc aggtgagtcc tgcatctggg gactgtgggg   1800
ttcaggtgtc ctaaggcagg atgtggagag agttttagta taggaacaga ggcagaacag   1860
agactgtgct actggtactt cgatgtctgg ggcgcaggga ccacggtcac cgtctcctca   1920
ggtaagctgg ctttttttctt tctgcacatt ccattctgaa atgggaaaag atattctcag   1980
atctccccat gtcaggccat ctgccacact ctgcatgctg cagaagcttt tctgtaagga   2040
tagggtcttc actcccagga aaagaggcag tcagaggcta gctgcctgtg gaacagtgac   2100
aatcatggaa aataggcatt tacattgtta ggctacatgg gtagatgggt ttttgtacac   2160
ccactaaagg ggtctatgat agtgtgacta ctttgactac tggggccaag gcaccactct   2220
cacagtctcc tcaggtgagt ccttacaacc tctctcttct attcagctta aatagatttt   2280
actgcatttg ttggggggga aatgtgtgta tctgaatttc aggtcatgaa ggactaggga   2340
caccttggga gtcagaaagg gtcattggga gccctggctg acgcagacag acatcctcag   2400
ctcccatact tcatggccag agatttatag ggatcctggc cagcattgcc gctaggtccc   2460
tctcttctat gctttctttg tccctcactg gcctccatct gagataatcc tggagcccta   2520
gccaaggatc atttattgtc aggggtctaa tcattgttgt cacaatgtgc ctggtttgct   2580
tactggggcc aagggactct ggtcactgtc tctgcaggtg agtcctaact tctcccattc   2640
taaatgcatg ttggggggat tctgagcctt caggaccaag attctctgca aacgggaatc   2700
aagattcaac ccctttgtcc caaagttgag acatgggtct gggtcaggga ctctctgcct   2760
gctggtctgt ggtgacatta gaactgaagt atgatgaagg atctgccaga actgaagctt   2820
```

```
gaagtctgag gcagaatctt gtccagggtc tatcggactc ttgtgagaat taggggctga   2880
cagttgatgg tgacaatttc agggtcagtg actgtctggt ttctctgagg tgaggctgga   2940
atataggtca ccttgaagac ttaagagggg tccagggggc ttctgcacag gcagggaaca   3000
gaatgtggaa caatgacttg aatggttgat tcttgtgtga caccaggaat tggcataatg   3060
tctgagttgc ccaggggtga ttctagtcag actctggggt ttttgtcggg tatagaggaa   3120
aaatccacta ttgtgattac tatgctatgg actactgggg tcaaggaacc tcagtcaccg   3180
tctcctcagg taagaatggc ctctccaggt ctttattttt aacctttgtt atggagtttt   3240
ctgagcattg cagactaatc ttggatattt gtccctgagg gagccggctg agagaagttg   3300
ggaaataaac tgtctaggga tctcagagcc tttaggacag attatctcca catctttgaa   3360
aaactaagaa tctgtgtgat ggtgttggtg gagtccctgg atgatgggat agggactttg   3420
gaggctcatt tgagggagat gctaaaacaa tcctatggct ggagggatag ttggggctgt   3480
agttggagat tttcagtttt tagaataaaa gtattagctg cggaatatac ttcaggacca   3540
cctctgtgac agcatttata cagtatccga tgcatatgga caaagagtgg agtggggcac   3600
tttctttaga tttgtgagga atgttccaca ctagattgtt taaaacttca tttgttggaa   3660
ggagagctgt cttagtgatt gagtcaaggg agaaaggcat ctagcctcgg tctcaaaagg   3720
gtagttgctg tctagagagg tctggtggag cctgcaaaag tccagctttc aaaggaacac   3780
agaagtatgt gtatggaata ttagaagatg ttgcttttac tcttaagttg gttcctagga   3840
aaaatagtta aatactgtga ctttaaaatg tgagagggtt ttcaagtact catttttta    3900
aatgtccaaa atttttgtca atcaatttga ggtcttgttt gtgtagaact gacattactt   3960
aaagtttaac cgaggaatgg gagtgaggct ctctcataac ctattcagaa ctgactttta   4020
acaataataa attaagtttc aaatattttt aaatgaattg agcaatgttg agttggagtc   4080
aagatggccg atcagaacca gaacacctgc agcagctggc aggaagcagg tcatgtggca   4140
aggctatttg gggaagggaa aataaaacca ctaggtaaac ttgtagctgt ggtttgaaga   4200
agtggttttg aaacactctg tccagcccca ccaaaccgaa agtccaggct gagcaaaaca   4260
ccacctgggt aatttgcatt tctaaaataa gttgaggatt cagccgaaac tggagaggtc   4320
ctcttttaac ttattgagtt caacctttta attttagctt gagtagttct agtttcccca   4380
aacttaagtt tatcgacttc taaaatgtat ttagaattca ttttcaaaat taggttatgt   4440
aagaaattga aggactttag tgtctttaat ttctaatata tttagaaaac ttcttaaaat   4500
tactctatta ttcttccctc tgattattgg tctccattca attcttttcc aatacccgaa   4560
gcatttacag tgactttgtt catgatcttt tttagttgtt tgttttgcct tactattaag   4620
actttgacat tctggtcaaa acggcttcac aaatcttttt caagaccact ttctgagtat   4680
tcattttagg agaaagactt ttttttaaa tgaatgcaat tatctagact tatttcagtt    4740
gaacatgctg gttggtggtt gagaggacac tcagtcagtc agtggcgtga agggcttcta   4800
agccagtcca catgctctgt gtgaactccc tctggccctg cttattgttg aatgggccaa   4860
aggtctgaga ccaggctgct gctgggtagg cctggacttt gggtctccca cccagacctg   4920
ggaatgtatg gttgtggctt ctgccaccca tccacctggc tgctcatgga ccagccagcc   4980
tcggtggctt tgaaggaaca attccacaca aagactctgg acctctccga aaccaggcac   5040
cgcaaatggt aagccagagg cagccacagc tgtggctgct gctcttaaag cttgtaaact   5100
gtttctgctt aagagggact gagtcttcag tcattgcttt agggggagaa agagacattt   5160
```

gtgtgtcttt tgagtaccgt tgtctgggtc actcacattt aactttcctt gaaaaactag 5220
actcgacatc gattgtcgag gaattccgat catattcaat aacccttaat 5270

<210> SEQ ID NO 8
<211> LENGTH: 4902
<212> TYPE: DNA
<213> ORGANISM: artificial sequence
<220> FEATURE:
<223> OTHER INFORMATION: synthetic polynucleotide (3'arm)

<400> SEQUENCE: 8
gatctcctgt ctgacaggag gcaagaagac agattcttac ccctccattt ctcttttatc 60
cctctctggt cctcagagag tcagtccttc ccaaatgtct tccccctcgt ctcctgcgag 120
agccccctgt ctgataagaa tctggtggcc atgggctgcc tggcccggga cttcctgccc 180
agcaccattt ccttcacctg gaactaccag aacaacactg aagtcatcca gggtatcaga 240
accttcccaa cactgaggac agggggcaag tacctagcca cctcgcaggt gttgctgtct 300
cccaagagca tccttgaagg ttcagatgaa tacctggtat gcaaaatcca ctacggaggc 360
aaaaacagag atctgcatgt gcccattcca ggtaagaacc aaaccctccc agcaggggtg 420
cccaggccca ggcatggccc agagggagca gcgggtgggg cttaggccaa gctgagctca 480
caccttgacc tttcattcca gctgtcgcag agatgaaccc caatgtgttc gtcccaccac 540
gggatggctt ctctggccct gcaccacgca agtctaaact catctgcgag gccacgaact 600
tcactccaaa accgatcaca gtatcctggc taaaggatgg gaagctcgtg gaatctggct 660
tcaccacaga tccggtgacc atcgagaaca aaggatccac accccaaacc tacaaggtca 720
taagcacact taccatctct gaaatcgact ggctgaacct gaatgtgtac acctgccgtg 780
tggatcacag ggtctcacc ttcttgaaga acgtgtcctc cacatgtgct gccagtgagt 840
ggcctgggat aagcccaatg cctagccctc ccagattagg gaagtcctcc tacaattatg 900
gccaatgcca cccagacatg gtcatttgct ccttgaactt tggctcccca gagtggccaa 960
ggacaagaat gagcaatagg cagtagaggg gtgagaatca gctggaagga ccagcatctt 1020
cccttaagta ggtttggggg atggagacta agcttttttc caacttcaca actagatatg 1080
tcataacctg acacagtgtt ctcttgactg caggtccctc cacagacatc ctaaccttca 1140
ccatcccccc ctcctttgcc gacatcttcc tcagcaagtc cgctaacctg acctgtctgg 1200
tctcaaacct ggcaacctat gaaaccctga atatctcctg ggcttctcaa agtggtgaac 1260
cactggaaac caaaattaaa atcatggaaa gccatcccaa tggcaccttc agtgctaagg 1320
gtgtggctag tgtttgtgtg gaagactgga ataacaggaa ggaatttgtg tgtactgtga 1380
ctcacaggga tctgccttca ccacagaaga aattcatctc aaaacccaat ggtaggtatc 1440 ccccctttccc ttcccctcca attgcaggac ccttcctgta cctcataggg agggcaggtc 1500
ctcttccacc ctatcctcac tactgtcttc atttacagag gtgcacaaac atccacctgc 1560
tgtgtacctg ctgccaccag ctcgtgagca actgaacctg agggagtcag ccacagtcac 1620
ctgcctggtg aagggcttct ctcctgcaga catcagtgtg cagtggcttc agagagggca 1680
actcttgccc caagagaagt atgtgaccag tgccccgatg ccagagcctg gggccccagg 1740
cttctacttt acccacagca tcctgactgt gacagaggag gaatggaact ccggagagac 1800
ctatacctgt gttgtaggcc acgaggccct gccacacctg gtgaccgaga ggaccgtgga 1860
caagtccact ggtaaaccca cactgtacaa tgtctccctg atcatgtctg acacaggcgg 1920
cacctgctat tgaccatgct agcgctcaac caggcaggcc ctgggtgtcc agttgctctg 1980

-continued

```
tgtatgcaaa ctaaccatgt cagagtgaga tgttgcattt tataaaaatt agaaataaaa   2040
aaaatccatt caaacgtcac tggttttgat tatacaatgc tcatgcctgc tgagacagtt   2100
gtgttttgct tgctctgcac acaccctgca tacttgcctc caccctggcc cttcctctac   2160
cttgccagtt tcctccttgt gtgtgaactc agtcaggctt acaacagaca gagtatgaac   2220
atgcgattcc tccagctact tcttgatata tggctgaaag cttgcctaac ctggtgcagg   2280
cagcattcag gcacatatat agacacacat gcatttatac atagatatat aggtacacat   2340
gtgtagacac atacatgaat gtgtattcat ggacacacag acaaaggtac acatatatac   2400
acatgagttc atgcgcacac acatgcatgg acacttacaa acgccttcag agacaaatag   2460
gcatagacac acaaccactc acagaaacag ataccaatat gcatggtcct gtgtacacag   2520
aaacagacta taggcaaata tacacaaata aactatatag atacaaagat atgcatatac   2580
acacatgtac agaaacatct tcacatgtgt acactaacat gtggacaggt atagcacaca   2640
gatacacctg gactctgacc agggctgtaa tctccaaggc tcacggctca gagagcctac   2700
actaggctgg gtcactgata ctcctcagga gcccactcta tgattgggag agataacccc   2760
aggtacaaag tatgcctatc tgtctcaaca ccatggggca gaagatactc cactaaccac   2820
ccatgacaga aagttagcct tggctgtgtc tccattaata gaacacctca gaagaccaat   2880
gtgaaattgc ctaacccact cacacccacc ctgatctcca gttcaaaatg cagaaaacat   2940
aatgcagttg tccaaaagat gccccaacca cacacacaca cacacacaca cacacacaca   3000
cacacacaca cacacacaca cacacacacc atcaaggagc ctctgtaagg agtcaccacc   3060
caataacact gcctctttgg gctcatatcc tggacattct tcatattcat atccatttgg   3120
ggcctaggct ttagatatcc ccaagggctc atctttacag ggatcagaga tcccaataaa   3180
tgccctggtc ccacagcctc cctcaggtat ctgtctgttt atctcttggt accaagaccc   3240
aacattgctg gcaggggtag gacaagcaac gcacgggaac tctgatcaaa gaaagtcatg   3300
agatgcctga gtccttcagg aagtaaggag ggacaacctc tggtatccct gttcttattg   3360
ctaaagccca agagacaggg agacctgctc taaattctca gtctaaacag caccgatggc   3420
accacctgct cagggaaagt ccagagcaca ccaatatcat tttgccacag ttcctgagtc   3480
tgcctttacc caggtccata cattgcatct gtcttgcttg ctctgctgcc ccagggctcc   3540
tggaacaaag gctccaaatt agtgtgtcct acagcttggc ctgttctgtg cctccgtcta   3600
gcttgagcta ttaggggacc agtcaatact cgctaagatt ctccagaacc atcagggcac   3660
cccaaccctt atgcaaatgc tcagtcaccc caagacttgg cttgaccctc cctctctgtg   3720
tcccttcata gagggggagg tgaatgctga ggaggaaggc tttgagaacc tgtggaccac   3780
tgcctccacc ttcatcgtcc tcttcctcct gagcctcttc tacagcacca ccgtcaccct   3840
gttcaaggta gtatggttgt ggggctgagg acacagggct gggacaggga gtcaccagtc   3900
ctcactgcct ctacctctac tccctacaag tggacagcaa ttcacactgt ctctgtcacc   3960
tgcaggtgaa atgactctca gcatggaagg acagcagaga ccaagagatc ctcccacagg   4020
gacactacct ctgggcctgg gatacctgac tgtatgacta gtaaacttat tcttacgtct   4080
ttcctgtgtt gccctccagc ttttatctct gagatggtct tctttctaga ctgaccaaag   4140
actttttgtc aacttgtaca atctgaagca atgtctggcc cacagacagc tgagctgtaa   4200
acaaatgtca catggaaata aatactttat cttgtgaact cactttattg tgaaggaatt   4260
tgttttgttt ttcaaacctt tcctgcggtg ttgacagccc aaggattatc tgaatagagc   4320
```

-continued ttaggaactg gaaatggaac agtgcagtct gatggtactt aagggagaaa gagggaaagg 4380
aggtgtggaa gaagaaaaaa gagaagcaga gggggagggg agaagggaga gggagaggga 4440
gagggagagg gagagggaga gggagaggga gagagagaga gagagagaga gagagagaga 4500
gagcatgcac tctaacagca aagtacaaca caggcagcca atggataaca ctctggttat 4560
ctaccctgat ggaagaaggg aagtagggca gagaaaattc caggcctaat ctcccaaaag 4620
caacagaacc tggaaactag cctctagcct taggtctctg ctctgtcccc agcccaccat 4680
cttgggctgg tgttgcttca agctagtaat ttaggtctta tcccaaagct ttgtggtatg 4740
tgggtgtgcc tttggggagt tggctgagat tttgaagatg tttgtacctc tcccacaaca 4800
tgacaagccc taggggttag tcaataactc aaattctctg tctatgacaa ctgctgtatg 4860
actatatgaa gaaatgggat aaagatgcta tagtcactcg ag 4902

<210> SEQ ID NO 9
<211> LENGTH: 20836
<212> TYPE: DNA
<213> ORGANISM: artificial sequence
<220> FEATURE:
<223> OTHER INFORMATION: synthetic polynucleotide (transgenic DNA construct + 5' and 3'arms)

<400> SEQUENCE: 9
agcgcgcgta atacgactca ctatagggcg aattggagct ccaccgcggt ggcggccgct 60
cctgagagaa cagactctgg aaatagatgg gacttaagga gctaagatct agagctcatc 120
tacagagcag aatcccagcc aagagaacaa agaatactgg ctctctctcc tgttccctac 180
tcctagagtt ctaaaacaca ctatagggaa gggagcctct agacctccgt ccattcccca 240
tcttgctcat tccatcttcc catgtcccca ggtctccaag ccacagacac tacctttcct 300
attcacccac ctttctgtgt ccctaggtcc ccaggccata gtcacctccc cccacacaca 360
ccccactcac cctgccccat ctatgcccct agatgcttac ttaccagagt cttttgtctg 420
acgtggggct acaagcatct atgctcccta agcacctact gctgacctgt aggacccagc 480
tctgaaccaa ctcatataag taaatacaga ctctcccctg tcttaggatg gcctcctgga 540
tcaggaggag accactgcca aagaaccttc tctcagagca ctgaactcct cccctgtacc 600
acttaggaca gacctgagac ctattattac tgattaccag agctctggca gtgaccacgg 660
aggagatagg tccaccctgg acacaggaaa cacagcagca gagatactgc tccatcacaa 720
cagtagagtg acactttaga ctttaatttg ggtcactttc ctgctgcaga ggtgggatca 780
gaaagcaaag agcagtatga gtgcctgata ggcacccaag tacactatag agtactcatg 840
gtgaataagg tacctccatg gcttcccagg gaggggcagc cccaccccca ccatcacaga 900
cctttctcca tagttgataa ctcagacaca agtgaatgac agatggacct ccatctactc 960
ttattttaaa aagaagacaa accccacagg ctcgagaact ttagcgactg ttttgagaga 1020
aatcattggt ccctgactca agagatgact ggcagattgg ggatcagaat acccatactc 1080
tgtggctagt gtgaggttta agcctcagag tccctgtggt ctctgactgg tgcaaggttt 1140
tgactaagcg gagcaccaca gtgctaactg ggaccacggt gacacgtggc tcaacaaaaa 1200
ccttctgttt ggagctctcc aggggcagcc tgagctatga ggaagtagag aggcttgaga 1260
aatctgagga agaaaagagt agatctgaga ggaaaggtag ctttctggag gtcaggagac 1320
agtgcagaga agaacgagtt actgtggaca ggtcttagat ggggaaagaa tgagcaaatg 1380
caagcatcag aagggtggat gcaatgtcct gccaaggact taccaagagg atccccggac 1440

-continued

```
agagcaggca ggtggagttg actgagagga cagggtaggt gcaggtccct ctctcgtttc   1500
ctttctcctt ctcctgtttc cttcctctct tgtcacaggt ctcactatgc tagccaaggc   1560
tagcctgaaa gattaccatc ctacagatgg gcccatccag ttgagttaag gtggagatct   1620
ctccaaacat ctgagtttct gaggcttgga tgccactggg gacgccaagg gactttgggc   1680
tgggtttggt tggccccaga tgaagggcta cttcactggg tctataatta ctctgatgtc   1740
taggaccagg gggctcaggt cactcaggtc aggtgagtcc tgcatctggg gactgtgggg   1800
ttcaggtgtc ctaaggcagg atgtggagag agttttagta taggaacaga ggcagaacag   1860
agactgtgct actggtactt cgatgtctgg ggcgcaggga ccacggtcac cgtctcctca   1920
ggtaagctgg ctttttcttt tctgcacatt ccattctgaa atgggaaaag atattctcag   1980
atctccccat gtcaggccat ctgccacact ctgcatgctg cagaagcttt tctgtaagga   2040
tagggtcttc actcccagga aaagaggcag tcagaggcta gctgcctgtg gaacagtgac   2100
aatcatggaa aataggcatt tacattgtta ggctacatgg gtagatgggt ttttgtacac   2160
ccactaaagg ggtctatgat agtgtgacta ctttgactac tggggccaag gcaccactct   2220
cacagtctcc tcaggtgagt ccttacaacc tctctcttct attcagctta aatagatttt   2280
actgcatttg ttggggggga aatgtgtgta tctgaatttc aggtcatgaa ggactaggga   2340
caccttggga gtcagaaagg gtcattggga gccctggctg acgcagacag acatcctcag   2400
ctcccatact tcatggccag agatttatag ggatcctggc cagcattgcc gctaggtccc   2460
tctcttctat gctttctttg tccctcactg gcctccatct gagataatcc tggagcccta   2520
gccaaggatc atttattgtc aggggtctaa tcattgttgt cacaatgtgc ctggtttgct   2580
tactggggcc aagggactct ggtcactgtc tctgcaggtg agtcctaact tctcccattc   2640
taaatgcatg ttgggggggat tctgagcctt caggaccaag attctctgca aacgggaatc   2700
aagattcaac ccctttgtcc caaagttgag acatgggtct gggtcaggga ctctctgcct   2760
gctggtctgt ggtgacatta gaactgaagt atgatgaagg atctgccaga actgaagctt   2820
gaagtctgag gcagaatctt gtccagggtc tatcggactc ttgtgagaat taggggctga   2880
cagttgatgg tgacaatttc agggtcagtg actgtctggt ttctctgagg tgaggctgga   2940
atataggtca ccttgaagac ttaagagggg tccagggggc ttctgcacag gcagggaaca   3000
gaatgtggaa caatgacttg aatggttgat tcttgtgtga caccaggaat tggcataatg   3060
tctgagttgc ccaggggtga ttctagtcag actctggggt tttgtcgggg tatagaggaa   3120
aaatccacta ttgtgattac tatgctatgg actactgggg tcaaggaacc tcagtcaccg   3180
tctcctcagg taagaatggc ctctccaggt ctttattttt aacctttgtt atggagtttt   3240
ctgagcattg cagactaatc ttggatattt gtccctgagg gagccggctg agagaagttg   3300
ggaaataaac tgtctaggga tctcagagcc tttaggacag attatctcca catctttgaa   3360
aaactaagaa tctgtgtgat ggtgttggtg gagtccctgg atgatgggat agggactttg   3420
gaggctcatt tgagggagat gctaaaacaa tcctatggct ggagggatag ttggggctgt   3480
agttggagat tttcagtttt tagaataaaa gtattagctg cggaatatac ttcaggacca   3540
cctctgtgac agcatttata cagtatccga tgcataggga caaagagtgg agtggggcac   3600
tttctttaga tttgtgagga atgttccaca ctagattgtt taaaacttca tttgttggaa   3660
ggagagctgt cttagtgatt gagtcaaggg agaaaggcat ctagcctcgg tctcaaaagg   3720
gtagttgctg tctagagagg tctggtggag cctgcaaaag tccagctttc aaaggaacac   3780
agaagtatgt gtatggaata ttagaagatg ttgcttttac tcttaagttg gttcctagga   3840
```

-continued

```
aaaatagtta aatactgtga ctttaaaatg tgagagggtt ttcaagtact catttttttta   3900
aatgtccaaa atttttgtca atcaatttga ggtcttgttt gtgtagaact gacattactt   3960
aaagtttaac cgaggaatgg gagtgaggct ctctcataac ctattcagaa ctgacttttta   4020
acaataataa attaagtttc aaatattttt aaatgaattg agcaatgttg agttggagtc   4080
aagatggccg atcagaacca gaacacctgc agcagctggc aggaagcagg tcatgtggca   4140
aggctatttg gggaagggaa aataaaacca ctaggtaaac ttgtagctgt ggtttgaaga   4200
agtggttttg aaacactctg tccagcccca ccaaaccgaa agtccaggct gagcaaaaca   4260
ccacctgggt aatttgcatt tctaaaataa gttgaggatt cagccgaaac tggagaggtc   4320
ctcttttaac ttattgagtt caacctttta attttagctt gagtagttct agtttcccca   4380
aacttaagtt tatcgacttc taaaatgtat ttagaattca ttttcaaaat taggttatgt   4440
aagaaattga aggactttag tgtctttaat ttctaatata tttagaaaac ttcttaaaat   4500
tactctatta ttcttccctc tgattattgg tctccattca attcttttcc aatacccgaa   4560
gcatttacag tgactttgtt catgatcttt tttagttgtt tgttttgcct tactattaag   4620
actttgacat tctggtcaaa acggcttcac aaatcttttt caagaccact ttctgagtat   4680
tcattttagg agaaagactt tttttttaaa tgaatgcaat tatctagact tatttcagtt   4740
gaacatgctg gttggtggtt gagaggacac tcagtcagtc agtggcgtga agggcttcta   4800
agccagtcca catgctctgt gtgaactccc tctggccctg cttattgttg aatgggccaa   4860
aggtctgaga ccaggctgct gctgggtagg cctggacttt gggtctccca cccagacctg   4920
ggaatgtatg gttgtggctt ctgccaccca tccacctggc tgctcatgga ccagccagcc   4980
tcggtggctt tgaaggaaca attccacaca aagactctgg acctctccga aaccaggcac   5040
cgcaaatggt aagccagagg cagccacagc tgtggctgct gctcttaaag cttgtaaact   5100
gtttctgctt aagagggact gagtcttcag tcattgcttt agggggagaa agagacattt   5160
gtgtgtcttt tgagtaccgt tgtctgggtc actcacattt aactttcctt gaaaaactag   5220
actcgacatc gattgtcgag gaattccgat catattcaat aacccttaat ataacttcgt   5280
ataatgtatg ctatacgaag ttattaggtc tgaagaggag tttacgtcca gccttcgaag   5340
ggtcctcagg gagtgcatcc gccccaaccc ttttccccct cgtctcctgt gagaattccc   5400
cgtcggatac gagcagcgtg gccgttggct gcctcgcaca ggacttcctt cccgactcca   5460
tcactttctc ctggaaatac aagaacaact ctgacatcag cagcacccgg ggcttcccat   5520
cagtcctgag agggggcaag tacgcagcca cctcacaggt gctgctgcct tccaaggacg   5580
tcatgcaggg cacagacgaa cacgtggtgt gcaaagtcca gcaccccaac ggcaacaaag   5640
aaaagaacgt gcctcttcca ggtgagggcc gggcccagcc accgggacag agagggagcc   5700
gaaggggggc gggagtggcg ggcaccgggc tgacacgtgt ccctcactgc agtgattgct   5760
gagctgcctc ccaaagtgag cgtcttcgtc ccaccccgcg acggcttctt cggcaacccc   5820
cgcaagtcca agctcatctg ccaggccacg ggtttcagtc cccggcagat tcaggtgtcc   5880
tggctgcgcg aggggaagca ggtggggtct ggcgtcacca cggaccaggt gcaggctgag   5940
gccaaagagt ctgggcccac gacctacaag gtgaccagca cactgaccat caaagagagc   6000
gactggctca gccagagcat gttcacctgc cgcgtggatc acaggggcct gaccttccag   6060
cagaatgcgt cctccatgtg tgtccccggt gagtgacctg tccccagggg cagcacccac   6120
cgacacacag ggtccactc gggtctggca ttcgccaccc cggatgcagc catctactcc   6180
```

-continued

```
ctgagccttg gcttcccaga gcggccaagg gcaggggctc gggcggcagg acccctgggc   6240
tcggcagagg cagttgctac tctttgggtg ggaaccatgc ctccgcccac atccacacct   6300
gccccacctc tgactccctt ctcttgactc cagatcaaga cacagccatc cgggtcttcg   6360
ccatcccccc atcctttgcc agcatcttcc tcaccaagtc caccaagttg acctgcctgg   6420
tcacagacct gaccacctat gacagcgtga ccatctcctg gacccgccag aatggcgaag   6480
ctgtgaaaac ccacaccaac atctccgaga gccaccccaa tgccactttc agcgccgtgg   6540
gtgaggccag catctgcgag gatgactgga attccgggga gaggttcacg tgcaccgtga   6600
cccacacaga cctgccctcg ccactgaagc agaccatctc ccggcccaag ggtaggcccc   6660
actcttgccc ctcttctgca ctcctgcaac tccttgcctc tgggggcatg gtggaaagca   6720
cccctcactc ccccgttgtc tgggcaactg gggaaaaggg gactcaaccc cagcccacag   6780
gctggtcccc ccactgcccc gccctcacca ccatctctgt tcacaggggt ggccctgcac   6840
aggcccgatg tctacttgct gccaccagcc cgggagcagc tgaacctgcg ggagtcggcc   6900
accatcacgt gcctggtgac gggcttctct cccgcggacg tcttcgtgca gtggatgcag   6960
agggggcagc ccttgtcccc ggagaagtat gtgaccagcg ccccaatgcc tgagccccag   7020
gccccaggcc ggtacttcgc ccacagcatc ctgaccgtgt ccgaagagga atggaacacg   7080
ggggagacct acacctgcgt ggtggcccat gaggccctgc ccaacagggt caccgagagg   7140
accgtggaca agtccaccgg taaacccacc ctgtacaacg tgtccctggt catgtccgac   7200
acagctggca cctgctactg accctgctgg cctgcccaca ggctcggggc ggctggccgc   7260
tctgtgtgtg catgcaaact aaccgtgtca acggggtgag atgttgcatc ttataaaatt   7320
agaaataaaa agatccattc aaaagatact ggtcctgagt gcacgatgct ctggcctact   7380
ggggcggcgg ctgtgctgca cccaccctgc gcctcccctg cagaacacct tcctccacag   7440
cccccacccc tgcctcaccc acctgcgtgc ctcagtggct tctagaaacc cctgaattcc   7500
ctgcagctgc tcacagcagg ctgacctcag acttgccatt cctcctactg cttccagaaa   7560
gaaagctgaa agcaaggcca cacgtataca ggcagcacac aggcatgtgt ggatacacat   7620
ggacagacac ggacacacac aaacacatgg acacacagag acgtgctaac ccatgggcac   7680
acacatacac agacatggac ccacacacaa acatatgtgg acacacatgt acaaacatgc   7740
acaggcacac aaagagaaca ctgactacag gcacacacac acacgggcac acacatggat   7800
atgtgcacac atggacacat acatgtgcag gacatgcaca cacacagaca cactagcaca   7860
gaggcataca cacacagaca cacacattca caaacacaca tgtgcatgca aacacacaca   7920
catgtacaga cacgagtaca tggacacatg cacacccaga gacacactga cacagacaca   7980
caggagcatg tgatacacta acacgtggac acacacgtct acccacaggc acacaacaga   8040
tggacacgcg tacacagaca tgcacacacc cacaggcaca acacgtgcgc atgccggccg   8100
gcccccgccc acattctccc agggccctgc cggatactct gtccctgcag cagtttgctc   8160
cctgcgctgt gctggccccg gggctttggg cccaggctct gcttgtcctt ctgtctctgc   8220
ttggaggtgc tgccatggca cccagcttgg gctctgcctg gggagcggag gccccaggga   8280
tagcatgtga cccctgctga ggccaggctc ctgatgaagg cagcagatag cccccacacc   8340
caccggtgag cagaaccaga gcctgtgcca tgtgctgaga gcaggcagtg actaagcata   8400
tgggcccaga gggcagagtg gctgccctgg gcagctgctc ctcttagcgg gaggcctcag   8460
gagatgagct agagcaagtc tgcccctgca aataccacct gctccccaac ccacagcagg   8520
gagcaggcga ggtcagacag cagcagcccg ggaaggaccg agccccagca gggaaggcag   8580
```

-continued

```
ggcccgagtg aggtctccac acccaacgca cagtgctgtc tctaactggg gccacctccg   8640
agtccccgcc acactcttgg ccctttggag tcctgggctc caggtgtctc ccaagggccc   8700
atctgtgcag gggatgcaac cccccgaatg tcctcatccc actgtggagc tcaggtctct   8760
gtctgctccc tgggtcctgg cagggtagga caagtccgcc aggatgtccc catgcagact   8820
ctgctccaag agggagctgg agagtcaggg ccttggtgag ggagtcagga tcgggttccc   8880
cccagctcag tcctcccacc tgccagcccc cacagcacag ggcagggcca cacccccctgc  8940
ttccccctcc aggagagtca ggacatgctg gccgctgctc cgctggggcc ccgccctcca   9000
gcccccacct tggtctgtgt gctgcatccc ccacgctctc tctgccaccc caggactctg   9060
aggaaaagac ctcagagtcc cagccctgcc cagtctcggc ctgtgccccc gctgcatcag   9120
gctttcaggg gcccagccca tgccctgggc agtgcccgag cccccctgca cttgctctcc   9180
ccacccctgg gtgcagcaca gcctaggggc caagggtggg cctagaggat gggccccggg   9240
ggggctttgc tgggtgccac cccagcctga ccctattccc ccgtgctgtg tctcctgcag   9300
agggggaggt gagcgccgac gaggagggct ttgagaacct gtgggccacc gcctccacct   9360
tcatcgtcct cttcctcctg agcctcttct acagtaccac cgtcaccttg ttcaaggtag   9420
cacggctgtg gcacagggag gagggtgcag ggcgagtgtg gggcccaggg agcagcctgg   9480
gctggacgtc tagcccggag gcccccacac caccccactg ggtcatctct gccccggctc   9540
ccttccccgac cacggggaaa gcatttcaca ctgtctctgt tgcctgtagg tgaaatgatc  9600
ccaacagaag aacatcggag accagagaga ggaactcaaa ggggcgctgc ctccgggtct   9660
ggggtcctgg cctgcgtggc ctgttggcac gtgtttctct tccccgcccg gcctccagtt   9720
gtgtgctctc acacaggctt ctttctcgac cggcaggggc tggctggctt gcaggccacg   9780
aggtggggct ctaccccaca ctgctttgct gtgtatacgc ttgttgcctg aaataaatat   9840
gcacatttta tccatgaaac tgctttctgg tgagggtttg tttctttttc aaaactttcc   9900
tgctacaggg cattcaagcc atcgatgtcg aggaattccg atcatattca ataaccctta   9960
atataacttc gtataatgta tgctatacga agttattagg tctgaagagg agtttacgtc  10020
cagccaagct agcttggctg caggtcgagc agtgtggttt tcaagaggaa gcaaaaagcc  10080
tctccaccca ggcctggaat gtttccaccc aatgtcgagc agtgtggttt tgcaagagga  10140
agcaaaaagc ctctccaccc aggcctggaa tgtttccacc caatgtcgag cagtgtggtt  10200
ttgcaagagg aagcaaaaag cctctccacc caggcctgga atgtttccac ccaatgtcga  10260
gcaaaccccg cccagcgtct tgtcattggc gaattcgaac acgcagatgc agtcggggcg  10320
gcgcggtccc caggtccact tcgcatatta aggtgacgcg tgtggcctcg aacaccgagc  10380
gaccctgcag ccaatatggg atcggccatt gaacaagatg gattgcacgc aggttctccg  10440
gccgcttggg tggagaggct attcggctat gactgggcac aacagacaat cggctgctct  10500
gatgccgccg tgttccggct gtcagcgcag gggcgcccgg ttctttttgt caagaccgac  10560
ctgtccggtg ccctgaatga actgcaggac gaggcagcgc ggctatcgtg gctggccacg  10620
acgggcgttc cttgcgcagc tgtgctcgac gttgtcactg aagcgggaag ggactggctg  10680
ctattgggcg aagtgccggg gcaggatctc ctgtcatctc accttgctcc tgccgagaaa  10740
gtatccatca tggctgatgc aatgcggcgg ctgcatacgc ttgatccggc tacctgccca  10800
ttcgaccacc aagcgaaaca tcgcatcgag cgagcacgta ctcggatgga agccggtctt  10860
gtcgatcagg atgatctgga cgaagagcat caggggctcg cgccagccga actgttcgcc  10920
```

-continued

```
aggctcaagg cgcgcatgcc cgacggcgag gatctcgtcg tgacccatgg cgatgcctgc  10980
ttgccgaata tcatggtgga aaatggccgc ttttctggat tcatcgactg tggccggctg  11040
ggtgtggcgg accgctatca ggacatagcg ttggctaccc gtgatattgc tgaagagctt  11100
ggcggcgaat gggctgaccg cttcctcgtg ctttacggta tcgccgctcc cgattcgcag  11160
cgcatcgcct tctatcgcct tcttgacgag ttcttctgag gggatcggca ataaaaagac  11220
agaataaaac gcacgggtgt tgggtcgttt gttcggatca gcttccgatc atattcaata  11280
acccttaata taacttcgta taatgtatgc tatacgaagt tattaggtct gaagaggagt  11340
ttacgtccag ccaagctaac ttggcgcccc cactagggtc gaggagcttg gtaccgagct  11400
cggatccact agtaacggcc gccagtgtgc tggaattcgc ccttgatgaa tgagcctggc  11460
atctggctcc ctgccacggg gtccccagct cccccatcca ggccccccag gcctgatggg  11520
cgctggcctg aggctggcac tgactaggtt ctgtcctcac agcctccaca cagagcccat  11580
ccgtcttccc cttgacccgc tgctgcaaaa acattccctc caatgccacc tccgtgactc  11640
tgggctgcct ggccacgggc tacttcccgg agccggtgat ggtgacctgg gacacaggct  11700
ccctcaacgg gacaactatg accttaccag ccaccaccct cacgctctct ggtcactatg  11760
ccaccatcag cttgctgacc gtctcgggtg cgtgggccaa gcagatgttc acctgccgtg  11820
tggcacacac tccatcgtcc acagactggg tcgacaacaa aaccttcagc ggtaagagag  11880
ggccaagctc agagaccaca gttcccagga gtgccaggct gagggctggc agagtgggca  11940
ggggttgagg gggtgggtgg gctcaaacgt gggaacaccc agcatgcctg gggacccggg  12000
ccaggacgtg gggcaagag gagggcacac agagctcaga gagcccaaca accctcatga  12060
ccaccagctc tcccccagtc tgctccaggg acttcacccc gcccaccgtg aagatcttac  12120
agtcgtcctg cgacggcggc gggcacttcc ccccgaccat ccagctcctg tgcctcgtct  12180
ctgggtacac cccagggact atcaacatca cctggctgga ggacgggcag gtcatggacg  12240
tggacttgtc caccgcctct accacgcagg agggtgagct ggcctccaca caaagcgagc  12300
tcaccctcag ccagaagcac tggctgtcag accgcaccta cacctgccag gtcacctatc  12360
aaggtcacac ctttgaggac agcaccaaga agtgtgcagg tacgttccca cctgccctgg  12420
tggccgccac ggaggccaga gaagaggggc gggtgggcct cacacagccc tccggtgtac  12480
cacagattcc aacccgagag ggtgagcgc ctacctaagc cggcccagcc cgttcgacct  12540
gttcatccgc aagtcgccca cgatcacctg tctggtggtg gacctggcac ccagcaaggg  12600
gaccgtgaac ctgacctggt cccgggccag tgggaagcct gtgaaccact ccaccagaaa  12660
ggaggagaag cagcgcaatg gcacgttaac cgtcacgtcc accctgccgg tgggcacccg  12720
agactggatc gagggggaga cctaccaatg cagggtgacc cacccccacc tgcccagggc  12780
cctcatgcgg tccacgacca agaccagcgg tgagccatgg gcaggccggg gtcgtggggg  12840
aagggaggga gcgagtgagc ggggcccggg ctgaccccac gtctggccac aggcccgcgt  12900
gctgccccgg aagtctatgc gtttgcgacg ccggagtggc cggggagccg ggacaagcgc  12960
accctcgcct gcctgatcca gaacttcatg cctgaggaca tctcggtgca gtggctgcac  13020
aacgaggtgc agctcccgga cgcccggcac agcacgacgc agccccgcaa gaccaagggc  13080
tccggcttct tcgtcttcag ccgcctggag gtgaccaggg ccgaatggga gcagaaagat  13140
gagttcatct gccgtgcagt ccatgaggca gcgagcccct cacagaccgt ccagcgagcg  13200
gtgtctgtaa atcccggtaa atgacgtact cctgcctccc tccctcccag ggctccatcc  13260
agctgtgcag tggggaggac tggccagacc ttctgtccac tgttgcaatg accccaggaa  13320
```

-continued

```
gctaccccca ataaactgtg cctgctcaga gccccaggta cacccattct tgggagcggg  13380
cagggctgtg ggcaggtgca tcttggcaca gaggaatggg ccccccagga ggggcagtgg  13440
gaggaggtgg gcagggctga gtccccccag gagaggtggt gggaggaggt gggcaggggt  13500
gaggtgccac tcatccatct gccttcgtgt cagggttatt tgtcaaacag catatctgca  13560
gggactcatc acagctaccc cggcctctc tgcccccact ctgggtctac cccctccaag  13620
gagtccaaag acccagggga ggtcctcagg gaaggggcaa gggagccccc acagccctcc  13680
ctcttggggg cttggcttct accccctgg acaggagccc ctgcaccccc aggtatagat  13740
gggcacacag gcccctccag gtggaaaaac agccctaagt gaaaccccca cacagacaca  13800
cacaacccga cagccctcgc ccaagtctgt gccactggcg ttcgcctctc tgccctgtcc  13860
cgccttgccg agtcctggcc ccagcaccgg ggccggtgga gccgagccca ctcacacccc  13920
gcagcctccg ccaccctgcc ctgtgggcac accaggccca ggtcagagcc aggccccctc  13980
tcctactgcc ccccaccgcc ccttggtcca tcctgaatcg gcctccaggg gatcgccagc  14040
ctcacacacc cggtctcgcc cactcacgcc tcactcaagg cacagctgtg cacacactag  14100
gccccatagc aactccacag caccctgtac caccaccagg gcgccataga caccccacac  14160
gtggtcacac gtggcccaca ctccgcctct cacgctgcct ccagccaggc tactgccaag  14220
cccttcctct gagccatacc tgggccgctg gatcccagag agaaatggag aggccctcac  14280
gtggtgtcct ccagtccaac cctccctgtc accctgtcag cagcacccca cagccaaaca  14340
caggatggat gcgtgggctc catcccccac tcacccacac ctgaacccca gagcaggcta  14400
cgtgcccctc acagacctca aacccacatg tgcatctgac accccagatc caaacgctcc  14460
ccccggtcat gcacaccaag ggcacagcac ccaccaaatc cacacggaaa cacgggcacc  14520
gggcacccca tgagcacaaa gcccctccat gtctgaagac agtccctgca caccgtcaca  14580
gccatacatt cagcttcact ctcacgtccc agcccacctg cacccagctc tgggcctgga  14640
gcagcagaaa gaggtgtgag ggcccgaggc cggacctgca cctgctgatg acccgggacc  14700
agcaggcagc tcacggtgtt ggggaaggga gtggagggca cccagggcag gagccagagg  14760
gaccaggctg gtgggcgggg ccgggccggg gtagggccag gaggcagctc tggacaccca  14820
caggcctggg ctcatagtcc acaccaggac agcccctcag agcacccatg cagtgagtcc  14880
caggtcttgg gagccaggcc gcagagctca cgcatccttc cgagggccct gagtgaggcg  14940
gccactgctg cgccgagggg ttgggtcctt ctctggggag ggcgtggggt ctagagaggc  15000
ggagtggagg taaccagagg tcaggagaga agccgtaagg aacagaggga aaatggggcc  15060
agagtcgggg cgcagggacg agaggtcagg agtggtcggc ctggccctgg gccgttgact  15120
gactcgggac ctgggtgccc accctcaggg ctggctggcg gctccgcgca gtcccagagg  15180
gccccggata gggtgctctg ccactccgga cagcagcagg gactgccgag agcggcagga  15240
ggctctgtcc cccacccccg ctgccactgt ggagccggga gggctgactg gccaggtccc  15300
ccagagctgg acgtgtgcgt ggaggaggcc gagggcgagg cgccgtggac gtggaccggc  15360
ctctgcatct tcgccgcact cttcctgctc agcgtgagct acagcgccgc cctcacgctc  15420
ctcatggtgg gcacccacct ccaggggccc agccagggca gggggttggg cagagccagc  15480
agagcgccct gacccacgcc ctcccctcag gtgcagcggt tcctctcagc cacgcggcag  15540
gggaggcccc agacctccct cgactacacc aacgtcctcc agccccacgc ctaggccgcg  15600
ggccactcac gctccaccag gcccagcttt ttctctgcca gcgcctgagc ctccctcggg  15660
```

```
ctgcaccctg ccctgggtgg gaaaagggaa gcagacaaga aaagggggca caaggtcact  15720
actgtgggct gatggccagt gaacctgagc ccagaggggc cggctcagcc gcaaggttac  15780
aggcgccgag agaaccacca gtcgcagccc ccacccgaaa accgtgtctg tcccttcaac  15840
agagtcatcg aggaggggtg gctgctagcc gttctgagct catcgaaggg cgaattctgc  15900
agatatccat cacactggcg gccgctcgac ctaggatctc ctgtctgaca ggaggcaaga  15960
agacagattc ttacccctcc atttctcttt tatccctctc tggtcctcag agagtcagtc  16020
cttcccaaat gtcttccccc tcgtctcctg cgagagcccc ctgtctgata agaatctggt  16080
ggccatgggc tgcctggccc gggacttcct gcccagcacc atttccttca cctggaacta  16140
ccagaacaac actgaagtca tccagggtat cagaaccttc ccaacactga ggacaggggg  16200
caagtaccta gccacctcgc aggtgttgct gtctcccaag agcatccttg aaggttcaga  16260
tgaataccctg gtatgcaaaa tccactacgg aggcaaaaac agagatctgc atgtgcccat  16320
tccaggtaag aaccaaaccc tcccagcagg ggtgcccagg cccaggcatg gcccagaggg  16380
agcagcgggt ggggcttagg ccaagctgag ctcacacctt gacctttcat tccagctgtc  16440
gcagagatga accccaatgt gttcgtccca ccacgggatg gcttctctgg ccctgcacca  16500
cgcaagtcta aactcatctg cgaggccacg aacttcactc caaaaccgat cacagtatcc  16560
tggctaaagg atgggaagct cgtggaatct ggcttcacca cagatccggt gaccatcgag  16620
aacaaaggat ccacacccca aacctacaag gtcataagca cacttaccat ctctgaaatc  16680
gactggctga acctgaatgt gtacacctgc cgtgtggatc acaggggtct caccttcttg  16740
aagaacgtgt cctccacatg tgctgccagt gagtggcctg ggataagccc aatgcctagc  16800
cctcccagat tagggaagtc ctcctacaat tatggccaat gccacccaga catggtcatt  16860
tgctccttga actttggctc cccagagtgg ccaaggacaa gaatgagcaa taggcagtag  16920
aggggtgaga atcagctgga aggaccagca tcttccctta agtaggtttg ggggatggag  16980
actaagcttt tttccaactt cacaactaga tatgtcataa cctgacacag tgttctcttg  17040
actgcaggtc cctccacaga catcctaacc ttcaccatcc ccccctcctt tgccgacatc  17100
ttcctcagca agtccgctaa cctgacctgt ctggtctcaa acctggcaac ctatgaaacc  17160
ctgaatatct cctgggcttc tcaaagtggt gaaccactgg aaaccaaaat taaaatcatg  17220
gaaagccatc ccaatggcac cttcagtgct aagggtgtgg ctagtgtttg tgtggaagac  17280
tggaataaca ggaaggaatt tgtgtgtact gtgactcaca gggatctgcc ttcaccacag  17340
aagaaattca tctcaaaacc caatggtagg tatccccccct tcccttcccc tccaattgca  17400
ggacccttcc tgtacctcat agggagggca ggtcctcttc caccctatcc tcactactgt  17460
cttcatttac agaggtgcac aaacatccac ctgctgtgta cctgctgcca ccagctcgtg  17520
agcaactgaa cctgagggag tcagccacag tcacctgcct ggtgaagggc ttctctcctg  17580
cagacatcag tgtgcagtgg cttcagagag ggcaactctt gccccaagag aagtatgtga  17640
ccagtgcccc gatgccagag cctggggccc caggcttcta ctttacccac agcatcctga  17700
ctgtgacaga ggaggaatgg aactccggag agacctatac ctgtgttgta ggccacgagg  17760
ccctgccaca cctggtgacc gagaggaccg tggacaagtc cactggtaaa cccacactgt  17820
acaatgtctc cctgatcatg tctgacacag gcggcacctg ctattgacca tgctagcgct  17880
caaccaggca ggccctgggt gtccagttgc tctgtgtatg caaactaacc atgtcagagt  17940
gagatgttgc attttataaa aattagaaat aaaaaaaatc cattcaaacg tcactggttt  18000
tgattataca atgctcatgc ctgctgagac agttgtgttt tgcttgctct gcacacaccc  18060
```

```
tgcatacttg cctccaccct ggcccttcct ctaccttgcc agtttcctcc ttgtgtgtga  18120
actcagtcag gcttacaaca gacagagtat gaacatgcga ttcctccagc tacttcttga  18180
tatatggctg aaagcttgcc taacctggtg caggcagcat tcaggcacat atatagacac  18240
acatgcattt atacatagat atataggtac acatgtgtag acacatacat gaatgtgtat  18300
tcatggacac acagacaaag gtacacatat atacacatga gttcatgcgc acacacatgc  18360
atggacactt acaaacgcct tcagagacaa ataggcatag acacacaacc actcacagaa  18420
acagatacca atatgcatgg tcctgtgtac acagaaacag actataggca aatatacaca  18480
aataaactat atagatacaa agatatgcat atacacacat gtacagaaac atcttcacat  18540
gtgtacacta acatgtggac aggtatagca cacagataca cctggactct gaccagggct  18600
gtaatctcca aggctcacgg ctcagagagc ctacactagg ctgggtcact gatactcctc  18660
aggagcccac tctatgattg ggagagataa ccccaggtac aaagtatgcc tatctgtctc  18720
aacaccatgg ggcagaagat actccactaa ccacccatga cagaaagtta gccttggctg  18780
tgtctccatt aatagaacac ctcagaagac caatgtgaaa ttgcctaacc cactcacacc  18840
caccctgatc tccagttcaa aatgcagaaa acataatgca gttgtccaaa agatgcccca  18900
accacacaca cacacacaca cacacacaca cacacacaca cacacacaca cacacacaca  18960
caccatcaag gagcctctgt aaggagtcac cacccaataa cactgcctct ttgggctcat  19020
atcctggaca ttcttcatat tcatatccat ttggggccta ggctttagat atccccaagg  19080
gctcatcttt acagggatca gagatcccaa taaatgccct ggtcccacag cctccctcag  19140
gtatctgtct gtttatctct tggtaccaag acccaacatt gctggcaggg gtaggacaag  19200
caacgcacgg gaactctgat caaagaaagt catgagatgc ctgagtcctt caggaagtaa  19260
ggagggacaa cctctggtat ccctgttctt attgctaaag cccaagagac agggagacct  19320
gctctaaatt ctcagtctaa acagcaccga tggcaccacc tgctcaggga aagtccagag  19380
cacaccaata tcattttgcc acagttcctg agtctgcctt tacccaggtc catacattgc  19440
atctgtcttg cttgctctgc tgccccaggg ctcctggaac aaaggctcca aattagtgtg  19500
tcctacagct tggcctgttc tgtgcctccg tctagcttga gctattaggg gaccagtcaa  19560
tactcgctaa gattctccag aaccatcagg gcaccccaac ccttatgcaa atgctcagtc  19620
accccaagac ttggcttgac cctccctctc tgtgtccctt catagagggg gaggtgaatg  19680
ctgaggagga aggctttgag aacctgtgga ccactgcctc caccttcatc gtcctcttcc  19740
tcctgagcct cttctacagc accaccgtca ccctgttcaa ggtagtatgg ttgtggggct  19800
gaggacacag ggctgggaca gggagtcacc agtcctcact gcctctacct ctactcccta  19860
caagtggaca gcaattcaca ctgtctctgt cacctgcagg tgaaatgact ctcagcatgg  19920
aaggacagca gagaccaaga gatcctccca cagggacact acctctgggc ctgggatacc  19980
tgactgtatg actagtaaac ttattcttac gtctttcctg tgttgccctc cagcttttat  20040
ctctgagatg gtcttctttc tagactgacc aaagactttt tgtcaacttg tacaatctga  20100
agcaatgtct ggcccacaga cagctgagct gtaaacaaat gtcacatgga aataaatact  20160
ttatcttgtg aactcacttt attgtgaagg aatttgtttt gtttttcaaa cctttcctgc  20220
ggtgttgaca gcccaaggat tatctgaata gagcttagga actggaaatg gaacagtgca  20280
gtctgatggt acttaaggga gaaagaggga aaggaggtgt ggaagaagaa aaaagagaag  20340
cagaggggga ggggagaagg gagagggaga gggagaggga gagggagagg gagagggaga  20400
```

```
gggagagaga gagagagaga gagagagaga gagagagcat gcactctaac agcaaagtac  20460

aacacaggca gccaatggat aacactctgg ttatctaccc tgatggaaga agggaagtag  20520

ggcagagaaa attccaggcc taatctccca aaagcaacag aacctggaaa ctagcctcta  20580

gccttaggtc tctgctctgt ccccagccca ccatcttggg ctggtgttgc ttcaagctag  20640

taatttaggt cttatcccaa agctttgtgg tatgtgggtg tgcctttggg gagttggctg  20700

agattttgaa gatgtttgta cctctcccac aacatgacaa gccctagggg ttagtcaata  20760

actcaaattc tctgtctatg acaactgctg tatgactata tgaagaaatg ggataaagat  20820

gctatagtca ctcgag                                                  20836
```

<210> SEQ ID NO 10
<211> LENGTH: 23669
<212> TYPE: DNA
<213> ORGANISM: artificial sequence
<220> FEATURE:
<223> OTHER INFORMATION: synthetic polynucleotide (targeting vector)

<400> SEQUENCE: 10

```
agcgcgcgta atacgactca ctatagggcg aattggagct ccaccgcggt ggcggccgct     60

cctgagagaa cagactctgg aaatagatgg gacttaagga gctaagatct agagctcatc    120

tacagagcag aatcccagcc aagagaacaa agaatactgg ctctctctcc tgttccctac    180

tcctagagtt ctaaaacaca ctatagggaa gggagcctct agacctccgt ccattcccca    240

tcttgctcat tccatcttcc catgtcccca ggtctccaag ccacagacac tacctttcct    300

attcacccac ctttctgtgt ccctaggtcc ccaggccata gtcacctccc cccacacaca    360

ccccactcac cctgccccat ctatgcccct agatgcttac ttaccagagt cttttgtctg    420

acgtggggct acaagcatct atgctcccta agcacctact gctgacctgt aggacccagc    480

tctgaaccaa ctcatataag taaatacaga ctctcccctg tcttaggatg gcctcctgga    540

tcaggaggag accactgcca aagaaccttc tctcagagca ctgaactcct cccctgtacc    600

acttaggaca gacctgagac ctattattac tgattaccag agctctggca gtgaccacgg    660

aggagatagg tccaccctgg acacaggaaa cacagcagca gagatactgc tccatcacaa    720

cagtagagtg acactttaga ctttaatttg ggtcactttc ctgctgcaga ggtgggatca    780

gaaagcaaag agcagtatga gtgcctgata ggcacccaag tacactatag agtactcatg    840

gtgaataagg tacctccatg gcttcccagg gaggggcagc ccccaccccca ccatcacaga    900

cctttctcca tagttgataa ctcagacaca agtgaatgac agatggacct ccatctactc    960

ttattttaaa aagaagacaa accccacagg ctcgagaact ttagcgactg ttttgagaga   1020

aatcattggt ccctgactca agagatgact ggcagattgg ggatcagaat acccatactc   1080

tgtggctagt gtgaggttta agcctcagag tccctgtggt ctctgactgg tgcaaggttt   1140

tgactaagcg gagcaccaca gtgctaactg ggaccacggt gacacgtggc tcaacaaaaa   1200

ccttctgttt ggagctctcc aggggcagcc tgagctatga ggaagtagag aggcttgaga   1260

aatctgagga agaaaagagt agatctgaga ggaaaggtag ctttctggag gtcaggagac   1320

agtgcagaga agaacgagtt actgtggaca ggtcttagat ggggaaagaa tgagcaaatg   1380

caagcatcag aagggtggat gcaatgtcct gccaaggact taccaagagg atccccggac   1440

agagcaggca ggtggagttg actgagagga cagggtaggt gcaggtccct ctctcgtttc   1500

ctttctcctt ctcctgtttc cttcctctct tgtcacaggt ctcactatgc tagccaaggc   1560

tagcctgaaa gattaccatc ctacagatgg gcccatccag ttgagttaag gtggagatct   1620
```

-continued

```
ctccaaacat ctgagtttct gaggcttgga tgccactggg gacgccaagg gactttgggc   1680
tgggtttggt tggccccaga tgaagggcta cttcactggg tctataatta ctctgatgtc   1740
taggaccagg gggctcaggt cactcaggtc aggtgagtcc tgcatctggg gactgtgggg   1800
ttcaggtgtc ctaaggcagg atgtggagag agttttagta taggaacaga ggcagaacag   1860
agactgtgct actggtactt cgatgtctgg ggcgcaggga ccacggtcac cgtctcctca   1920
ggtaagctgg ctttttttctt tctgcacatt ccattctgaa atgggaaaag atattctcag   1980
atctccccat gtcaggccat ctgccacact ctgcatgctg cagaagcttt tctgtaagga   2040
tagggtcttc actcccagga aaagaggcag tcagaggcta gctgcctgtg gaacagtgac   2100
aatcatggaa aataggcatt tacattgtta ggctacatgg gtagatgggt ttttgtacac   2160
ccactaaagg ggtctatgat agtgtgacta ctttgactac tggggccaag gcaccactct   2220
cacagtctcc tcaggtgagt ccttacaacc tctctcttct attcagctta aatagatttt   2280
actgcatttg ttgggggggga aatgtgtgta tctgaatttc aggtcatgaa ggactaggga   2340
caccttggga gtcagaaagg gtcattggga gccctggctg acgcagacag acatcctcag   2400
ctcccatact tcatggccag agatttatag ggatcctggc cagcattgcc gctaggtccc   2460
tctcttctat gctttctttg tccctcactg gcctccatct gagataatcc tggagcccta   2520
gccaaggatc atttattgtc aggggtctaa tcattgttgt cacaatgtgc ctggtttgct   2580
tactggggcc aagggactct ggtcactgtc tctgcaggtg agtcctaact tctcccattc   2640
taaatgcatg ttgggggggat tctgagcctt caggaccaag attctctgca aacgggaatc   2700
aagattcaac ccctttgtcc caaagttgag acatgggtct gggtcaggga ctctctgcct   2760
gctggtctgt ggtgacatta gaactgaagt atgatgaagg atctgccaga actgaagctt   2820
gaagtctgag gcagaatctt gtccagggtc tatcggactc ttgtgagaat taggggctga   2880
cagttgatgg tgacaatttc agggtcagtg actgtctggt ttctctgagg tgaggctgga   2940
atataggtca ccttgaagac ttaagagggg tccagggggc ttctgcacag gcagggaaca   3000
gaatgtggaa caatgacttg aatggttgat tcttgtgtga caccaggaat tggcataatg   3060
tctgagttgc ccaggggtga ttctagtcag actctggggt ttttgtcggg tatagaggaa   3120
aaatccacta ttgtgattac tatgctatgg actactgggg tcaaggaacc tcagtcaccg   3180
tctcctcagg taagaatggc ctctccaggt ctttattttt aacctttgtt atggagtttt   3240
ctgagcattg cagactaatc ttggatattt gtccctgagg gagccggctg agagaagttg   3300
ggaaataaac tgtctaggga tctcagagcc tttaggacag attatctcca catctttgaa   3360
aaactaagaa tctgtgtgat ggtgttggtg gagtccctgg atgatgggat agggactttg   3420
gaggctcatt tgagggagat gctaaaacaa tcctatggct ggagggatag ttggggctgt   3480
agttggagat tttcagtttt tagaataaaa gtattagctg cggaatatac ttcaggacca   3540
cctctgtgac agcatttata cagtatccga tgcataggga caaagagtgg agtggggcac   3600
tttctttaga tttgtgagga atgttccaca ctagattgtt taaaacttca tttgttggaa   3660
ggagagctgt cttagtgatt gagtcaaggg agaaaggcat ctagcctcgg tctcaaaagg   3720
gtagttgctg tctagagagg tctggtggag cctgcaaaag tccagctttc aaaggaacac   3780
agaagtatgt gtatggaata ttagaagatg ttgcttttac tcttaagttg gttcctagga   3840
aaaatagtta aatactgtga ctttaaaatg tgagagggtt ttcaagtact cattttttta   3900
aatgtccaaa atttttgtca atcaatttga ggtcttgttt gtgtagaact gacattactt   3960
```

-continued

```
aaagtttaac cgaggaatgg gagtgaggct ctctcataac ctattcagaa ctgactttta   4020
acaataataa attaagtttc aaatattttt aaatgaattg agcaatgttg agttggagtc   4080
aagatggccg atcagaacca gaacacctgc agcagctggc aggaagcagg tcatgtggca   4140
aggctatttg gggaagggaa aataaaacca ctaggtaaac ttgtagctgt ggtttgaaga   4200
agtggttttg aaacactctg tccagcccca ccaaaccgaa agtccaggct gagcaaaaca   4260
ccacctgggt aatttgcatt tctaaaataa gttgaggatt cagccgaaac tggagaggtc   4320
ctcttttaac ttattgagtt caacctttta attttagctt gagtagttct agtttcccca   4380
aacttaagtt tatcgacttc taaaatgtat ttagaattca ttttcaaaat taggttatgt   4440
aagaaattga aggactttag tgtctttaat ttctaatata tttagaaaac ttcttaaaat   4500
tactctatta ttcttccctc tgattattgg tctccattca attcttttcc aatacccgaa   4560
gcatttacag tgactttgtt catgatcttt tttagttgtt tgttttgcct tactattaag   4620
actttgacat tctggtcaaa acggcttcac aaatcttttt caagaccact ttctgagtat   4680
tcattttagg agaaagactt tttttttaaa tgaatgcaat tatctagact tatttcagtt   4740
gaacatgctg gttggtggtt gagaggacac tcagtcagtc agtggcgtga agggcttcta   4800
agccagtcca catgctctgt gtgaactccc tctggccctg cttattgttg aatgggccaa   4860
aggtctgaga ccaggctgct gctgggtagg cctggacttt gggtctccca cccagacctg   4920
ggaatgtatg gttgtggctt ctgccaccca tccacctggc tgctcatgga ccagccagcc   4980
tcggtggctt tgaaggaaca attccacaca aagactctgg acctctccga aaccaggcac   5040
cgcaaatggt aagccagagg cagccacagc tgtggctgct gctcttaaag cttgtaaact   5100
gtttctgctt aagagggact gagtcttcag tcattgcttt aggggagaa agagacattt   5160
gtgtgtcttt tgagtaccgt tgtctgggtc actcacattt aactttcctt gaaaaactag   5220
actcgacatc gattgtcgag gaattccgat catattcaat aacccttaat ataacttcgt   5280
ataatgtatg ctatacgaag ttattaggtc tgaagaggag tttacgtcca gccttcgaag   5340
ggtcctcagg gagtgcatcc gccccaaccc ttttccccct cgtctcctgt gagaattccc   5400
cgtcggatac gagcagcgtg gccgttggct gcctcgcaca ggacttcctt cccgactcca   5460
tcactttctc ctggaaatac aagaacaact ctgacatcag cagcacccgg ggcttcccat   5520
cagtcctgag agggggcaag tacgcagcca cctcacaggt gctgctgcct tccaaggacg   5580
tcatgcaggg cacagacgaa cacgtggtgt gcaaagtcca gcaccccaac ggcaacaaag   5640
aaaagaacgt gcctcttcca ggtgagggcc gggcccagcc accgggacag agagggagcc   5700
gaagggggc gggagtggcg ggcaccgggc tgacacgtgt ccctcactgc agtgattgct   5760
gagctgcctc ccaaagtgag cgtcttcgtc ccaccccgcg acggcttctt cggcaacccc   5820
cgcaagtcca agctcatctg ccaggccacg ggtttcagtc cccggcagat tcaggtgtcc   5880
tggctgcgcg aggggaagca ggtggggtct ggcgtcacca cggaccaggt gcaggctgag   5940
gccaaagagt ctgggcccac gacctacaag gtgaccagca cactgaccat caaagagagc   6000
gactggctca gccagagcat gttcacctgc cgcgtggatc acaggggcct gaccttccag   6060
cagaatgcgt cctccatgtg tgtccccggt gagtgacctg tccccagggg cagcacccac   6120
cgacacacag gggtccactc gggtctggca ttcgccaccc cggatgcagc catctactcc   6180
ctgagccttg gcttcccaga gcggccaagg gcaggggctc gggcggcagg accccctgggc  6240
tcggcagagg cagttgctac tctttgggtg ggaaccatgc ctccgcccac atccacacct   6300
gccccacctc tgactccctt ctcttgactc cagatcaaga cacagccatc cgggtcttcg   6360
```

```
ccatcccccc atcctttgcc agcatcttcc tcaccaagtc caccaagttg acctgcctgg   6420
tcacagacct gaccacctat gacagcgtga ccatctcctg gacccgccag aatggcgaag   6480
ctgtgaaaac ccacaccaac atctccgaga gccaccccaa tgccactttc agcgccgtgg   6540
gtgaggccag catctgcgag gatgactgga attccgggga gaggttcacg tgcaccgtga   6600
cccacacaga cctgccctcg ccactgaagc agaccatctc ccggcccaag ggtaggcccc   6660
actcttgccc ctcttctgca ctcctgcaac tccttgcctc tgggggcatg gtggaaagca   6720
cccctcactc cccgttgtc tgggcaactg gggaaaaggg gactcaaccc cagcccacag    6780
gctggtcccc ccactgcccc gccctcacca ccatctctgt tcacaggggt ggccctgcac   6840
aggcccgatg tctacttgct gccaccagcc cgggagcagc tgaacctgcg ggagtcggcc   6900
accatcacgt gcctggtgac gggcttctct cccgcggacg tcttcgtgca gtggatgcag   6960
agggggcagc ccttgtcccc ggagaagtat gtgaccagcg ccccaatgcc tgagccccag   7020
gccccaggcc ggtacttcgc ccacagcatc ctgaccgtgt ccgaagagga atggaacacg   7080
ggggagacct acacctgcgt ggtggcccat gaggccctgc ccaacagggt caccgagagg   7140
accgtggaca agtccaccgg taaacccacc ctgtacaacg tgtccctggt catgtccgac   7200
acagctggca cctgctactg accctgctgg cctgcccaca ggctcggggc ggctggccgc   7260
tctgtgtgtg catgcaaact aaccgtgtca acggggtgag atgttgcatc ttataaaatt   7320
agaaataaaa agatccattc aaaagatact ggtcctgagt gcacgatgct ctggcctact   7380
ggggcggcgg ctgtgctgca cccaccctgc gcctcccctg cagaacacct tcctccacag   7440
cccccacccc tgcctcaccc acctgcgtgc ctcagtggct tctagaaacc cctgaattcc   7500
ctgcagctgc tcacagcagg ctgacctcag acttgccatt cctcctactg cttccagaaa   7560
gaaagctgaa agcaaggcca cacgtataca ggcagcacac aggcatgtgt ggatacacat   7620
ggacagacac ggacacacac aaacacatgg acacacagag acgtgctaac ccatgggcac   7680
acacatacac agacatggac ccacacacaa acatatgtgg acacacatgt acaaacatgc   7740
acaggcacac aaagagaaca ctgactacag gcacacacac acacgggcac acacatggat   7800
atgtgcacac atggacacat acatgtgcag gacatgcaca cacacagaca cactagcaca   7860
gaggcataca cacacagaca cacacattca caaacacaca tgtgcatgca aacacacaca   7920
catgtacaga cacgagtaca tggacacatg cacacccaga gacacactga cacagacaca   7980
caggagcatg tgatacacta acacgtggac acacacgtct acccacaggc acacaacaga   8040
tggacacgcg tacacagaca tgcacacacc cacaggcaca acacgtgcgc atgccggccg   8100
gcccccgccc acattctccc agggccctgc cggatactct gtccctgcag cagtttgctc   8160
cctgcgctgt gctggccccg gggctttggg cccaggctct gcttgtcctt ctgtctctgc   8220
ttggaggtgc tgccatggca cccagcttgg gctctgcctg gggagcggag gccccaggga   8280
tagcatgtga cccctgctga ggccaggctc ctgatgaagg cagcagatag cccccacacc   8340
caccggtgag cagaaccaga gcctgtgcca tgtgctgaga gcaggcagtg actaagcata   8400
tgggcccaga gggcagagtg gctgccctgg gcagctgctc ctcttagcgg gaggcctcag   8460
gagatgagct agagcaagtc tgcccctgca aataccacct gctccccaac ccacagcagg   8520
gagcaggcga ggtcagacag cagcagcccg ggaaggaccg agccccagca gggaaggcag   8580
ggcccgagtg aggtctccac acccaacgca cagtgctgtc tctaactggg gccacctccg   8640
agtccccgcc acactcttgg ccctttggag tcctgggctc caggtgtctc ccaagggccc   8700
```

```
atctgtgcag gggatgcaac cccccgaatg tcctcatccc actgtggagc tcaggtctct   8760
gtctgctccc tgggtcctgg cagggtagga caagtccgcc aggatgtccc catgcagact   8820
ctgctccaag agggagctgg agagtcaggg ccttggtgag ggagtcagga tcgggttccc   8880
cccagctcag tcctcccacc tgccagcccc cacagcacag ggcagggcca cacccccctgc   8940
ttccccctcc aggagagtca ggacatgctg gccgctgctc cgctggggcc ccgccctcca   9000
gcccccacct tggtctgtgt gctgcatccc ccacgctctc tctgccaccc caggactctg   9060
aggaaaagac ctcagagtcc cagccctgcc cagtctcggc ctgtgccccc gctgcatcag   9120
gctttcaggg gcccagccca tgccctgggc agtgcccgag cccccctgca cttgctctcc   9180
ccacccctgg gtgcagcaca gcctaggggc caagggtggg cctagaggat gggccccggg   9240
ggggctttgc tgggtgccac cccagcctga ccctattccc ccgtgctgtg tctcctgcag   9300
agggggaggt gagcgccgac gaggagggct ttgagaacct gtgggccacc gcctccacct   9360
tcatcgtcct cttcctcctg agcctcttct acagtaccac cgtcaccttg ttcaaggtag   9420
cacggctgtg gcacagggag gagggtgcag ggcgagtgtg gggcccaggg agcagcctgg   9480
gctggacgtc tagcccggag gcccccacac caccccactg ggtcatctct gccccggctc   9540
ccttccccgac cacggggaaa gcatttcaca ctgtctctgt tgcctgtagg tgaaatgatc   9600
ccaacagaag aacatcggag accagagaga ggaactcaaa ggggcgctgc ctccgggtct   9660
ggggtcctgg cctgcgtggc ctgttggcac gtgtttctct tccccgcccg gcctccagtt   9720
gtgtgctctc acacaggctt ctttctcgac cggcaggggc tggctggctt gcaggccacg   9780
aggtggggct ctaccccaca ctgctttgct gtgtatacgc ttgttgcctg aaataaatat   9840
gcacatttta tccatgaaac tgctttctgg tgagggtttg tttctttttc aaaactttcc   9900
tgctacaggg cattcaagcc atcgatgtcg aggaattccg atcatattca ataaccctta   9960
atataacttc gtataatgta tgctatacga agttattagg tctgaagagg agtttacgtc  10020
cagccaagct agcttggctg caggtcgagc agtgtggttt tcaagaggaa gcaaaaagcc  10080
tctccaccca ggcctggaat gtttccaccc aatgtcgagc agtgtggttt tgcaagagga  10140
agcaaaaagc ctctccaccc aggcctggaa tgtttccacc caatgtcgag cagtgtggtt  10200
ttgcaagagg aagcaaaaag cctctccacc caggcctgga atgtttccac ccaatgtcga  10260
gcaaaccccg cccagcgtct tgtcattggc gaattcgaac acgcagatgc agtcggggcg  10320
gcgcggtccc caggtccact tcgcatatta aggtgacgcg tgtggcctcg aacaccgagc  10380
gaccctgcag ccaatatggg atcggccatt gaacaagatg gattgcacgc aggttctccg  10440
gccgcttggg tggagaggct attcggctat gactgggcac aacagacaat cggctgctct  10500
gatgccgccg tgttccggct gtcagcgcag gggcgcccgg ttctttttgt caagaccgac  10560
ctgtccggtg ccctgaatga actgcaggac gaggcagcgc ggctatcgtg gctggccacg  10620
acgggcgttc cttgcgcagc tgtgctcgac gttgtcactg aagcgggaag ggactggctg  10680
ctattgggcg aagtgccggg gcaggatctc ctgtcatctc accttgctcc tgccgagaaa  10740
gtatccatca tggctgatgc aatgcggcgg ctgcatacgc ttgatccggc tacctgccca  10800
ttcgaccacc aagcgaaaca tcgcatcgag cgagcacgta ctcggatgga agccggtctt  10860
gtcgatcagg atgatctgga cgaagagcat caggggctcg cgccagccga actgttcgcc  10920
aggctcaagg cgcgcatgcc cgacggcgag gatctcgtcg tgacccatgg cgatgcctgc  10980
ttgccgaata tcatggtgga aaatggccgc ttttctggat tcatcgactg tggccggctg  11040
ggtgtggcgg accgctatca ggacatagcg ttggctaccc gtgatattgc tgaagagctt  11100
```

ggcggcgaat gggctgaccg cttcctcgtg ctttacggta tcgccgctcc cgattcgcag 11160
cgcatcgcct tctatcgcct tcttgacgag ttcttctgag gggatcggca ataaaaagac 11220
agaataaaac gcacgggtgt tgggtcgttt gttcggatca gcttccgatc atattcaata 11280
acccttaata taacttcgta taatgtatgc tatacgaagt tattaggtct gaagaggagt 11340
ttacgtccag ccaagctaac ttggcgcccc cactagggtc gaggagcttg gtaccgagct 11400
cggatccact agtaacggcc gccagtgtgc tggaattcgc ccttgatgaa tgagcctggc 11460
atctggctcc ctgccacggg gtccccagct cccccatcca ggccccccag gcctgatggg 11520
cgctggcctg aggctggcac tgactaggtt ctgtcctcac agcctccaca cagagcccat 11580
ccgtcttccc cttgacccgc tgctgcaaaa acattccctc caatgccacc tccgtgactc 11640
tgggctgcct ggccacgggc tacttcccgg agccggtgat ggtgacctgg gacacaggct 11700
ccctcaacgg gacaactatg accttaccag ccaccaccct cacgctctct ggtcactatg 11760
ccaccatcag cttgctgacc gtctcgggtg cgtgggccaa gcagatgttc acctgccgtg 11820
tggcacacac tccatcgtcc acagactggg tcgacaacaa aaccttcagc ggtaagagag 11880
ggccaagctc agagaccaca gttcccagga gtgccaggct gagggctggc agagtgggca 11940
ggggttgagg gggtgggtgg gctcaaacgt gggaacaccc agcatgcctg gggacccggg 12000
ccaggacgtg ggggcaagag gagggcacac agagctcaga gagcccaaca accctcatga 12060
ccaccagctc tcccccagtc tgctccaggg acttcacccc gcccaccgtg aagatcttac 12120
agtcgtcctg cgacggcggc gggcacttcc ccccgaccat ccagctcctg tgcctcgtct 12180
ctgggtacac cccagggact atcaacatca cctggctgga ggacgggcag gtcatggacg 12240
tggacttgtc caccgcctct accacgcagg agggtgagct ggcctccaca caaagcgagc 12300
tcaccctcag ccagaagcac tggctgtcag accgcaccta cacctgccag gtcacctatc 12360
aaggtcacac ctttgaggac agcaccaaga agtgtgcagg tacgttccca cctgccctgg 12420
tggccgccac ggaggccaga gaagaggggc gggtgggcct cacacagccc tccggtgtac 12480
cacagattcc aacccgagag ggtgagcgc ctacctaagc cggcccagcc cgttcgacct 12540
gttcatccgc aagtcgccca cgatcacctg tctggtggtg gacctggcac ccagcaaggg 12600
gaccgtgaac ctgacctggt cccgggccag tgggaagcct gtgaaccact ccaccagaaa 12660
ggaggagaag cagcgcaatg gcacgttaac cgtcacgtcc accctgccgg tgggcacccg 12720
agactggatc gagggggaga cctaccaatg cagggtgacc cacccccacc tgcccagggc 12780
cctcatgcgg tccacgacca agaccagcgg tgagccatgg gcaggccggg gtcgtggggg 12840
aagggaggga gcgagtgagc ggggcccggg ctgaccccac gtctggccac aggcccgcgt 12900
gctgccccgg aagtctatgc gtttgcgacg ccggagtggc cggggagccg ggacaagcgc 12960
accctcgcct gcctgatcca gaacttcatg cctgaggaca tctcggtgca gtggctgcac 13020
aacgaggtgc agctcccgga cgcccggcac agcacgacgc agccccgcaa gaccaagggc 13080
tccggcttct tcgtcttcag ccgcctggag gtgaccaggg ccgaatggga gcagaaagat 13140
gagttcatct gccgtgcagt ccatgaggca gcgagcccct cacagaccgt ccagcgagcg 13200
gtgtctgtaa atcccggtaa atgacgtact cctgcctccc tccctcccag ggctccatcc 13260
agctgtgcag tggggaggac tggccagacc ttctgtccac tgttgcaatg accccaggaa 13320
gctaccccca ataaactgtg cctgctcaga gccccaggta cacccattct tgggagcggg 13380
cagggctgtg ggcaggtgca tcttggcaca gaggaatggg ccccccagga ggggcagtgg 13440

-continued

```
gaggaggtgg gcagggctga gtccccccag gagaggtggt gggaggaggt gggcaggggt  13500
gaggtgccac tcatccatct gccttcgtgt cagggttatt tgtcaaacag catatctgca  13560
gggactcatc acagctaccc cgggcctctc tgcccccact ctgggtctac cccctccaag  13620
gagtccaaag acccagggga ggtcctcagg gaaggggcaa gggagccccc acagccctcc  13680
ctcttggggg cttggcttct acccccctgg acaggagccc ctgcacccc aggtatagat  13740
gggcacacag gcccctccag gtggaaaaac agccctaagt gaaaccccca cacagacaca  13800
cacaacccga cagccctcgc ccaagtctgt gccactggcg ttcgcctctc tgccctgtcc  13860
cgccttgccg agtcctggcc ccagcaccgg ggccggtgga gccgagccca ctcacacccc  13920
gcagcctccg ccaccctgcc ctgtgggcac accaggccca ggtcagagcc aggccccctc  13980
tcctactgcc ccccaccgcc ccttggtcca tcctgaatcg gcctccaggg gatcgccagc  14040
ctcacacacc cggtctcgcc cactcacgcc tcactcaagg cacagctgtg cacacactag  14100
gccccatagc aactccacag caccctgtac caccaccagg gcgccataga caccccacac  14160
gtggtcacac gtggcccaca ctccgcctct cacgctgcct ccagccaggc tactgccaag  14220
cccttcctct gagccatacc tgggccgctg gatcccagag agaaatggag aggccctcac  14280
gtggtgtcct ccagtccaac cctccctgtc accctgtcag cagcacccca cagccaaaca  14340
caggatggat gcgtgggctc catcccccac tcacccacac ctgaacccca gagcaggcta  14400
cgtgcccctc acagacctca aacccacatg tgcatctgac accccagatc caaacgctcc  14460
ccccggtcat gcacaccaag ggcacagcac ccaccaaatc cacacggaaa cacgggcacc  14520
gggcacccca tgagcacaaa gcccctccat gtctgaagac agtccctgca caccgtcaca  14580
gccatacatt cagcttcact ctcacgtccc agcccacctg cacccagctc tgggcctgga  14640
gcagcagaaa gaggtgtgag ggcccgaggc cggacctgca cctgctgatg acccgggacc  14700
agcaggcagc tcacggtgtt ggggaaggga gtggagggca cccagggcag gagccagagg  14760
gaccaggctg gtgggcgggg ccgggccggg gtagggccag gaggcagctc tggacaccca  14820
caggcctggg ctcatagtcc acaccaggac agcccctcag agcacccatg cagtgagtcc  14880
caggtcttgg gagccaggcc gcagagctca cgcatccttc cgagggccct gagtgaggcg  14940
gccactgctg cgccgagggg ttgggtcctt ctctggggag ggcgtggggt ctagagaggc  15000
ggagtggagg taaccagagg tcaggagaga agccgtaagg aacagaggga aaatggggcc  15060
agagtcgggg cgcagggacg agaggtcagg agtggtcggc ctggccctgg gccgttgact  15120
gactcgggac ctgggtgccc accctcaggg ctggctggcg gctccgcgca gtcccagagg  15180
gccccggata gggtgctctg ccactccgga cagcagcagg gactgccgag agcggcagga  15240
ggctctgtcc cccacccccg ctgccactgt ggagccggga gggctgactg gccaggtccc  15300
ccagagctgg acgtgtgcgt ggaggaggcc gagggcgagg cgccgtggac gtggaccggc  15360
ctctgcatct tcgccgcact cttcctgctc agcgtgagct acagcgccgc cctcacgctc  15420
ctcatggtgg gcacccacct ccaggggccc agccagggca gggggttggg cagagccagc  15480
agagcgccct gacccacgcc ctcccctcag gtgcagcggt tcctctcagc cacgcggcag  15540
gggaggcccc agacctccct cgactacacc aacgtcctcc agccccacgc ctaggccgcg  15600
ggccactcac gctccaccag gcccagcttt ttctctgcca gcgcctgagc ctccctcggg  15660
ctgcaccctg ccctgggtgg gaaaagggaa gcagacaaga aaagggggca caaggtcact  15720
actgtgggct gatggccagt gaacctgagc ccagaggggc cggctcagcc gcaaggttac  15780
aggcgccgag agaaccacca gtcgcagccc ccacccgaaa accgtgtctg tcccttcaac  15840
```

-continued

```
agagtcatcg aggaggggtg gctgctagcc gttctgagct catcgaaggg cgaattctgc  15900
agatatccat cacactggcg gccgctcgac ctaggatctc ctgtctgaca ggaggcaaga  15960
agacagattc ttacccctcc atttctcttt tatccctctc tggtcctcag agagtcagtc  16020
cttcccaaat gtcttccccc tcgtctcctg cgagagcccc ctgtctgata agaatctggt  16080
ggccatgggc tgcctggccc gggacttcct gcccagcacc atttccttca cctggaacta  16140
ccagaacaac actgaagtca tccagggtat cagaaccttc ccaacactga ggacaggggg  16200
caagtaccta gccacctcgc aggtgttgct gtctcccaag agcatccttg aaggttcaga  16260
tgaatacctg gtatgcaaaa tccactacgg aggcaaaaac agagatctgc atgtgcccat  16320
tccaggtaag aaccaaaccc tcccagcagg ggtgcccagg cccaggcatg gcccagaggg  16380
agcagcgggt ggggcttagg ccaagctgag ctcacacctt gacctttcat tccagctgtc  16440
gcagagatga accccaatgt gttcgtccca ccacgggatg gcttctctgg ccctgcacca  16500
cgcaagtcta aactcatctg cgaggccacg aacttcactc caaaaccgat cacagtatcc  16560
tggctaaagg atgggaagct cgtggaatct ggcttcacca cagatccggt gaccatcgag  16620
aacaaaggat ccacacccca aacctacaag gtcataagca cacttaccat ctctgaaatc  16680
gactggctga acctgaatgt gtacacctgc cgtgtggatc acaggggtct caccttcttg  16740
aagaacgtgt cctccacatg tgctgccagt gagtggcctg ggataagccc aatgcctagc  16800
cctcccagat tagggaagtc ctcctacaat tatggccaat gccacccaga catggtcatt  16860
tgctccttga actttggctc cccagagtgg ccaaggacaa gaatgagcaa taggcagtag  16920
aggggtgaga atcagctgga aggaccagca tcttccctta agtaggtttg ggggatggag  16980
actaagcttt tttccaactt cacaactaga tatgtcataa cctgacacag tgttctcttg  17040
actgcaggtc cctccacaga catcctaacc ttcaccatcc ccccctcctt tgccgacatc  17100
ttcctcagca agtccgctaa cctgacctgt ctggtctcaa acctggcaac ctatgaaacc  17160
ctgaatatct cctgggcttc tcaaagtggt gaaccactgg aaaccaaaat taaaatcatg  17220
gaaagccatc ccaatggcac cttcagtgct aagggtgtgg ctagtgtttg tgtggaagac  17280
tggaataaca ggaaggaatt tgtgtgtact gtgactcaca gggatctgcc ttcaccacag  17340
aagaaattca tctcaaaacc caatggtagg tatccccccct tcccttcccc tccaattgca  17400
ggacccttcc tgtacctcat agggagggca ggtcctcttc caccctatcc tcactactgt  17460
cttcatttac agaggtgcac aaacatccac ctgctgtgta cctgctgcca ccagctcgtg  17520
agcaactgaa cctgagggag tcagccacag tcacctgcct ggtgaagggc ttctctcctg  17580
cagacatcag tgtgcagtgg cttcagagag ggcaactctt gccccaagag aagtatgtga  17640
ccagtgcccc gatgccagag cctggggccc caggcttcta ctttacccac agcatcctga  17700
ctgtgacaga ggaggaatgg aactccggag agacctatac ctgtgttgta ggccacgagg  17760
ccctgccaca cctggtgacc gagaggaccg tggacaagtc cactggtaaa cccacactgt  17820
acaatgtctc cctgatcatg tctgacacag gcggcacctg ctattgacca tgctagcgct  17880
caaccaggca ggccctgggt gtccagttgc tctgtgtatg caaactaacc atgtcagagt  17940
gagatgttgc attttataaa aattagaaat aaaaaaaatc cattcaaacg tcactggttt  18000
tgattataca atgctcatgc ctgctgagac agttgtgttt tgcttgctct gcacacaccc  18060
tgcatacttg cctccaccct ggcccttcct ctaccttgcc agtttcctcc ttgtgtgtga  18120
actcagtcag gcttacaaca gacagagtat gaacatgcga ttcctccagc tacttcttga  18180
```

```
tatatggctg aaagcttgcc taacctggtg caggcagcat tcaggcacat atatagacac  18240
acatgcattt atacatagat atataggtac acatgtgtag acacatacat gaatgtgtat  18300
tcatggacac acagacaaag gtacacatat atacacatga gttcatgcgc acacacatgc  18360
atggacactt acaaacgcct tcagagacaa ataggcatag acacacaacc actcacagaa  18420
acagatacca atatgcatgg tcctgtgtac acagaaacag actataggca aatatacaca  18480
aataaactat atagatacaa agatatgcat atacacacat gtacagaaac atcttcacat  18540
gtgtacacta acatgtggac aggtatagca cacagataca cctggactct gaccagggct  18600
gtaatctcca aggctcacgg ctcagagagc ctacactagg ctgggtcact gatactcctc  18660
aggagcccac tctatgattg ggagagataa ccccaggtac aaagtatgcc tatctgtctc  18720
aacaccatgg ggcagaagat actccactaa ccacccatga cagaaagtta gccttggctg  18780
tgtctccatt aatagaacac ctcagaagac caatgtgaaa ttgcctaacc cactcacacc  18840
caccctgatc tccagttcaa aatgcagaaa acataatgca gttgtccaaa agatgcccca  18900
accacacaca cacacacaca cacacacaca cacacacaca cacacacaca cacacacaca  18960
caccatcaag gagcctctgt aaggagtcac cacccaataa cactgcctct ttgggctcat  19020
atcctggaca ttcttcatat tcatatccat ttggggccta ggctttagat atccccaagg  19080
gctcatcttt acagggatca gagatcccaa taaatgccct ggtcccacag cctccctcag  19140
gtatctgtct gtttatctct tggtaccaag acccaacatt gctggcaggg gtaggacaag  19200
caacgcacgg gaactctgat caaagaaagt catgagatgc ctgagtcctt caggaagtaa  19260
ggagggacaa cctctggtat ccctgttctt attgctaaag cccaagagac agggagacct  19320
gctctaaatt ctcagtctaa acagcaccga tggcaccacc tgctcaggga aagtccagag  19380
cacaccaata tcattttgcc acagttcctg agtctgcctt tacccaggtc catacattgc  19440
atctgtcttg cttgctctgc tgccccaggg ctcctggaac aaaggctcca aattagtgtg  19500
tcctacagct tggcctgttc tgtgcctccg tctagcttga gctattaggg gaccagtcaa  19560
tactcgctaa gattctccag aaccatcagg gcaccccaac ccttatgcaa atgctcagtc  19620
accccaagac ttggcttgac cctccctctc tgtgtccctt catagagggg gaggtgaatg  19680
ctgaggagga aggctttgag aacctgtgga ccactgcctc caccttcatc gtcctcttcc  19740
tcctgagcct cttctacagc accaccgtca ccctgttcaa ggtagtatgg ttgtggggct  19800
gaggacacag ggctgggaca gggagtcacc agtcctcact gcctctacct ctactcccta  19860
caagtggaca gcaattcaca ctgtctctgt cacctgcagg tgaaatgact ctcagcatgg  19920
aaggacagca gagaccaaga gatcctccca cagggacact acctctgggc ctgggatacc  19980
tgactgtatg actagtaaac ttattcttac gtctttcctg tgttgccctc cagcttttat  20040
ctctgagatg gtcttctttc tagactgacc aaagactttt tgtcaacttg tacaatctga  20100
agcaatgtct ggcccacaga cagctgagct gtaaacaaat gtcacatgga aataaatact  20160
ttatcttgtg aactcacttt attgtgaagg aatttgtttt gtttttcaaa cctttcctgc  20220
ggtgttgaca gcccaaggat tatctgaata gagcttagga actggaaatg gaacagtgca  20280
gtctgatggt acttaaggga gaaagaggga aaggaggtgt ggaagaagaa aaaagagaag  20340
cagaggggga ggggagaagg gagagggaga gggagaggga gagggagagg gagagggaga  20400
gggagagaga gagagagaga gagagagaga gagagagcat gcactctaac agcaaagtac  20460
aacacaggca gccaatggat aacactctgg ttatctaccc tgatggaaga agggaagtag  20520
ggcagagaaa attccaggcc taatctccca aaagcaacag aacctggaaa ctagcctcta  20580
```

gccttaggtc tctgctctgt ccccagccca ccatcttggg ctggtgttgc ttcaagctag 20640
taatttaggt cttatcccaa agctttgtgg tatgtgggtg tgcctttggg gagttggctg 20700
agattttgaa gatgtttgta cctctcccac aacatgacaa gccctagggg ttagtcaata 20760
actcaaattc tctgtctatg acaactgctg tatgactata tgaagaaatg ggataaagat 20820
gctatagtca ctcgaggggg ggcccggtac ccagcttttg ttccctttag tgagggttaa 20880
ttgcgcgctt ggcgtaatca tggtcatagc tgtttcctgt gtgaaattgt tatccgctca 20940
caattccaca caacatacga gccggaagca taaagtgtaa agcctggggt gcctaatgag 21000
tgagctaact cacattaatt gcgttgcgct cactgcccgc tttccagtcg ggaaacctgt 21060
cgtgccagct gcattaatga atcggccaac gcgcggggag aggcggtttg cgtattgggc 21120
gctcttccgc ttcctcgctc actgactcgc tgcgctcggt cgttcggctg cggcgagcgg 21180
tatcagctca ctcaaaggcg gtaatacggt tatccacaga atcaggggat aacgcaggaa 21240
agaacatgtg agcaaaaggc cagcaaaagg ccaggaaccg taaaaaggcc gcgttgctgg 21300
cgtttttcca taggctccgc ccccctgacg agcatcacaa aaatcgacgc tcaagtcaga 21360
ggtggcgaaa cccgacagga ctataaagat accaggcgtt tccccctgga agctccctcg 21420
tgcgctctcc tgttccgacc ctgccgctta ccggatacct gtccgccttt ctcccttcgg 21480
gaagcgtggc gctttctcat agctcacgct gtaggtatct cagttcggtg taggtcgttc 21540
gctccaagct gggctgtgtg cacgaacccc ccgttcagcc cgaccgctgc gccttatccg 21600
gtaactatcg tcttgagtcc aacccggtaa gacacgactt atcgccactg gcagcagcca 21660
ctggtaacag gattagcaga gcgaggtatg taggcggtgc tacagagttc ttgaagtggt 21720
ggcctaacta cggctacact agaaggacag tatttggtat ctgcgctctg ctgaagccag 21780
ttaccttcgg aaaaagagtt ggtagctctt gatccggcaa acaaaccacc gctggtagcg 21840
gtggtttttt tgtttgcaag cagcagatta cgcgcagaaa aaaaggatct caagaagatc 21900
ctttgatctt ttctacgggg tctgacgctc agtggaacga aaactcacgt taagggattt 21960
tggtcatgag attatcaaaa aggatcttca cctagatcct tttaaattaa aaatgaagtt 22020
ttaaatcaat ctaaagtata tatgagtaaa cttggtctga cagttaccaa tgcttaatca 22080
gtgaggcacc tatctcagcg atctgtctat ttcgttcatc catagttgcc tgactccccg 22140
tcgtgtagat aactacgata cgggagggct taccatctgg ccccagtgct gcaatgatac 22200
cgcgagaccc acgctcaccg gctccagatt tatcagcaat aaaccagcca gccggaaggg 22260
ccgagcgcag aagtggtcct gcaactttat ccgcctccat ccagtctatt aattgttgcc 22320
gggaagctag agtaagtagt tcgccagtta atagtttgcg caacgttgtt gccattgcta 22380
caggcatcgt ggtgtcacgc tcgtcgtttg gtatggcttc attcagctcc ggttcccaac 22440
gatcaaggcg agttacatga tcccccatgt tgtgcaaaaa agcggttagc tccttcggtc 22500
ctccgatcgt tgtcagaagt aagttggccg cagtgttatc actcatggtt atggcagcac 22560
tgcataattc tcttactgtc atgccatccg taagatgctt ttctgtgact ggtgagtact 22620
caaccaagtc attctgagaa tagtgtatgc ggcgaccgag ttgctcttgc ccggcgtcaa 22680
tacgggataa taccgcgcca catagcagaa ctttaaaagt gctcatcatt ggaaaacgtt 22740
cttcggggcg aaaactctca aggatcttac cgctgttgag atccagttcg atgtaaccca 22800
ctcgtgcacc caactgatct tcagcatctt ttactttcac cagcgtttct gggtgagcaa 22860
aaacaggaag gcaaaatgcc gcaaaaaagg gaataagggc gacacggaaa tgttgaatac 22920

-continued

```
tcatactctt cctttttcaa tattattgaa gcatttatca gggttattgt ctcatgagcg  22980
gatacatatt tgaatgtatt tagaaaaata aacaaatagg ggttccgcgc acatttcccc  23040
gaaaagtgcc acctgacgcg ccctgtagcg gcgcattaag cgcggcgggt gtggtggtta  23100
cgcgcagcgt gaccgctaca cttgccagcg ccctagcgcc cgctcctttc gctttcttcc  23160
cttcctttct cgccacgttc gccggctttc cccgtcaagc tctaaatcgg gggctccctt  23220
tagggttccg atttagtgct ttacggcacc tcgaccccaa aaaacttgat tagggtgatg  23280
gttcacgtag tgggccatcg ccctgataga cggtttttcg ccctttgacg ttggagtcca  23340
cgttctttaa tagtggactc ttgttccaaa ctggaacaac actcaaccct atctcggtct  23400
attcttttga tttataaggg attttgccga tttcggccta ttggttaaaa aatgagctga  23460
tttaacaaaa atttaacgcg aattttaaca aaatattaac gcttacaatt tccattcgcc  23520
attcaggctg cgcaactgtt gggaagggcg atcggtgcgg gcctcttcgc tattacgcca  23580
gctggcgaaa gggggatgtg ctgcaaggcg attaagttgg gtaacgccag ggttttccca  23640
gtcacgacgt tgtaaaacga cggccagtg                                    23669
```

TRANSGENIC NON-HUMAN MAMMAL FOR PRODUCING CHIMERIC HUMAN IMMUNOGLOBULIN E ANTIBODIES

The present invention relates to a transgenic non-human mammal comprising human immunoglobulin mu and epsilon heavy-chain constant transgenes Cμ and Cϵ inserted in place of endogenous mu heavy-chain switch sequence Sμ, and its use for producing chimeric human immunoglobulin E antibodies specific for an antigen of interest.

Human immunoglobulins E (IgE) constitute the most potent class of antibody for triggering very strong immune responses even when present at very low concentrations. IgE also constitute rare reagents only present in minute amounts in human serum and which are of interest for the diagnosis of allergy. However, because they are poorly available they were also rarely studied as potential drug for human therapy, although few reports have documented their efficacy against several targets, including tumor cells (Karagiannis et al., J. Immunol., 2007, 179, 2832-2843; Teo et al., Cancer Immunol. Immunother., 2012, 61, 2295-2309).

Like serum IgE, B cells that express IgE ($IgE^+$ B cells) are so rare, transient and and short-lived in vivo in both human and animals that they are extremely difficult if not almost impossible to detect, identify and extract for studies. For these reasons, the knowledge about B cells that undergo class switch recombination to IgE, their terminal differentiation into IgE-secreting plasma cells and the nature of IgE memory, if any, is very limited and it has never been possible until now to design efficient systems for the production of a large repertoire of human, humanized or chimeric human IgE antibodies.

The isolation of human IgE (hIgE) from patients yields very small amounts of hIgE, and only for a limited type of antigens. In addition, the hIgE produced by said method are potentially hazardous due to possible contamination with human pathogens.

The production of recombinant human IgE comprises cloning the variable region from the heavy chain of a mouse monoclonal antibody specific for an antigen of interest and rearranging it with a human immunoglobulin epsilon heavy chain constant gene Cepsilon. This method is long, costly and produces only one human IgE antibody molecule specific for a particular antigen of interest so that the method needs to be reiterated entirely for each new human IgE antibody molecule specific for a particular antigen of interest.

Humanized transgenic mouse strains comprising from large fragments to complete human immunoglobulin heavy chain (IgH) and kappa light chain (Igκ) loci and inactivated mouse IgH and Igκ loci have been generated and successfully used for generating high-affinity antibodies against various targets (XenoMouse®: Green et al., Nature Genetics, 1994, 7, 13-21; International PCT Application WO 94/02602; Mendez et al., Nature Genetics, 1997, 15, 146-156; Hu-MAb-Mouse®: Lonberg et al., Nature, 1994, 368, 856-859; International PCT Application WO 92/03918; KM MouseTM; Tomizuka et al., Proc. Natl. Acad. Sci. USA, 2004, 97, 722-727; International PCT Application WO 02/43478). However, the frequency of $IgE^+$ B cells in these transgenic mice which is as low as in humans does not allow the production of high amounts of human IgE antibodies.

Transgenic mice in which IgM expression is constitutively turned into IgA or IgG expression have been generated and successfully used for producing chimeric human IgG and IgA antibodies specific for various antigens of interest (International PCT Applications WO 2005/047333 and WO 2009/106773; Duchez et al., Proc. Natl. Acad. Sci. USA, 2010, 107, 3064-3069). However, $IgE^+$ B-cells are so transient and short-lived that it is not possible to construct similar transgenic mice to produce human chimeric IgE antibodies.

The inventors have made a technological breakthrough by designing the first transgenic animals that can be used for generating hybridomas producing high amounts of high affinity chimeric human IgE antibodies of defined specificity, very easily and quickly.

Therefore, the invention relates to a transgenic non-human mammal, which comprises an endogenous immunoglobulin heavy-chain (IgH) locus comprising the replacement of its mu heavy-chain switch sequence Sμ by a human transgenic DNA construct comprising respectively from its 5' to its 3' end, at least:

(a) a first site-specific recombination sequence, a human immunoglobulin mu heavy-chain constant gene Cμ, or a functional fragment thereof, and a second site-specific recombination sequence, said first and said second recombination sequences being in the same orientation and capable of site-specific recombination, and (b) a human immunoglobulin epsilon heavy-chain constant gene Cϵ or a functional fragment thereof, and wherein said transgenic mammal comprises endogenous B-cells which produce chimeric human immunoglobulin M (IgM) class antibodies and no endogenous IgM antibodies from said transgenic mammal, and wherein said B-cells switch chimeric human antibodies class production from immunoglobulin M (IgM) to immunoglobulin E (IgE), following site-specific recombination between said first and second site-specific recombination sequences.

In the present invention:

a "site-specific recombination sequence" refers to a recombination site for a site-specific recombinase.

a "chimeric human antibody" and a "humanized antibody", both refer to an antibody comprising heavy chains with a human constant region and a variable region from said transgenic mammal and light chains in which each of the variable and constant region is human or from said transgenic mammal.

a "functional fragment of a human heavy-chain constant region gene" refers to fragment of said gene which comprises at least human CH1, CH2, CH3 and CH4 exons and human membrane M1 and M2 exons.

In the transgenic mammal of the invention, the human heavy-chain constant genes Cμ (C mu or Cmu) and Cϵ (C epsilon or Cepsilon) which are inserted in place of the switch sequence Sμ (S mu or Smu), are therefore located between the intronic activator Eμ (E mu or Emu) and the endogenous mouse Cμ gene (FIG. 1). The Sμ sequence which is deleted in said transgenic mammal comprises at least positions 136442 to positions 140100 (SEQ ID NO: 1) with reference to mouse chromosome 12 sequence Genbank/EMBL accession number AC073553.

The human Cmu transgene in its original configuration (before site-specific recombination has occurred) and the human Cepsilon transgene, after site-specific recombination has occurred, are operably linked to the endogenous non-human mammal, for example mouse, heavy-chain variable region genes (V, D, J segment genes) and regulatory sequences (promoter, enhancer(s)).

In this transgenic mammals, named as Mu-Epsilon or InEps, the deletion of the endogenous mu heavy-chain switch sequence Smu associated with the insertion of the human Cmu and Cepsilon transgenes in place of this sequence, abolishes the expression of the endogenous Cμ gene responsible for the synthesis of endogenous IgM heavy-chains and reduces drastically the expression of the other endogenous immunoglobulin heavy-chain genes, by disrupting the phenomenon of class switch recombination which is dependent on the Smu region to occur and to change to the class of the expressed immunoglobulin isotype.

The transgenic mammals of the invention produce chimeric human IgMs whose heavy chains comprise a human IgM constant region and a variable region from said transgenic mammal, and no endogenous immunoglobulins M.

The chimeric human antibodies generated by the transgenic mammal, in response to an antigen, benefit from a completely diversified repertoire since their heavy-chains whose variable domain VH mainly contribute to the formation of the antibody site correspond to the normal repertoire generated by the rearrangements of the VH, D and JH segments of the non-human mammal, for example murine, IgH locus.

Following immunization with an antigen of interest, the transgenic mammals of the invention produce high-affinity human-IgM positive ($hIgM^+$) B cells producing high affinity chimeric human IgMs specific for said antigen.

In addition, following induction of site-specific recombination in vitro or in vivo, the B-cells of the non-human transgenic mammals switch expression of chimeric human antibodies isotype from IgM to IgE, to produce functional human-IgE positive ($hIgE^+$) B cells expressing high affinity chimeric human IgE antibodies specific for said antigen.

Therefore, the non-human transgenic mammal according to the invention has the advantage of generating hybridomas producing high-affinity chimeric human monoclonal IgM or IgE antibodies, specific for any antigen of interest, at levels similar to those usually observed with hybridomas. The methods for producing humanized IgE antibodies specific for an antigen of interest that use the transgenic mammal of the invention are thus much more simple, efficient, rapid and economical than the methods of the prior art.

In addition, this non-human transgenic mammal which produces detectable levels of functional $IgE^+$ B cells can also be used as model to study $IgE^+$ B cells maturation in vivo or in vitro following site-specific recombinase induced IgM to IgE switch in the non-human transgenic mammal B cells.

Furthermore, the non-human transgenic mammal which produces detectable levels of functional chimeric human $IgE^+$ B expressing high affinity chimeric human IgE antibodies comprising human IgE heavy chain constant region can also be used as model to study IgE antibodies functions by recruiting human effector cells, for example in double transgenic non-human mammals further expressing a human or humanized IgE receptor.

According to a preferred embodiment of said non-human transgenic mammal, said human heavy-chain constant genes Cmu and Cepsilon, each comprise human CH1, CH2, CH3 and CH4 exons and human membrane M1 and M2 exons, separated by the corresponding introns. Preferably, said human heavy-chain constant gene Cmu comprises the sequence SEQ ID NO: 2 and said human heavy-chain constant gene Cepsilon comprises the sequence SEQ ID NO: 3.

According to another preferred embodiment of said non-human transgenic mammal, the site-specific recombination sequences are loxP sequences (SEQ ID NO: 5) of Cre recombinase.

According to yet another preferred embodiment of said non-human transgenic mammal, the human transgenic DNA construct further comprises a selection marker gene. The selection marker gene, which is capable of selecting mammalian cells having integrated the human transgenic DNA construct in their genome, is advantageously the neomycine resistance gene (SEQ ID NO: 4). The selection marker gene is preferably flanked by site-specific recombination sequences. More preferably, the selection marker gene is inserted between the second site-specific recombination sequence (situated immediately downstream of the end of the human Cmu gene) and a third site-specific recombination site situated immediately upstream of the start of human Cepsilon gene, wherein the three site-specific recombination sequences are in the same orientation and the third site-specific recombination sequence is capable of site-specific recombination with the first and/or the second one. The site-specific recombination sequences are advantageously loxP sequences (SEQ ID NO: 5) of Cre recombinase. The selection marker gene is used to select the homologous recombinant non-human mammal embryonic stem cells having integrated the transgenic DNA construct in the targeted endogenous IgH locus. After selection of the homologous-recombinant cells, it can be deleted, in vitro or in vivo, using a site-specific recombinase.

According to an advantageous arrangement of said embodiment, said human transgenic DNA construct comprises or consists of the sequence SEQ ID NO: 6.

According to another preferred embodiment of said non-human transgenic mammal, it is homozygous for said human transgenic DNA construct.

According to yet another preferred embodiment of said non-human transgenic mammal, it further comprises a human immunoglobulin light chain transgene, preferably a human immunoglobulin kappa light chain transgene.

According to yet another preferred embodiment of said non-human transgenic mammal, it further comprises a human or humanized high affinity IgE receptor (FcεRI) transgene. Preferably, said non-human transgenic mammal is a knock-in transgenic mammal comprising the replacement of its endogenous high affinity IgE receptor alpha-chain (α-chain) gene with its human homologue. An example of this transgenic mammal is described in Dombrowicz et al., J. Immunol., 1996, 157, 1645-1651).

According to yet another preferred embodiment of said non-human transgenic mammal, it further comprises a transgene encoding a site-specific recombinase specific for said recombination sequences, preferably a transgene encoding an inducible recombinase, more preferably a Cre recombinase transgene encoding an inducible Cre, such as for example a tamoxifen-inducible Cre recombinase. An example of this transgenic mammal is described in Metzger, D. and Chambon, P., Methods, 2001, 24, 71-80.

The transgenic mammal is advantageously homozygous for said transgene(s).

According to an advantageous arrangement of the previous embodiments it is a multiple transgenic mice comprising at least one, preferably at least two, additional transgenes chosen from a human immunoglobulin light chain transgene, a human or humanized high affinity IgE receptor transgene and transgene encoding a recombinase specific for said recombination sequences, as defined above.

The transgenic non-human mammal of the invention comprises said human Cmu and Cepsilon transgenes and eventually said additional transgenes in all its somatic and germ cells. Therefore, the transgenes are transmitted to the transgenic non-human mammal progeny. The invention encompasses also the progeny of said transgenic non-human mammal.

The invention encompasses transgenic animals obtained from any mammalian species, preferably from laboratory mammals, more preferably from laboratory rodents.

According to yet another preferred embodiment of said transgenic mammal, it is a transgenic mouse.

The transgenic mammal of the invention is useful for producing chimeric human antibodies of IgM or IgE isotype, specific for an antigen of interest.

Therefore a subject of the present invention is the use of the transgenic mammal of the invention for producing chimeric human antibodies of IgM or IgE isotype, specific for an antigen of interest.

Another subject of the present invention is a method for producing a chimeric human IgM antibody specific for an antigen of interest, comprising at least:

a) contacting a transgenic non-human mammal of the invention with the antigen of interest, to induce IgM antibody production in the B-cells of said mammal, and b) collecting said IgM antibody.

Another subject of the present invention is a method for producing a chimeric human IgE antibody specific for an antigen of interest, comprising at least:

a) contacting a transgenic non-human mammal of the invention with the antigen of interest, to induce IgM antibody production in the B-cells of said mammal, b) inducing site-specific recombination between said first and second recombination sequences of the human transgenic DNA construct from the B-cells of said mammal, to elicit IgE production in said B-cells, and c) collecting said IgE antibody.

The antigen which is used in the present invention is any natural, recombinant or synthetic substance which is able to induce a specific immune response, including the production of specific antibodies, when introduced into a non-human transgenic mammal according to the invention. For example, the antigen, comprises one or more of a protein, peptide, lipid, sugar, nucleic acid, and/or mineral.

Step a) of the methods is performed by immunizing the transgenic non-human mammal with the antigen of interest according to standard protocols which are known in the art.

The antibody may be collected from the serum or B-cell (s) harvested from said mammal. Preferably, the antibody is collected from B-cell(s) which have been harvested from said mammal and further immortalized.

The site-specific recombination may be induced in vivo, in the non-human transgenic mammal or in vitro, in the B-cells harvested from said transgenic mammal and, preferably, further immortalized.

The induction in vivo is preferably performed using a transgenic mammal comprising a site-specific recombinase gene encoding a recombinase specific for said recombination sequences, more preferably, said recombinase gene is an additional transgene of the transgenic mammal coding for an inducible recombinase, as defined before.

The induction in vitro is preferably performed by immortalizing the B-cells harvested from the transgenic mammal and introducing into the immortalized B cells, an expression vector which encodes the site-specific recombinase, the site-specific recombinase itself or the site-specific recombinase inductor, when the transgenic mammal comprises a recombinase transgene, as defined before.

The expression vector is advantageously an expression plasmid comprising a recombinase gene encoding a site-specific recombinase specific for said recombination sequences, wherein said recombinase gene is expressible, in vitro, in said B-cells. For example, the recombinase gene is under the control of a ubiquitous promoter, such as the CMV promoter. The site-specific recombinase which is introduced into the cells is advantageously fused to a cell penetrating peptide (CPP) sequence such as for example the sequence of a CPP derived from HIV Tat basic domain.

According to an advantageous embodiment of said method, the site-specific recombination is induced in vitro in the B-cells harvested from said transgenic mammal and further immortalized.

B-cell immortalization is performed by fusion of the B-cells with a myeloma cell line, a lymphoblastoid cell line, lymphoma cells or an heteromyeloma cell line, according to standard hybridoma production techniques. Preferably, the B-cells are immortalized by fusion with a murine myeloma cell line, more preferably a murine myeloma cell line like the SP2/0 cell line, which does not produce any murine antibody, is immortalized, and possesses the entire secretion machinery necessary for the secretion of immunoglobulins. The immortalized B-cells are screened for specific antibody production using conventional assays like ELISA. After screening, they are usually cloned using standard methods. The antibodies which are secreted by the immortalized B-cells are harvested from the extracellular medium and usually further purified by conventional techniques known to the persons skilled in the art, such as affinity chromatography.

The chimeric human IgM or IgE antibodies specific for an antigen of interest which are produced by the methods of the invention are polyclonal or monoclonal antibodies. Preferably, said antibodies are monoclonal antibodies. These antibodies, in particular the IgE antibodies, are useful for diagnosis and therapy of human diseases in particular, allergy and cancer. The chimeric human IgE antibodies specific for an antigen of interest are used as standards and controls in human allergy assays. Alternatively, they are use as therapeutic antibodies for cancer immunotherapy.

The subject of the present invention is also an isolated polynucleotide comprising the human transgenic DNA construct as defined above. The isolated polynucleotide, either synthetic or recombinant, may be DNA, RNA or combination thereof, either single- and/or double-stranded, preferably double-stranded DNA. According to another preferred embodiment, the polynucleotide further comprises DNA fragments from the endogenous IgH locus of said mammal comprising the sequences immediately upstream and downstream of its switch sequence Sμ, and said DNA fragments being inserted immediately upstream of the first site-specific recombination sequence and immediately downstream of the human Cepsilon gene, respectively of the human transgenic DNA construct as defined above. The DNA fragments, named 5'and 3' homology arms or 5' and 3' arms, are advantageously of about 5 kb. The DNA fragments correspond advantageously to mouse JH/Eμ and Cμ regions, respectively. Preferably, the DNA fragments are from mouse IgH locus. More preferably, the DNA fragments comprise positions 131281 to 136441 (SEQ ID NO: 7) and 140101 to 145032 (SEQ ID NO: 8), respectively of mouse chromosome 12 sequence Genbank/EMBL accession number AC073553.

According to another preferred embodiment, the polynucleotide comprises or consists of the sequence SEQ ID NO: 9.

Another subject of the present invention is a targeting vector comprising the human transgenic DNA construct flanked by 5'and 3' homology arms, as defined above. Vectors include usual vectors used in genetic engineering including for example plasmids and viral vectors. The targeting vector is useful for producing the transgenic mammal of the invention. According to a preferred embodiment, said targeting vector is a plasmid. According to another preferred embodiment, said targeting vector comprises or consists of SEQ ID NO: 10.

The subject of the present invention is also an isolated cell comprising the human transgenic DNA construct as defined above, with the exclusion of human embryonic stem cells. The cell may be eukaryotic or prokaryotic. According to a preferred embodiment, said cell is a homologous-recombinant cell comprising the human transgenic DNA construct inserted in its endogenous IgH locus, in place of Su. Said homologous-recombinant cell is advantageously obtained by introducing the targeting vector as defined above in a cell, thus allowing the insertion of the transgenic DNA construct in the targeted IgH locus.

According to another preferred embodiment, said cell is an embryonic stem cell from a non-human mammal. Preferably, the non-human mammal embryonic stem cell is a homologous-recombinant cell as defined above. The homologous recombinant stem cell is useful for producing the non-human transgenic mammal according to the invention.

According to yet another preferred embodiment, said cell is a B-cell harvested from a non-human transgenic mammal of the invention immunized with an antigen of interest, which B-cell produces a chimeric human antibody of IgM or IgE isotype, specific for an antigen of interest. According to an advantageous arrangement of said embodiment, said B-cell has been further immortalized. Said immortalized B-cells is advantageously an hybridoma. Preferably, said immortalized B-cell is an IgE producing B-cell further comprising a site-specific recombinase-induced deletion of its human Cmu transgene.

The polynucleotide, targeting vector and non-human mammal embryonic stem cell according to the invention are useful for producing the non-human transgenic mammal of the invention. The B-cell harvested from a non-human transgenic mammal of the invention immunized with an antigen of interest, in particular the immortalized B-cell is useful for producing human chimeric IgM and IgE antibodies specific for an antigen of interest.

Another subject of the present invention is a kit for producing chimeric human IgM or IgE antibodies specific for an antigen of interest, comprising at least:

- a non-human transgenic mammal of the invention, and eventually, an antigen of interest, or
- a B-cell harvested from a non-human transgenic mammal of the invention immunized with said antigen of interest, which B-cell produces a chimeric human antibody of IgM or IgE isotype, specific for an antigen of interest, preferably a B-cell which has been further immortalized, more preferably an IgE producing B-cell further comprising a site-specific recombinase-induced deletion of its human Cmu transgene.

The practice of the present invention will employ, unless otherwise indicated, conventional techniques which are within the skill of the art. Such techniques are explained fully in the literature.

The different sequences which are used for constructing the polynucleotide and derived targeting vector, cell, transgenic mammals of the invention, including the sequences of human and non-human mammal immunoglobulin genes, are known in the art and accessible in databases. The polynucleotide and targeting vector according to the invention are constructed and introduced in a host cell by the well-known recombinant DNA and genetic engineering techniques using classical methods, according to standard procedures as those described in: *Current Protocols in Molecular Biology* (Frederick M AUSUBEL, 2000, Wiley and son Inc, Library of Congress, USA) and *Molecular Cloning*: *A Laboratory Manual, Third Edition*, (Sambrook et al, 2001, Cold Spring Harbor, N.Y.: Cold Spring Harbor Laboratory Press). For example, the polynucleotide is produced by amplification of a nucleic sequence by PCR or RT-PCR, by screening genomic DNA libraries by hybridization with a homologous probe, by total or partial chemical synthesis, or by a combination of said techniques. The insertion of gene fragments into the genome of non-human mammals may be carried out in a random manner, preferably it is carried out in a targeted manner, by homologous recombination with an appropriate targeting vector optionally comprising recombination sequences for a site-specific recombinase such as the loxP sites of Cre recombinase. The inactivation or deletion of gene fragments in the genome of non-human mammals is carried out by homologous recombination with an appropriate targeting vector optionally comprising recombination sequences for a site-specific recombinase such as the loxP sites of Cre recombinase. The transgenic animals according to the invention are obtained by conventional methods for animal transgenesis, according to the standard protocols as described in *Transgenic Mouse*: *Methods and Protocols*; *Methods in Molecular Biology*, Clifton, N.J., Volume 209, October 2002, edited by: Marten H Hofker, Jan Van Deursen, Marten H Hofker and Jan Van Deursen, published by Holly T Sklar: Humana Press. The multiple transgenic animals are obtained by crossing animals transgenic for human mu-epsilon heavy-chains with one or more animals transgenic for human immunoglobulin light chain, human or humanized high affinity IgE receptor, and/or a site-specific recombinase, as defined above. The chimeric human IgM and IgE antibodies are prepared by conventional techniques known to persons skilled in the art, such as those described in *Antibodies: A Laboratory Manual*, E. Howell and D. Lane, Cold Spring Harbor Laboratory, 1988.

In addition to the preceding features, the invention also comprises other features which will emerge from the description which follows, which refers to examples of production and use of transgenic non-human mammals according to the present invention and to the appended drawings in which:

FIG. 1 represents the construction of transgenic mice by knock-in of a human C mu/neo/human C epsilon cassette downstream of the endogenous mouse JH region. wt mouse IgH locus is represented (not scale) with the end of the VH(D)JH cluster, the switch mu region and the first endogenous mouse mu and delta heavy chain constant genes. The targeting vector contains: the 3'arm corresponding to the mouse DJH cluster, a floxed human mu heavy chain constant gene, a floxed Neo resistance gene, a human epsilon heavy chain constant gene and the 3'arm corresponding to the mouse endogenous mu heavy chain constant gene. After homologous recombination in ES cells the S mu region is replaced by the human genes. Human IgM (hIgM) is expressed and allows B cell development and hIgM production. After deletion of the floxed genes upon Cre-loxP-mediated recombination (named herein as creting) in vitro or in vivo, hIgE production occurs in vitro, in hybridomas or in vivo, in B-cells.

FIG. 2 represents the sequence of the targeting vector (SEQ ID NO: 10) used for constructing the Mu-Epsilon (also named as InEps) transgenic mice. Exons are in bold. loxP sequences are highlighted in grey. PolyA signals are boxed. Core Emu sequence is underlined. Vector sequences are in italics.

Figure 3:
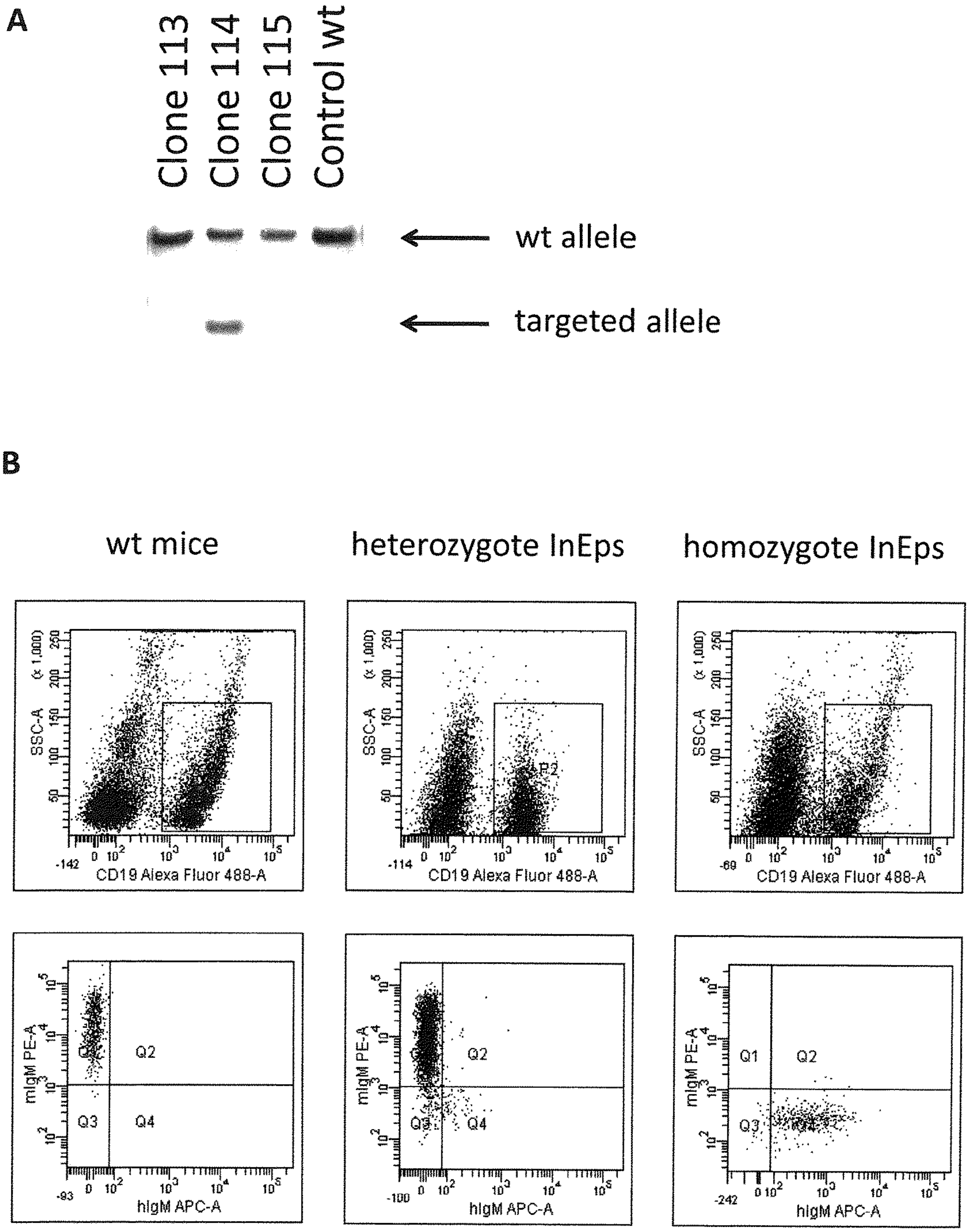

FIG. 3 illustrates the validation of the construction at the genomic and protein level. (A) Screening of ES cells after transfection of the knock-in vector. Genomic DNA was digested with EcoRI and a mouse C delta probe was used to detect recombinant clones. Wt allele results in a band of about 8 kb and recombinant allele gives a band of about 4 kb. (B) Screening of human IgM expression on blood lymphocytes. Lymphocytes were stained with anti-mouse CD19 FITC (eB1D3; BECKMAN COULTER), anti-mouse IgM PE (eB121-15F9; BECKMAN COULTER) and anti-human IgM APC (SA-DA4; BECKMAN COULTER) antibodies. B cells were gated on CD 19+ lymphocytes and analysed for human IgM expression. Homozygote mice, named as Mu-Epsilon or InEps mice, expressed only human IgM. These facs are representatives of at least ten mice per groups.

Figure 4:
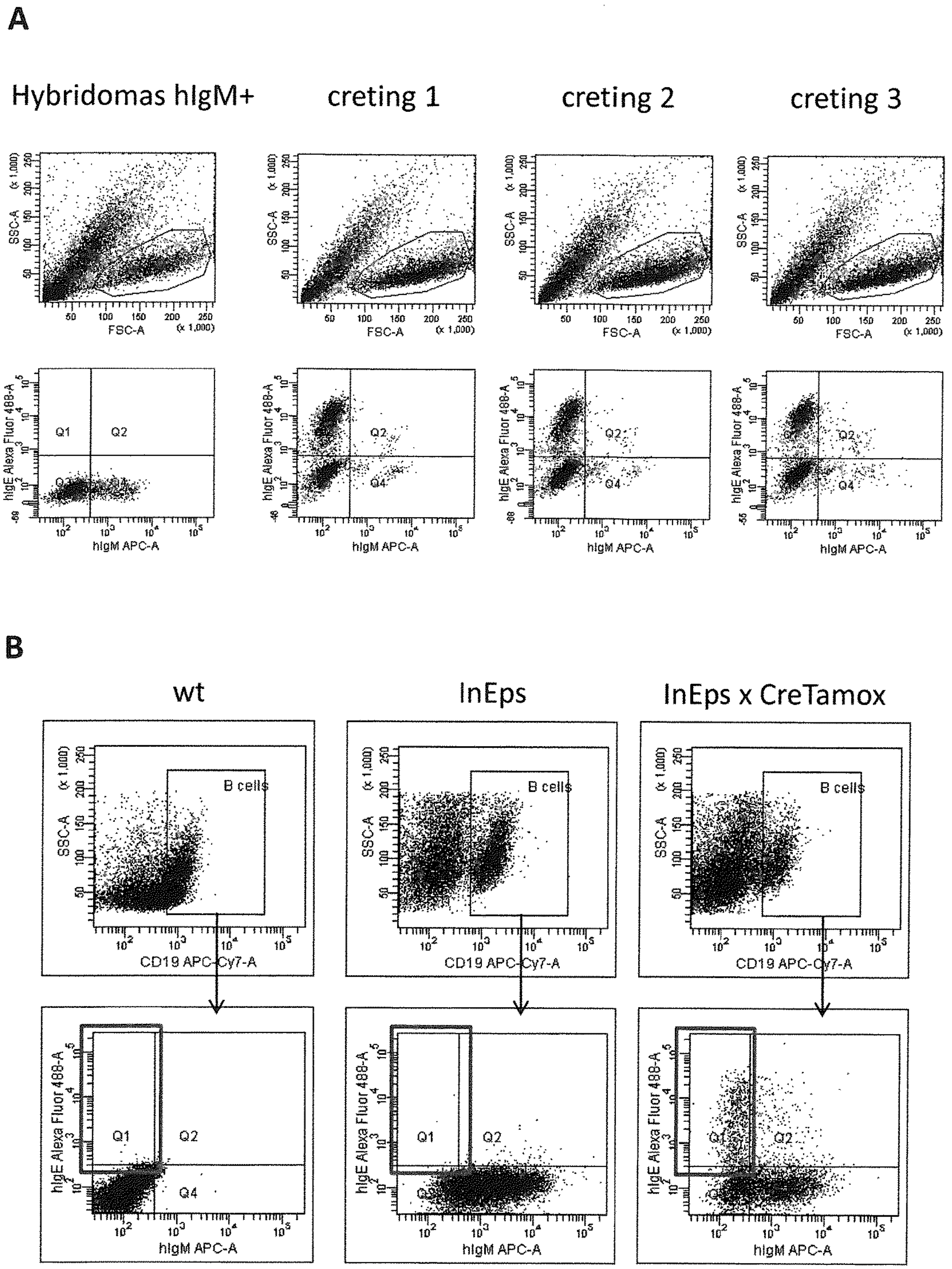

FIG. 4 illustrates in vitro creting of hybridomas and splenocytes and hIgE production. (A) Hybridomas from InEps mice were selected for hIgM production (left panel) and stained intracellularly with anti-human IgM APC (SA-DA4) and anti-human IgE FITC (A80-108F; BECKMAN COULTER). After deletion of the human mu heavy chain constant gene, human IgE expression was detected in the three independent tests (right panels). (B) Splenocytes from wt mice, InEps mice and InEps×CreTamox mice were cultured two days in vitro in presence of LPS (10 μg/mL) and 4-hydroxytamoxifen (500 nM, SIGMA H7904) in order to activate Cre recombinase activity into InEps×CreTamox mice. Cells were stained in intracellular with anti-mouse CD19 APC-H7 (1D3; BECKMAN COULTER), anti-human IgM APC (SA-DA4) and anti-human IgE FITC (A80-108F). Wt cells do not express hIgM or hIgE (left panel), InEps mice only express hIgM (middle panel). hIgE expression was only detected in IpEps×CreTamox mice in the three independent tests (right panels).

Figure 5:
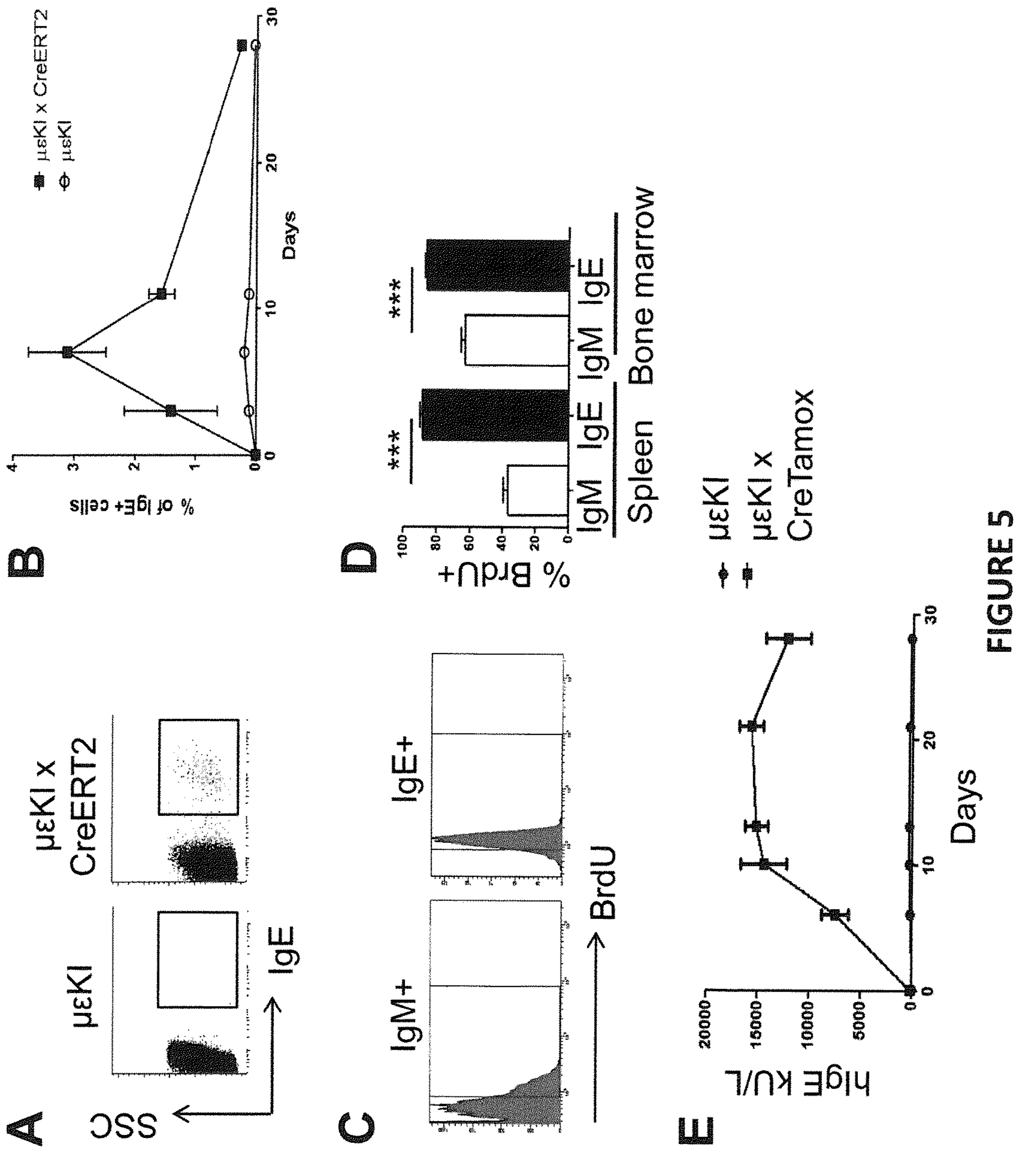

FIG. 5 illustrates in vivo creting of B-cells and chimeric human IgE production in InEps×CreTamox double transgenic mice. (A and B). Intracellular staining of total hIgE+ cells from spleen of InEps (μϵKI) and InEps×CreTamox× CreTamox, also named μϵKI×CreERT2) transgenic mice. (C and D). BrdU incorporation in hIgE+ and hIgM+ cells from spleen and bone marrow of InEps×CreTamox transgenic mice. (E). Kinetic of hIgE production in sera of InEps (μϵκI) and InEps×CreTamox (μϵκI×CreTamox) transgenic mice.

Figure 6:
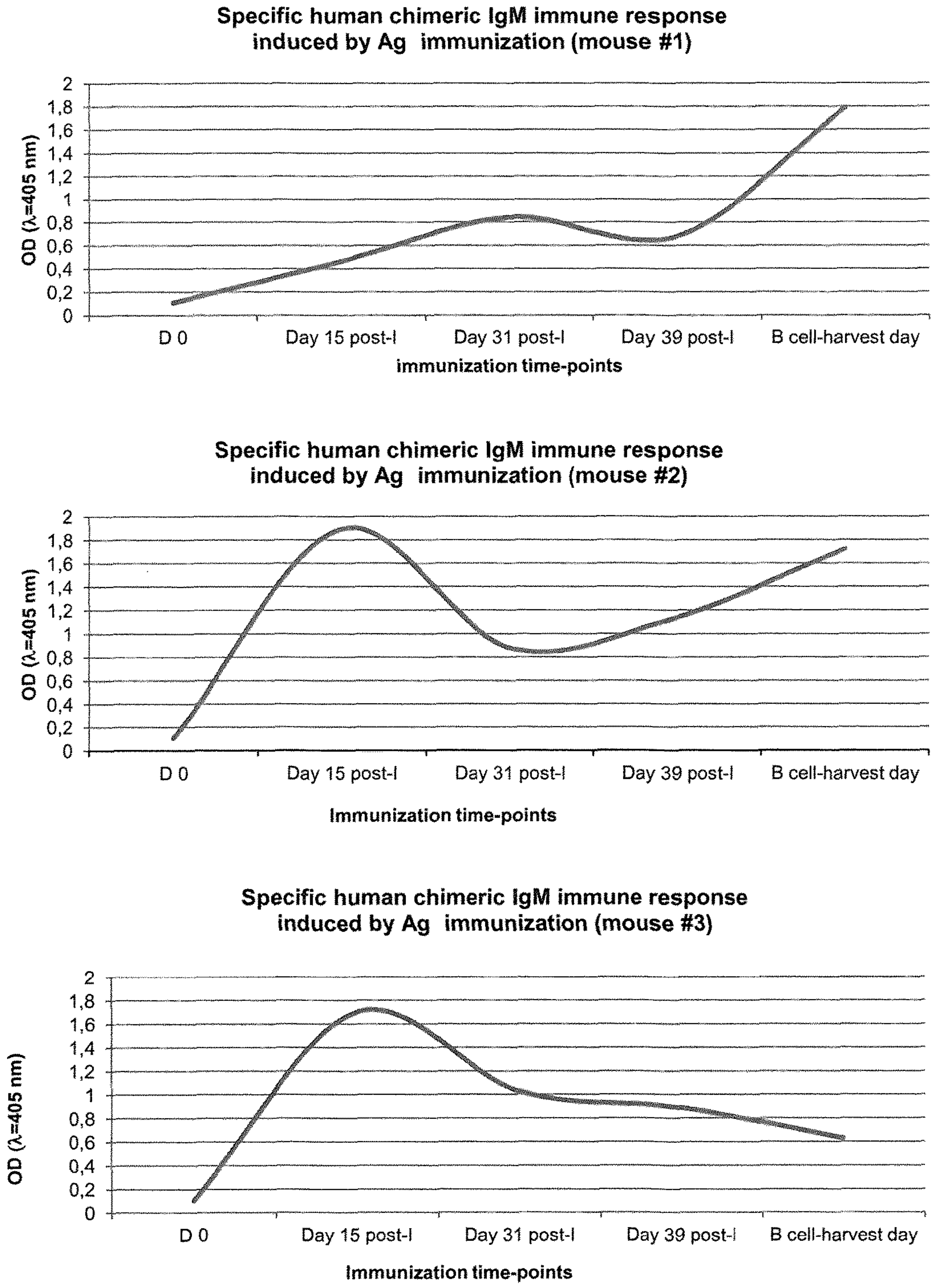

FIG. 6 illustrates specific polyclonal hIgM response anti-antigen in InEps transgenic mice InEps transgenic mice were immunized by intraperitoneal route with a specific protein antigen from a human pathogen (50 μg/immunization/mouse) (in ratio 1:1 with Freund Adjuvant) four times every two weeks. Sera were sampled before immunization (DO) and 2 weeks after each immunization and stored at −20° C. until the ELISA was performed.

FIG. 7 illustrates anti-Ag affinity of Mab IgM clone and Mab IgE-switched clone. Specific anti-antigen IgM expressing clones were transfected with Cre recombinase expression plasmid to excise the human mu-IgH gene and allow the splicing between the rearranged variable genes and the human epsilon-IgH gene. After 5 days of culture, the culture supernatants of the isolated clones were tested by anti-human IgE ELISA.

Figure 8:
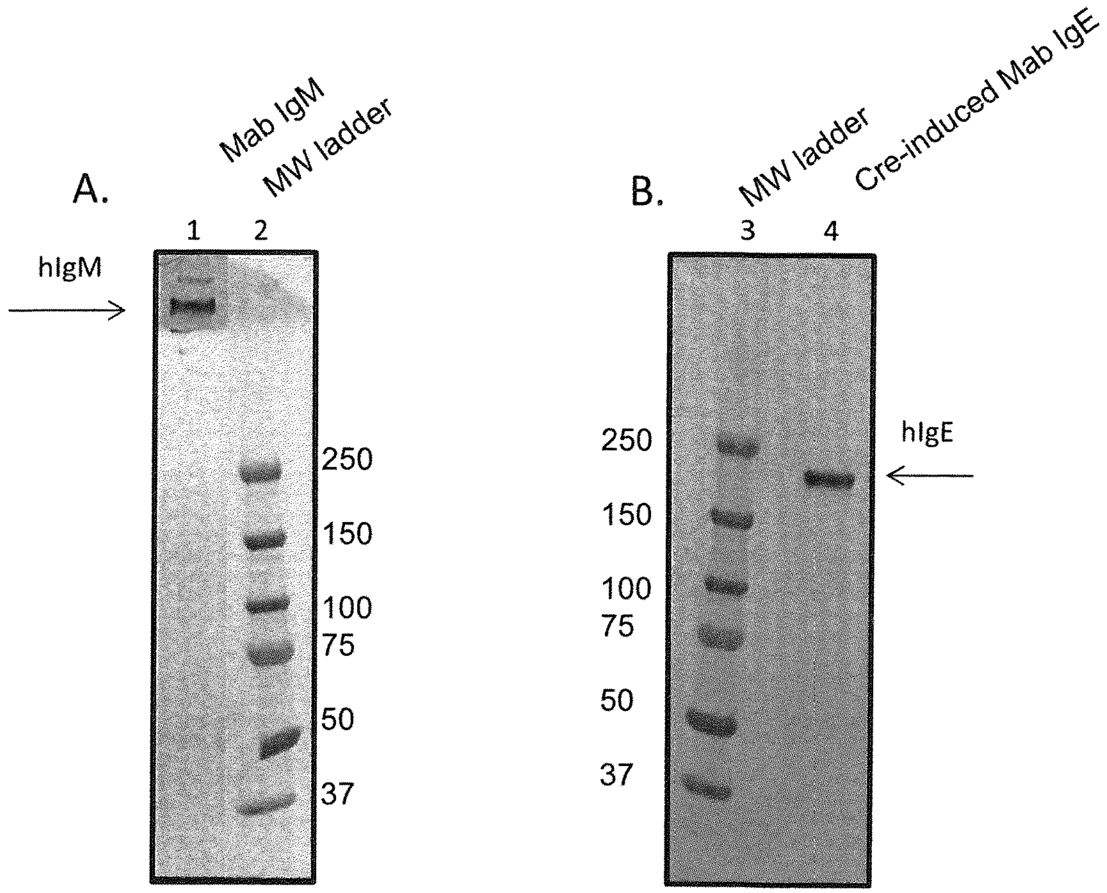

FIG. 8 illustrates monoclonal chimeric human IgM and IgE production in hybridomas derived from Mu-Epsilon transgenic mice. Proteins were analyzed by western-blot using (A) mouse anti-human IgM (SADA4 clone; BECKMAN COULTER) or (B) mouse anti-human IgE (Depsilon 2; BECKMAN COULTER). Lane 1: supernatant of Hybridoma. Lane:4 supernatant of the same mab IgM$^+$ clone after in vitro Cre-induced IgM to IgE switch. Lane 2 & 3: Protein MW ladder (Bio-Rad) in kDalton Arrows in A shows monoclonal chimeric human IgM and arrows in B shows monoclonal chimeric human IgE.

EXAMPLE 1

Production and Characterization of Mu-Epsilon Transgenic Mice

1) Construction of the Homologous Recombination Targeting Vector

DNA manipulations were performed using standards protocols such as those described in Current Protocols in Molecular Biology (Frederick M. AUSUBEL, 2000, Wiley and Son Inc, Library of Congress, USA).

Human mu and epsilon heavy chain constant genes were amplified from human genomic DNA with specific primers containing restriction sites and subcloned into TopoTA 2.1 vectors (INVITROGEN) to yield Topo-hIgM and Topo-hIgM vectors. The vector containing the two arms and the Neo resistance gene (V588) has been described previously (Duchez et al., *Proc. Natl. Acad. Sci. U.S.A.,* 2010, 107: 3064-3069 and WO 2005/047333). Human epsilon heavy chain constant gene was ligated after XhoI restriction of the Topo-hIgE vector and SalI restriction of the V588 vector. A loxP site has been introduced in 5' of the human mu heavy chain constant gene resulting in a ClaI-ClaI fragment, cloned into the ClaI unique site of the V588+hIgE vector (FIG. 1). The resulting targeting vector comprising the human mu and epsilon heavy chain constant genes (human mu-IgH and epsilon-IgH genes; FIG. 1) has the sequence SEQ ID NO: 10 (FIG. 2). The human transgenic construct has the sequence SEQ ID NO: 9.

2) Transfection of ES Cells and Injection into Blastocysts

After sequencing, the targeting vector has been linearized with PvuI and transfected into E14 ES cells with Amaxa® technology according to the manufactor's instructions. Neomycin (300 μg/mL) was added 24 h later to select ES cells. Resistant clones were screened by Southern blot after EcoRI restriction using a mouse Cdelta probe (Laffleur et al., *Methods Mol. Biol.* 2012, 901, 149-159). Wild type allele results in a fragment of about 8 kb and recombinant allele in a band of about 4 kb (FIG. 3A). One clone (114) was used for micro-injection and three agouti positive mice were obtained.

3) Screening of Mu-Epsilon (or InEps) Transgenic Mice by Flow Cytometry

Mice were screened on blood by flow cytometry with a three colors staining against mouse CD19 (FITC eB1D3), mouse IgM (PE eB121-15F9) and human IgM (APC SA-DA4) clone. Cells were analyzed on a Becton Dickinson Fortessa LSRII. B cells were gated on CD19+ lymphocytes and analysed for human IgM expression. Homozygote mice, named hereafter as Mu-Epsilon or InEps mice, expressed only human IgM (FIG. 3B).

4) In Vitro Creting of Hybridomas and Splenocytes and Chimeric Human IgE Production 4.1) hIgE Production from InEps Hybridomas Transiently Expressing Cre Recombinase Hybridomas were generated from InEps mice according to standard techniques (Kohler G, Milstein C, Nature, 1975, 256, 495-497) and selected for hIgM production (FIG. 4A, left panel) $10^6$ hIgM$^+$ hybridoma cells were incubated with 2 μg of a pCDNA3/Cre-recombinase expression vector complexed with 2 μof 293fectin™ (INVITROGEN) for 4 h in Opti-MEM® medium (INVITROGEN) at 37° C. in $CO_2$ atmosphere. The cells were spread over five culture plates (96-well plates, NUNC) in culture medium (DMEM high Glucose/Glutamax/10% Calf Bovine Serum). After 5 days of culture, the hybridoma cells were stained with anti-human IgM APC (SA-DA4) and anti-human IgE FITC (A80-108F).

Transient expression of Cre recombinase enzyme excises the human mu-IgH transgene and allows the splicing between the rearranged variable genes from the mouse and the human epsilon-IgH transgene, resulting in chimeric human IgE expression (FIG. 4A, right panels).

4.2) hIgE Production from InEps×CreTamox Splenocytes Comprising a Tamixofen-Dependent Cre Recombinase InEps mice were bred with CMV-Cre-ER$^T$ transgenic mice (Metzger D. and Chambon P., Methods, 2001, 24, 71-80), a transgenic strain expressing a Cre recombinase fused to a mutated ligand binding domain of the human estrogen receptor (ER), under the control of the ubiquitous cytomegalovirus major IE gene enhancer/promoter, resulting in a tamoxifen-dependent Cre recombinase which is active in a number of cell types, including B cells compartments. The double-transgenic mouse strain homozygous for human Mu-Epsilon IgH genes and at least heterozygous for the CMV-Cre-ER$^T$ transgene is called InEps×CreTamox, μεKI×CreTamox, or μεKI×CreERT2.

Splenocytes were isolated from wild-type, InEps and InEps×CreTamox mice according to conventional methods and cultured two days in vitro in presence of LPS (10 μg/mL) and 4-hydroxytamoxifen (500 nM, SIGMA H7904) in order to activate Cre recombinase activity into InEps×CreTamox mice. Cells were stained with anti-mouse CD19 APC-H7 (1D3), anti-human IgM APC (SA-DA4) and anti-human IgE FITC (A80-108F).

Wt cells do not express hIgM or hIgE (FIG. 4B, left panel), InEps mice only express hIgM (FIG. 4B, middle panel). hIgE expression was only detected in IpEps×CreTamox mice in the three independent tests (FIG. 4B, right panels).

5) In Vivo Creting of B-Cells and Chimeric Human IgE Production

InEps and InEps Cre Tamoxifen (InEps×CreTamox) mice (8 to 10 weeks old) were injected intraperitonally (i.p.) with 2 μg of tamoxifen (SIGMA; T5648) at day 0 and fed orally twice with a feeding needle with 8 mg tamoxifen incorporated to 500 μL of water at day 1 and 2. Serum samples were collected at the indicated times (FIG. 5E) and in parallel mice were sacrified for FACS analysis. Prior to all IgE staining experiments, cells were first washed for 1 minute with 100 μL of acidic buffer per million cells (Ice-cold acid buffer: 0.01 M EDTA, 0.005 M KCl, 0.085 M NaCl, 0.05 M NaAcetate (NaAc), pH=4) to remove passively bound Ig from Fc receptors, then neutralized in PBS and centrifuged.

Intracellular staining of total hIgE+ cells in spleen were performed on $10^6$ splenocytes with IntraPrep Permeabilization Reagent (BECKMAN COULTER; A07803) and quantified by FACS analysis (FIGS. 5A and 5B, n=2 to 5 mice per group). This experiments show the efficiency of the strategy but also the rapid decrease of IgE+ cells.

A cohort of mice were also injected intra-peritoneally (i.p.) with 200 μg of bromodeoxyuridine (BrdU, Sigma B5002) into PBS at day 20 and further fed with BrdU during the time of the experiment (10 days) into water (500 μg/mL). For the staining $2 \cdot 10^6$ cells were washed, blocked, fixed and finally permeabilized using the BrdU Flow kit (Beckton Dickinson). BrdU epitopes were released by DNAse treatment 1 hour at 37° C. Finally, intra-cellular class-specific Ig staining (IgM and IgE) was for 20 minutes at RT and BrdU staining for another 20 minutes at room temperature. BrdU incorporation was evaluated by FACS analysis (FIG. 5C and 5D, n=5 mice per group). This experiments confirm the short-fate of IgE+ cells because these cells were generated during the window of BrdU treatment and failed to accumulate as "long-lived" cell contrary to IgM+ cells.

Secreted human IgE were revealed using an anti-human IgE β-galactosidase and the Methyl-umbelliferyl-β D galactoside as substrate. Results were expressed versus a human IgE standard curve. Mouse sera were assayed at 1:10 dilution for mouse Ig and for human IgE determinations. Kinetic of hIgE production in vivo was determined (FIG. 5E, n=2 to 5 mice per group) and shows a strong hIgE production, culminating at 15 000 kU/L (36 000 μg/L) (human mean at 100 kU/mL (240 μg/L)), consistent with high secretion by plasma cells.

EXAMPLE 2

Production of Antigen-Specific Chimeric Human IgE Using InEps Transgenic Mice InEps transgenic mice were immunized by intraperitoneal route with a specific protein antigen from a human pathogen (50 μg/immunization/mouse) (in ratio 1:1 with Freund Adjuvant) four times every two weeks. Sera were sampled before immunization and 2 weeks after each immunization and stored at −20° C. until the ELISA was performed. Briefly, 96 well plates were coated overnight at 4° C. with antigen (1 μg/mL). Plates were blocked with PBS/BSA 2%. Sera were diluted 100 times in PBS/BSA 0.2% and incubated 2h at 37° C. AP-conjugated secondary Ab (goat anti-human IgM, Beckman Coulter) were used at 1 μg/mL to detect bound hIgM.

FIG. 6 shows that transgenic mice immunized with the antigen produce specific chimeric human IgM.

Hybridomas producing specific chimeric human monoclonal IgM were generated from the immunized transgenic mice according to standard techniques (Kohler G, Milstein C, Nature, 1975, 256, 495-497) and selected for hIgM production by ELISA (Table I).

TABLE I

Validation of human chimeric monoclonal IgM for Diagnostic purpose, as calibrator and positive control

| | OD (B-cell Harvest day) | Collected splenocytes | Screened hybridoma clone | First screening positive clone (by ELISA) | Second screening positive clone (by ELISA) | Stabilized positive clone | Clone validated as calibrator and positive control in diagnostic test on automate |
|---|---|---|---|---|---|---|---|
| Mouse #1 | 1.7895 | 46.10$^6$ cells | 1530 clones | 5 hybridoma clones | 9 clones | 5 | — |

TABLE I-continued

| Validation of human chimeric monoclonal IgM for Diagnostic purpose, as calibrator and positive control | | | | | | | |
|---|---|---|---|---|---|---|---|
| | OD (B-cell Harvest day) | Collected splenocytes | Screened hybridoma clone | First screening positive clone (by ELISA) | Second screening positive clone (by ELISA) | Stabilized positive clone | Clone validated as calibrator and positive control in diagnostic test on automate |
| Mouse #2 | 1.721 | $67.10^6$ cells | 1150 clones | 9 hybridoma clones | 40 clones | 2 | 1 clone |
| Mouse #3 | 0.6295 | $23.10^6$ cells | 960 clones | 17 hybridoma clones | — | 3 | 2 clones |

After selection of the specific anti-antigen human chimeric IgM expressing clone, transient expression of the Cre recombinase enzyme excises the human mu-IgH gene and allows the splicing between the rearranged variable genes and the human epsilon-IgH gene. Briefly, $10^6$ cells were incubated with 2 μg of a pcDNA3/Cre-recombinase expression vector complexed with 2 μL of 293fectin™ (for 4 h in Opti-MEM® medium at 37° C. in CO2 atmosphere. The cells were spread over five culture plates (96-well plates, NUNC) in culture medium (DMEM high Glucose/Glutamax/10% Calf Bovine Serum). After 5 days of culture, the culture supernatants of the isolated clones were tested by anti-human IgE ELISA.

The affinity of transformed clones for the antigen is verified by the anti-antigen ELISA (FIG. 7).

Clones expressing anti-Ag specific human chimeric IgE were identified, subcloned then amplified in culture for IgE production. The clones produce from 0.1 to 50 μg/ml of anti-Ag human chimeric IgE in standard culture conditions (T75 flask (75 cm2); DMEM high glucose, 10% FCS).

Monoclonal chimeric human IgM and IgE production was analyzed by Western-blot (FIG. 8). Proteins were separated on SDS-PAGE gels (4%-15% gradient acrylamide gels, BioRad) under non-reducing conditions and transferred on nitrocellulose membranes. The membranes were blocked with 5% milk in PBS and probed in 3% milk/PBS buffer with the primary mouse anti-human IgM (SADA4 clone, BECKMAN COULTER, 1/2000 diluted) or the primary mouse anti-human IgE (Depsilon 2, BECKMAN COULTER, 1/5000 diluted), revealed with the HRP-conjugated goat anti-mouse IgG1 (BECKMAN COULTER, 1/5000 diluted) and visualized by Peroxidase substrat on colorimetric enzymatic reaction (DAB, SIGMA).

FIG. 8 shows that the hybridomas produce chimeric human IgM before induction of site-specific recombination and human IgE after induction of site-specific recombination.

The invention claimed is:

1. A transgenic mouse, whose genome comprises an endogenous immunoglobulin heavy-chain locus comprising the replacement of its mu heavy-chain switch sequence Sμ by a human transgenic DNA construct comprising respectively from its 5' to its 3'end, at least:

(a) a first site-specific recombination sequence, a human immunoglobulin mu heavy-chain constant gene Cμ or a functional fragment thereof comprising at least human CH1, CH2, CH3 and CH4 exons and human membrane M1 and M2 exons, and a second site-specific recombination sequence, said first and said second recombination sequences being in the same orientation and capable of site-specific recombination, and (b) a human immunoglobulin epsilon heavy-chain constant gene Cϵ or a functional fragment thereof comprising at least human CH1, CH2, CH3 and CH4 exons and human membrane M1 and M2 exons, and wherein said transgenic mouse comprises endogenous B-cells which produce chimeric human immunoglobulin M (IgM) class antibodies and no endogenous IgM antibodies from said transgenic mouse, and wherein said B-cells switch chimeric human antibodies class production from immunoglobulin M to immunoglobulin E (IgE) following site-specific recombination between said first and second site-specific recombination sequences.

2. The transgenic mouse according to claim 1, wherein said site-specific recombination sequences are loxP sites of Cre recombinase.

3. The transgenic mouse according to claim 1, wherein said human transgenic DNA construct comprises the sequence SEQ ID NO: 6.

4. The transgenic mouse according to claim 1, which further comprises one or more of a human immunoglobulin light chain transgene, a human or humanized high affinity IgE receptor transgene, and a transgene encoding a recombinase specific for said recombination sequences.

5. A method for producing a chimeric human IgM antibody specific for an antigen of interest, comprising at least:

a) contacting a transgenic mouse according to claim 1 with the antigen of interest to induce IgM antibody production in the B-cells of said mouse, and (b) collecting said IgM antibody.

6. A method for producing a chimeric human IgE antibody specific for an antigen of interest, comprising at least:

a) contacting a transgenic mouse according to claim 1 with the antigen of interest to induce IgM antibody production in the B-cells of said mouse, (b) inducing site-specific recombination between said first and second recombination sequences of the transgenic DNA construct from the B-cells of said mouse using a recombinase specific for said recombination sequences to elicit IgE production in said B-cells, and (c) collecting said IgE antibody.

7. The method according to claim 6, wherein said site-specific recombination is induced in vitro in B-cells harvested from said transgenic mouse and further immortalized.

8. The method of claim 7, wherein the site-specific recombination is induced by introducing into the immortalized B-cells an expression vector encoding said recombinase, said recombinase, or an inductor of said recombinase.

9. The method according to claim 5, wherein the antibody is collected from B-cells that have been harvested from said mouse and further immortalized.

10. A mouse embryonic stem cell comprising the human transgenic DNA construct as defined in claim 1 inserted in its endogenous immunoglobulin heavy-chain locus in place of Sϵ.

11. A B-cell harvested from a mouse according to claim 1, wherein the B-cell has been immunized with an antigen of interest, wherein said B-cell produces a chimeric human IgM or IgE antibody specific for said antigen of interest, and wherein said B-cell has been immortalized.

12. The B-cell according to claim 11, wherein the B-cell is an IgE producing B-cell further comprising a site-specific recombinase-induced deletion of its human immunoglobulin mu heavy-chain constant transgene Cϵ.

13. A kit for producing chimeric human IgM or IgE antibodies specific for an antigen of interest, comprising at least:

amouse according to claim 1, or a B-cell harvested from the mouse according to claim 1, wherein the mouse has been immunized with an antigen of interest, wherein said B-cell produces a chimeric human IgM or IgE antibody specific for said antigen of interest, and wherein said B-cell has been immortalized.

* * * * *

UNITED STATES PATENT AND TRADEMARK OFFICE

CERTIFICATE OF CORRECTION

PATENT NO. : 9,872,483 B2
APPLICATION NO. : 14/900586
DATED : January 23, 2018
INVENTOR(S) : M. Cogne et al.

It is certified that error appears in the above-identified patent and that said Letters Patent is hereby corrected as shown below:

| Column | Line | Error |
|---|---|---|
| 88 (Claim 10, Line 4) | 55 | "Sε." should read --Sμ-- |
| 88 (Claim 12, Line 4) | 64 | "Cε." should read --Cμ-- |
| 89 (Claim 13, Line 4) | 1 | "amouse" should read --a mouse-- |

Signed and Sealed this
Third Day of July, 2018

Andrei Iancu
*Director of the United States Patent and Trademark Office*